United States Patent [19]
Crute et al.

[11] Patent Number: 6,057,451
[45] Date of Patent: *May 2, 2000

[54] ANTI-HERPESVIRUS COMPOUNDS AND METHODS FOR IDENTIFYING, MAKING AND USING SAME

[75] Inventors: James J. Crute, Danbury, Conn.; Anne-Marie Faucher, Oka, Canada; Christine A. Grygon, New Milford; Karl D. Hargrave, Brookfield, both of Conn.; Bruno Simoneau, Laval; Bounkham Thavonekham, Longeuil, both of Canada

[73] Assignee: Boehringer Ingelheim Pharmaceuticals, Inc., Ridgefield, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/759,201

[22] Filed: Dec. 4, 1996

Related U.S. Application Data

[60] Provisional application No. 60/009,433, Dec. 29, 1995, and provisional application No. 60/023,209, Aug. 2, 1996.

[51] Int. Cl.[7] ...................... C07D 277/00; C07D 277/04; A61K 31/38
[52] U.S. Cl. ........................ 548/194; 548/190; 548/146; 548/193; 514/438; 514/447
[58] Field of Search .................................. 548/190, 194; 514/447

[56] References Cited

U.S. PATENT DOCUMENTS

| | | | |
|---|---|---|---|
| 3,629,247 | 12/1971 | McFarland et al. | 260/240 D |
| 4,746,669 | 5/1988 | Caldwell | 514/342 |
| 5,077,409 | 12/1991 | Wissner | 546/121 |

FOREIGN PATENT DOCUMENTS

| | | | |
|---|---|---|---|
| 279598 | 8/1988 | European Pat. Off. | C07D 277/38 |
| 372776 | 6/1990 | European Pat. Off. | C07D 471/04 |
| 458037 | 11/1991 | European Pat. Off. | C07D 277/22 |
| 545376 | 6/1993 | European Pat. Off. | C07D 277/48 |
| 2276164 | 9/1994 | United Kingdom | C07D 413/12 |
| 9212635 | 8/1992 | WIPO | A01N 43/04 |
| 9318032 | 9/1993 | WIPO | C07D 417/14 |
| 9504049 | 2/1995 | WIPO | C07D 295/08 |
| 9532710 | 12/1995 | WIPO . | |

OTHER PUBLICATIONS

Liebig et al., Arznem.–Forch. (Drug Res.) 24, Nr. 6 (1974), pp. 887–892.

Dicker et. al., Antiviral Research, 28, (1995), 213–224.

Y. Kawamatsu et al., "2–Amino–4–Phenylthiazole Derivatives as Anti–Atherogenic Agents", *Eur. J. Med. Chem.*, 16, pp. 355–362 (1981).

J.A. Lowe et al., "1–Naphthylpiperazine Derivatives as Potential Atypical Antipsychotic Agents", *J. Med. Chem.*, 34, pp. 1860–1866 (1991).

C. Selway et al., "Parallel–Compound Synthesis: Methodology for Accelerating Drug Discovery", *Bioorganic and Medicinal Chemistry*, 4, pp. 645–654 (1996).

*Chemical Abstracts*, vol. No. 110, page No. 716, Abstract No. 135227 (1986).

*Primary Examiner*—Jose' G. Dees
*Assistant Examiner*—Sabiha N. Qazi
*Attorney, Agent, or Firm*—Robert P. Raymond; Anthony P. Bottino; Mary-Ellen Devlin

[57] ABSTRACT

This invention relates to methods for inhibiting herpes replication and for treating herpes infection in a mammal by inhibiting the herpes helicase-primase enzyme complex. This invention also relates to thiazolyphenyl derivatives that inhibit the herpes helicase-primase and to pharmaceutical compositions comprising the thiazolylphenyl derivatives, to methods of using and methods of producing the thiazolylphenyl derivatives.

15 Claims, 5 Drawing Sheets

ANTI-HERPESVIRUS COMPOUNDS AND METHODS FOR IDENTIFYING, MAKING AND USING SAME

This appln. claims benefit of provisional applns. 60/023,209 filed Aug. 2, 1996 and 60/009,433 filed Dec. 29, 1995.

TECHNICAL FIELD OF THE INVENTION

This invention relates to methods for inhibiting herpes replication and for treating herpes infection in a mammal by inhibiting the herpes helicase-primase enzyme complex. In a preferred embodiment, this invention relates to thiazolylphenyl derivatives that inhibit the herpes helicase-primase. This invention also relates to pharmaceutical compositions comprising the thiazolylphenyl derivatives, to methods of using and producing the thiazolylphenyl derivatives.

BACKGROUND OF THE INVENTION

Herpesviruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the human cytomegalovirus (HCMV) is a leading cause of opportunistic infections in immunosuppressed individuals.

Herpesviruses are complex double-stranded DNA viruses that encode all the enzymes that directly mediate viral chromosomal replication. Seven DNA replication-associated polypeptides are required for human herpesvirus replication. Six of these seven polypeptides show a high degree of homology across all studied human herpesviruses. These six polypeptides, when expressed by the virus, constitute a heterodimeric DNA-dependent DNA polymerase, a monomeric single-stranded DNA binding protein, and a heterotrimeric helicase-primase complex. The seventh DNA replication-associated polypeptide does not display sequence or functional conservation and is involved in the initiation of lytic viral replication.

Without the function of each of the seven herpesvirus-specific DNA replication proteins, herpesvirus chromosomal replication will not initiate or propagate. This has been demonstrated in two ways for DNA replication in HSV-1. First, temperature sensitive HSV-1 strains have been developed and the complementation groups within these strains mapped on a one-to-one correspondence to the seven HSV DNA replication genes. Additionally, transient replication assays that utilized recombinant DNA plasmids containing single DNA replication genes have found that the presence of each of the seven genes was required for the efficient replication of a tester plasmid containing an HSV-1 origin of DNA replication.

More recently, the DNA replication genes in other herpesviruses (i.e., Epstein-Barr virus, cytomegalovirus and varicella zoster virus) have been delineated. These gene sequences were identified as homologous to the HSV-1 DNA replication genes. Furthermore, transient replication assays containing either an Epstein-Barr virus or cytomegalovirus lytic origin of DNA replication confirmed their identity. In varicella zoster virus (the human herpesvirus most closely related to HSV-1) DNA replication genes were found to be highly homologous to HSV-1 (>50% at the amino acid level) and present at identical relative locations on the two viral chromosomes. Although no follow-up analysis on varicella zoster virus DNA replication genes has been presented to date, it is highly unlikely that differences in the varicella zoster virus and HSV-1 DNA replication programs exist.

From the above, it is clear that human DNA replication proteins are unable to substitute for the HSV-1 encoded enzymes. Otherwise, temperature-sensitive viral polypeptides would have been complemented by human counterparts and the defective viruses would have continued to grow and replicate, even at elevated temperatures. Similarly, in transient replication assays, if human proteins were capable of complementing any of the seven herpesvirus-encoded polypeptides, an absolute dependence on the presence of each of these herpesvirus DNA replication-specific genes would not have been observed. Therefore, inhibiting the activity of those virally-encoded proteins represents an effective way of preventing herpesviral replication.

The helicase-primase enzyme occupies a key and critical place in the herpesvirus DNA replication program. The observation that the genes encoding the herpes helicase-primase are not only essential for replication, but are also highly conserved across the range of known herpesviruses underscores the importance of this enzyme in mediating viral chromosomal replication.

In the helicase-primase complex, two of the three polypeptides (e.g., the expression products of the UL5 and UL52 genes of HSV-1) promote catalysis of duplex DNA unwinding and RNA primer biosynthesis. The third polypeptide, encoded by the UL8 gene, appears to modulate primase activity. The assembled helicase-primase enzyme complex functions both in the initiation and propagation stages of herpesvirus DNA replication. It is responsible for the synthesis of RNA primers necessary for the initiation of all new DNA synthesis by the herpesvirus DNA polymerase. Additionally, for DNA replication to proceed, duplex viral chromosomal DNA must first be unwound to the single-stranded replicative intermediate because the herpesvirus DNA polymerase is inactive on fully duplex DNA. The helicase-primase is also responsible for this important DNA unwinding event.

Conventional anti-herpes therapies have not focused on inhibiting the activity of the herpes helicase-primase(see R. E. Boehme et al., Annual Reports in Medicinal Chemistry, 1995, 30, 139). The most widely used anti-herpes agents to date are purine and pyrimidine nucleoside analogs, such as acyclovir and ganciclovir. These nucleoside analogues inhibit replication of viral DNA by their incorporation into a growing DNA strand. The nucleoside analogue-based inhibitors of HSV-1 growth have found only limited success and are not generally useful in treating recurring infections in the majority of patients. In addition, the infection of humans by other herpesviruses, such as varicella zoster virus or cytomegalovirus, show little or no responsiveness to nucleoside-based therapies.

The lack of broad spectrum anti-herpesvirus activity by the nucleoside-based therapies is not surprising because these compounds act by indirect biological mechanisms. Nucleoside analogues must first be activated to the nucleoside monophosphate by a virally-encoded thymidine kinase enzyme. It should be pointed out that only HSV and varicella zoster virus encode thymidine kinase enzymes. This may, in part, explain the inability to adapt nucleoside-based therapies to the treatment of other human herpesviruses. After initial phosphorylation, the nucleoside analogue monophosphate must be further phosphorylated to the triphosphate by human-encoded enzymes prior to its action. Ultimately, the triphosphorylated nucleoside analogue is incorporated into a nascent DNA chain during viral genomic replication, thereby inhibiting the elongation of that DNA chain by the herpes DNA polymerase.

The final incorporation step of the nucleoside-based therapies has been characterized as "competitive" because the herpes DNA polymerase does not display a preference for the activated nucleoside drug versus normal deoxynucleoside triphosphates. However, because the action of the DNA polymerase is not considered rate-limiting for herpesvirus DNA replication, the utility of nucleoside-derived compounds in treating herpesvirus infections is necessarily limited. Accordingly, the need for effective, safe therapeutic agents for treating herpesvirus infections continues to exist.

SUMMARY OF THE INVENTION

The invention described herein overcomes the above-mentioned limitations and satisfies the above-mentioned needs by providing non-nucleoside-based inhibitors that act directly in interfering with the likely rate-limiting process in herpesvirus DNA replication: the action of the helicase-primase enzyme. Furthermore, since the herpesvirus helicase-primase enzyme is conserved across the human herpesviruses, compounds of this invention are effective against the full spectrum of herpesviruses, including HSV, varicella zoster virus and cytomegalovirus, and also against nucleoside-nonresponsive and nucleoside-resistant herpes infections.

One objective of this invention is to provide methods for inhibiting a herpes helicase-primase, for inhibiting replication of a herpesvirus and for treating herpes infection in a mammal using a non-nucleoside compound characterized by:

(a) an ability to inhibit DNA-dependent NTPase activity of the herpes helicase-primase;

(b) an ability to stabilize the interaction between the herpes helicase-primase and a DNA substrate;

(c) an inability to inhibit DNA-independent NTPase activity of the herpes helicase-primase;

(d) an inability to bind directly to double-stranded DNA; and (e) an inability to inhibit the herpes origin binding protein helicase encoded by the UL9 gene of HSV.

A further objective of this invention is to provide thiazolylphenyl derivatives useful in the methods of this invention and pharmaceutical compositions comprising those thiazolylphenyl derivatives.

Another objective of this invention is to provide processes for preparing the thiazolylphenyl derivatives of this invention.

Yet another objective of this invention is to provide a method for identifying non-nucleoside herpes helicase-primase inhibitors by screening for (1)inhibition of single-stranded DNA-dependent NTPase activity and (2) lack of inhibition of DNA-independent NTPase activity of a herpes helicase-primase.

A further objective of this invention is to provide non-nucleoside herpes helicase-primase inhibitors identified using the methods of this invention.

Yet a further objective of this invention is to provide non-nucleoside herpes helicase-primase inhibitors characterized by:

(a) an ability to inhibit DNA-dependent NTPase activity of the herpes helicase-primase;

(b) an ability to stabilize the interaction between the herpes helicase-primase and a DNA substrate;

(c) an ability to inhibit replication of a herpesvirus in cell culture by at least about 50% at a concentration of less than about 500 nM;

(d) an inability to inhibit DNA-independent NTPase activity of the herpes helicase-primase;

(e) an inability to bind directly to double-stranded DNA; and (f) an inability to inhibit the herpes origin binding protein helicase encoded by the UL9 gene of HSV-1.

Still a further objective of this invention is to provide pharmaceutical compositions containing the non-nucleoside inhibitors of this invention and methods for treating herpes infection in a mammal using those pharmaceutical compositions.

DETAILED DESCRIPTION OF THE INVENTION

Figure 1:
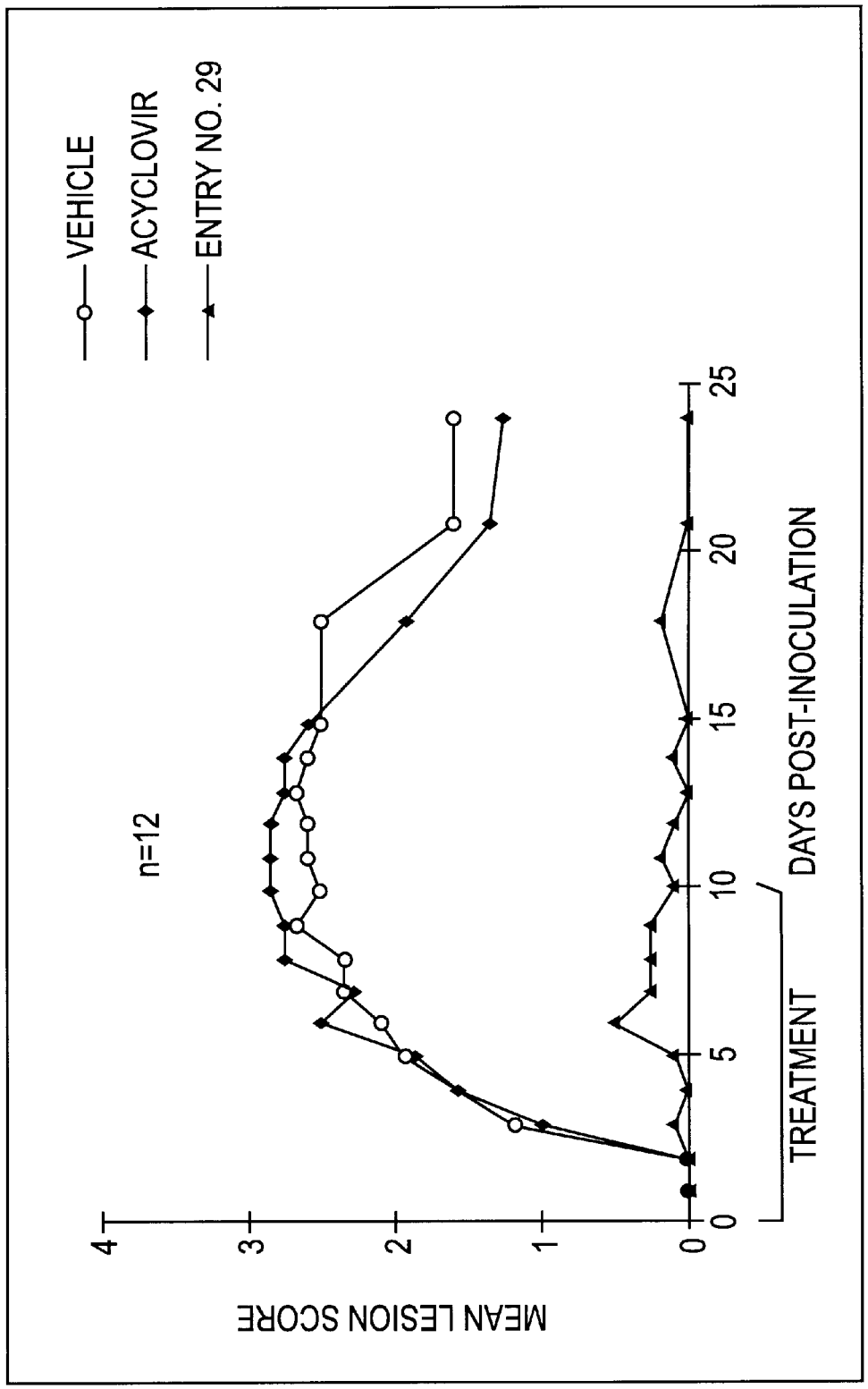
FIG. 1 graphically illustrates the therapeutic effect of acyclovir and a thiazolylphenyl derivative of Group 1 (described hereinafter) against an acyclovir-resistant HSV infection in an immunodeficient mouse model. The HSV strain in this instance is HSV-1 PAA$^r$5.

As used herein, the following definitions apply unless otherwise noted:

With reference to the instances where (R) or (S) is used to designate the configuration of a radical, e.g. $R^4$ of the compound of formula 1, the designation is done in the context of the compound and not in the context of the radical alone.

The term "halo" as used herein means a halo radical selected from bromo, chloro, fluoro or iodo.

The term "herpes" as used herein refers to any virus in the herpes family of viruses and particularly, to those herpesviruses that encode a herpes helicase-primase homologous to the herpes helicase-primase of HSV-1. The herpes family of viruses includes, but is not limited to, HSV-1, HSV-2, cytomegalovirus, varicella zoster virus and Epstein-Barr virus.

The term "lower alkanoyl" as used herein, either alone or in combination with another radical, means a straight chain 1-oxoalkyl containing from one to six carbon atoms or a branched chain 1-oxoalkyl containing from four to six carbon atoms; for example, acetyl, propionyl(1-oxopropyl), 2-methyl-1-oxopropyl, 2-methylpropionyl and 2-ethylbutyryl. Note that the term "lower alkanoyl" when used in combination with "lower cycloalkyl" would include "(lower cycloalkyl)carbonyl".

The term "(1-3C)alkyl" as used herein, either alone or in combination with another radical, means alkyl radicals containing from one to three carbon atoms and includes methyl, ethyl, propyl and 1-methylethyl.

The term "lower alkyl" as used herein, either alone or in combination with another radical, means straight chain alkyl radicals containing one to four carbon atoms and branched chain alkyl radicals containing three to four carbon atoms and includes methyl, ethyl, propyl, butyl, 1-methylethyl, 1-methylpropyl, 2-methylpropyl, 1,1-dimethylethyl and 2,2-dimethylpropyl.

The term "(1-8C)alkyl" as used herein means straight and branched chain alkyl radicals containing from one to eight carbon atoms and includes ethyl, butyl, 1-methylpropyl, 1-ethylpropyl, 2,2-dimethylpropyl, 1-ethylbutyl, 2-ethyl-2-methylbutyl, 2-ethylbutyl, 1-propylbutyl, 2-propylpentyl and the like.

The term "lower alkenyl", as used herein means an aliphatic hydrocarbon containing two to four carbon atoms and one double bond and includes ethenyl, 1-propenyl, 2-propenyl, 1-butenyl, 2-butenyl and 3-butenyl.

The term "lower alkynyl" as used herein means an aliphatic hydrocarbon containing two to four carbon atoms and one triple bond and includes ethynyl, 1-propynyl, 2-propynyl and 1-butynyl.

The term "{1-(lower alkyl)-(lower cycloalkyl)}" as used herein means a lower cycloalkyl radical bearing a lower alkyl substituent at position 1; for example, 1-ethylcyclopropyl, 1-propylcyclopentyl and 1-propylcyclohexyl.

The term "lower cycloalkyl" as used herein, either alone or in combination with another radical, means saturated cyclic hydrocarbon radicals containing from three to seven carbon atoms and includes cyclopropyl, cyclobutyl, cyclopentyl, cyclohexyl and cycloheptyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "amino" as used herein means an amino radical of formula —$NH_2$. The term "lower alkylamino" as used herein means alkylamino radicals containing one to six carbon atoms and includes methylamino, propylamino, (1-methylethyl)amino and (2-methylbutyl)amino. The term "di(lower alkyl)amino" means an amino radical having two lower alkyl substituents each of which contains one to six carbon atoms and includes dimethylamino, diethylamino, ethylmethylamino and the like.

The term "Het" as used herein means a monovalent radical derived by removal of a hydrogen from a five- or six-membered saturated or unsaturated heterocycle containing from one to two heteroatoms selected from nitrogen, oxygen and sulfur. Optionally, the heterocycle may bear one or two substituents; for example, N-oxido, lower alkyl, phenyl-(1-3C)alkyl, lower alkoxy, halo, amino or lower alkylamino. Examples of suitable heterocycles and optionally substituted heterocycles include pyrrolidine, tetrahydrofuran, thiazolidine, pyrrole, 1H-imidazole, 1-methyl-1H-imidazole, pyrazole, furan, thiophene, oxazole, isoxazole, thiazole, 2-methylthiazole, 2-aminothiazole, 2-(methylamino)-thiazole, piperidine, 1-methylpiperidine, 1-methylpiperazine, 1,4-dioxane, morpholine, pyridine, pyridine N-oxide, pyrimidine, 2,4-dihydroxypyrimidine and 2,4-dimethylpyrimidine.

The term "pharmaceutically acceptable carrier" or "veterinarily acceptable carrier" as used herein means a non-toxic, generally inert vehicle for the active ingredient which does not adversely affect the ingredient.

The term "effective amount" means a predetermined antiviral amount of the antiviral agent, i.e. an amount of the agent sufficient to be effective against the virus in vivo.

The term "inhibit", when used in connection with enzymatic activity, refers generally to inhibiting the enzymatic activity by at least about 50% at a concentration of about 100 $\mu$M (and preferably at a concentration of about 50 $\mu$M, more preferably, at a concentration of about 25 $\mu$M, even more preferably, at a concentration of about 10 $\mu$M and most preferably, at a concentration of about 5 $\mu$M or less) in a conventional in vitro assay for enzymatic inhibition. In contrast, the term "inability to inhibit" refers generally to inhibiting enzymatic activity by no more than about 50% at concentration of about 100 $\mu$M. For example, a compound with an HSV-1 helicase-primase $IC_{50}$ value of 1.5 $\mu$M inhibits HSV-1 helicase-primase activity by 50% at a concentration of 1.5 $\mu$M. Therefore, this compound is an HSV-1 helicase-primase inhibitor, as the term is used herein. However, a compound having an $IC_{50}$ value of 150 $\mu$M inhibits enzymatic activity by 50% at a concentration of 150 $\mu$M and therefore, is not considered an inhibitor of that enzyme.

The term "bind directly to DNA" refers to the ability of a compound to bind to DNA in the absence of added enzyme. It should be understood that the compounds of this invention might bind to DNA when enzyme is present. However, these compounds do not bind to DNA in the absence of enzyme. The ability of a compound to bind directly to DNA is preferably ascertained by UV/VIS spectroscopy. Alternatively, fluorescence or circular dichroism may be used. Each of these techniques is well known and may be carried out using methodology familiar to those of ordinary skill in the art.

In one embodiment, the present invention refers to methods for inhibiting a herpes helicase-primase by stabilizing the interaction between the herpes helicase-primase and its viral DNA substrate. Directly-acting non-nucleoside herpes helicase-primase inhibitors have been identified using the methods of this invention. It has also been established for the first time that effectors of the herpesvirus helicase-primase capable of stabilizing the enzyme complex's interaction with its DNA substrate are capable of directly inhibiting herpes helicase-primase activity.

Without wishing to be bound by theory, it is believed that preferred compounds of this invention bind to an allosteric effector site located on the UL5 or the UL52 subunit of HSV-1 helicase-primase (and homologous regions of other herpesvirus helicase primase enzymes), thereby causing the enzyme to bind more tightly to the DNA substrate. This "stabilization" inhibits enzymatic activity by impeding enzymatic progression along the DNA substrate. It is likely that a particularly favorable binding site for enzymatic inhibition is an allosteric effector site located within the A-B sequence of the UL52 subunit. More specifically, it is believed that the inhibitory action of these compounds is mediated by a terminal "zinc finger" motif on one of the herpes helicase-primase's catalytic subunits.

Compounds useful for inhibiting a herpes helicase-primase according to the above mechanism may be readily identified by assaying a test compound's ability to inhibit enzyme-associated single-stranded DNA-dependent NTPase activity of a herpes helicase-primase (such as the helicase-primase of HSV-1). Such a screening method may advantageously be established for use as a high throughput screen (HTS). An HTS based upon this methodology is typically easier to run and requires less enzyme than other assays, such as the helicase-driven solid phase unwinding assay. Additionally, the enzyme used for the DNA-dependent NTPase assay need not be as pure or used in as great an amount as in the helicase assay.

Compounds active in the HTS may be further assayed to determine their herpes helicase-primase binding specificity. Although the following assays are described in one particular sequence, it should be understood that not all of these assays need to be performed for successful identification of herpes helicase-primase inhibitors. In addition, the exact order of assays may be altered, if desired. These and other procedural options can be considered by those of ordinary skill in the art.

One additional assay that may be run determines the ability of test compounds to inhibit helicase-primase-associated DNA-independent NTPase activity. The compounds useful in this invention do not inhibit this activity, whereas competitively-acting nucleoside analogues do inhibit this activity.

Other assays measure a test compound's ability to inhibit enzyme-mediated RNA primer biosynthesis and stabilize the interaction between the helicase-primase and its DNA substrate. Compounds useful in this invention do not inhibit DNA-independent NTPase activity and do not intercalate into, nor otherwise bind directly to, double-stranded DNA. These activities are also readily measurable by assays known to those of ordinary skill in the art.

Assays designed to measure helicase activity of the herpes helicase-primase in solution may also be performed. Compounds which inhibit helicase activity in that assay can then be counter screened for activity against other eukaryotic helicases, such as the HSV-1 origin binding protein helicase encoded by the UL9 HSV-1 DNA replication specific gene. These origin binding protein-driven DNA unwinding assays are stimulated by the addition of an equimolar amount of the HSV-1 single-stranded DNA binding protein. Compounds displaying less than about 10-fold specificity for the helicase-primase (e.g., $IC_{50}$ (origin binding protein helicase activity)<10 X $IC_{50}$ (helicase-primase helicase activity)) should be excluded as likely non-specific helicase inhibitors. Other identified prokaryotic or eukaryotic helicases could also be used for determining compound specificity.

Another assay measures the ability of a test compound to stabilize the interaction between the helicase-primase and DNA substrates (e.g., those that are naturally occurring, or those designed to mimic either replication fork-like structures or primase recognition sequences). The term "DNA substrate" as used in this context refers to duplex DNA which, in the presence of a herpes helicase-primase, is susceptible to enzymatic activity. It will be appreciated that any sequence of double-stranded DNA which is unwound by a herpes helicase-primase may be used in assays to test the ability of a test compound to stabilize the interaction between the helicase-primase and DNA. Such an assay may be performed by binding the helicase-primase enzyme to a fluorescently labeled DNA substrate, for example, a DNA substrate designed to model a replication fork-like structure or primase consensus binding site. Fluorescence anisotropy may then be used to directly determine the fraction of enzyme bound to target nucleic acid substrates by increasing salt concentrations to fractionally depopulate the enzyme from the DNA target sequence. Addition of stabilizing inhibitors shifts the equilibrium from free (in solution) to bound (to DNA).

A preferred method for identifying a non-nucleoside herpes helicase-primase inhibitor according to this invention comprises the steps of:

(a) measuring the ability of the test compound to inhibit DNA-dependent NTPase activity of the herpes helicase-primase; and (b) measuring the ability of the test compound to inhibit DNA-independent NTPase activity.

In this preferred method, herpes helicase-primase inhibitors according to this invention inhibit DNA-dependent NTPase activity, but do not inhibit DNA-independent NTPase activity.

This invention also envisions various methods for inhibiting a herpes helicase-primase and inhibiting replication of a herpesvirus. According to a preferred embodiment, these methods comprise the step of contacting the helicase primase with a non-nucleoside compound characterized by:

(a) an ability to inhibit DNA-dependent NTPase activity of the herpes helicase-primase;

(b) an ability to stabilize the interaction between the herpes helicase-primase and a DNA substrate;

(c) an inability to inhibit DNA-independent NTPase activity of the herpes helicase-primase;

(d) an inability to bind directly to double-stranded DNA; and (e) an inability to inhibit the herpes origin binding protein helicase encoded by the UL9 gene of HSV-1.

This invention also includes various methods for treating herpes infection in a mammal. In a preferred embodiment that method comprises the step of administering to a mammal in need of such treatment a therapeutically effective amount of a pharmaceutical composition comprising a therapeutically acceptable carrier and a non-nucleoside compound characterized by:

(a) an ability to inhibit DNA-dependent NTPase activity of the herpes helicase-primase;

(b) an ability to stabilize the interaction between the herpes helicase-primase and a DNA substrate;

(c) an inability to inhibit DNA-independent NTPase activity of the herpes helicase-primase;

(d) an inability to bind directly to double-stranded DNA; and (e) an inability to inhibit the herpes origin binding protein helicase encoded by the UL9 gene of HSV-1.

In all of the above-methods, the non-nucleoside compound is preferably further characterized by an ability to inhibit herpes helicase-primase mediated RNA primer biosynthesis. In addition, preferred non-nucleoside inhibitors of this invention are further characterized by an ability to inhibit replication of a herpesvirus in cell culture by at least about 50% at a concentration of less than about 5 $\mu$M (more preferably, less than about 2 $\mu$M, even more preferably, less than about 1 $\mu$M or less than about 500 nM and most preferably, less than about 100 nM). Non-nucleoside compounds of this invention that inhibit replication of a herpesvirus in cell culture by at least about 50% at a concentration of less than about 50 nM (or more preferably, less than about 10 nM and most preferably, less than about 1 nM) are particularly preferred. It is important to recognize that the compounds, compositions and methods of this invention may be used against nucleoside nonresponsive and nucleoside resistant herpes infections.

Using the above noted screening methodologies, a class of thiazolylphenyl derivatives was identified as inhibitors of herpes helicase-primase. These derivatives share the general structure of formula G:

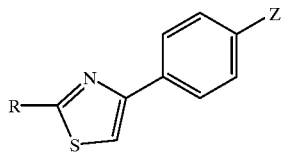

(G)

wherein R is selected from the group consisting of hydrogen, lower alkyl, amino, lower alkylamino, di(lower alkyl)amino, lower alkanoylamino, (lower alkoxycarbonyl)amino, di(lower alkoxycarbonyl)amino, {(lower alkylamino)carbonyl}amino and pyridinylamino; and some preferred definitions for Z are detailed herein.

More particularly, a thiazolylphenyl derivative of this invention is a compound selected from one of the following groups:

Group 1 Compounds: A thiazolylphenyl derivative of formula G wherein R is as defined hereinabove, and Z is $NR^2$-C(O)-Q-CH($R^3$)-$NR^4R^5$ wherein $R^2$ is hydrogen or lower alkyl;

Q is absent (i.e. a valance bond) or methylene;

$R^3$ is hydrogen, lower alkyl, phenyl(lower alkyl) or phenyl(lower alkyl) monosubstituted on the aromatic portion thereof with a halo, hydroxy, lower alkoxy or lower alkyl;

$R^4$ is hydrogen, (1-8C)alkyl, {di(lower alkyl)amino}-(lower alkyl), phenyl(lower)alkyl, phenyl(lower)alkyl monosubstituted or disubstituted on the aromatic portion thereof with a halo, hydroxy, lower alkoxy or lower alkyl; 1-indanyl, 2-indanyl, (lower cycloalkyl)-(lower alkyl), (Het)-(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl;

or $R^3$ and $R^4$ together form a —($CH_2$)$_m$—W— group wherein m is the integer 2 or 3 and W is methylene or carbonyl, W being linked to the nitrogen atom bearing $R^5$; and $R^5$ is (1-8C)alkyl, phenyl(lower alkyl), phenyl-(lower alkyl) monosubstituted on the aromatic portion thereof with a halo, hydroxy, lower alkoxy or lower alkyl; 1-indanyl, 2-indanyl, (lower cycloalkyl)-(lower alkyl), (Het)-(lower alkyl) wherein Het is as defined hereinbefore, phenylsulfonyl, 1- or 2-naphthylsulphonyl, 5-(dimethylamino)-1-naphthylsulfonyl, (lower alkyl-amino) sulfonyl, {di(lower alkyl)amino}sulfonyl, (Het)-sulfonyl wherein Het is as defined hereinbefore, lower alkanoyl, (lower cycloalkyl)-(lower alkanoyl), {1-(lower alkyl)-(lower cycloalkyl)}carbonyl, (lower alkoxy)carbonyl, phenyl-Y-($CH_2$)$_n$C(O) wherein Y is oxy(—O—) or thio (—S—) and n is 0, 1 or 2 when Y is oxy or n is 1 or 2 when Y is thio, monosubstituted or disubstituted phenyl-Y-($CH_2$)$_2$C(O) wherein Y and n are as defined hereinbefore and the monosubstitution or disubstitution occurs on the phenyl portion thereof with a substituent selected from the group consisting of halo, hydroxy, lower alkoxy and lower alkyl; phenyl(lower alkanoyl), phenyl(lower alkanoyl) monosubstituted or disubstituted on the phenyl portion thereof with a substituent selected independently from the group consisting of azido, halo, hydroxy, lower alkoxy and lower alkyl; (Het)-($CH_2$)$_n$C(O) wherein Het and n are as defined hereinbefore, (Het)-Y-($CH_2$)$_n$C(O) wherein Het, Y and n are as defined hereinbefore, 2-{(lower alkoxycarbonyl)amino}-1-oxoethyl, (lower alkylamino)carbonyl, (di(lower alkyl) amino)carbonyl or (lower alkylamino)thiocarbonyl; or a therapeutically acceptable acid addition salt thereof; or Group 2 Compounds: A thiazolylphenyl derivative of formula G wherein R is as defined hereinbefore, and Z is $NR^{2A}$C (O)-A-$NR^{3A}R^{4A}$ wherein $R^{2A}$ is hydrogen or lower alkyl;

A is absent or carbonyl;

$R^{3A}$ is hydrogen, (1-8C)alkyl, 2-hydroxyethyl, 3-hydroxypropyl, (1-3C)alkyl monosubstituted with cyano, phenyl(lower alkyl), phenyl(lower alkyl) monosubstituted or disubstituted on the aromatic portion thereof with a halo, hydroxy, di(lower alkyl)amino, lower alkoxy or lower alkyl; (lower cycloalkyl)-(lower alkyl), or (Het)-(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl; and $R^{4A}$ is (1-8C) alkyl, phenyl(lower alkyl), phenyl-(lower alkyl) monosubstituted or disubstituted on the aromatic portion thereof with a halo, hydroxy, di(lower alkyl)amino, lower alkoxy or lower alkyl; 1-indanyl, 2-indanyl, phenyl(lower alkyl) monosubstituted on the aliphatic portion thereof with a hydroxy; (lower cycloalkyl)-(lower alkyl), Het as defined hereinbefore, (Het)-(lower alkyl) wherein Het is as defined hereinbefore or 3-1H-indolylmethyl;

or $R^{3A}$ and $R^{4A}$ together with the nitrogen to which they are attached form an unsubstituted, mono-substituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl; or $R^{3A}$ and $R^{4A}$ independently are:

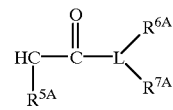

wherein L is carbon, oxygen or nitrogen, with the proviso that when L is oxygen, one of $R^{6A}$ or $R^{7A}$ is absent; $R^{5A}$ and $R^{6A}$ are independently selected from the group defined for $R^{3A}$ herein; and $R^{7A}$ is independently selected from the group defined for $R^{4A}$ herein; or therapeutically acceptable acid addition salt thereof; or Group 3 Compounds: A thiazolylphenyl derivative of formula G wherein R is as defined hereinbefore and Z is C(O)-$NR^{2B}R^{3B}$ wherein $R^{2B}$ is hydrogen, lower alkyl, lower alkenyl, lower alkynyl, phenyl(lower alkyl), phenyl(lower alkyl) monosubstituted or disubstituted on the aromatic portion thereof with a halo, hydroxy, lower alkoxy, lower alkyl or trifluoromethoxy; lower cycloalkyl, (lower cycloalkyl)-(lower alkyl), {1-hydroxy-(lower cycloalkyl}-(lower alkyl) or (Het)-(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl;2-benzimidazolylmethyl; and $R^{3B}$ is lower alkyl, phenyl(lower alkyl), phenyl(lower alkyl) monosubstituted or disubstituted on the aromatic portion thereof with a halo, hydroxy, lower alkoxy, lower alkyl or trifluoromethoxy; 1-indanyl, 2-indanyl, lower cycloalkyl, (lower cycloalkyl)-(lower alkyl), {1-hydroxy-(lower cycloalkyl)}-(lower alkyl) or (Het)-(lower alkyl) wherein Het is as defined hereinbefore;

or $R^{3B}$ is:

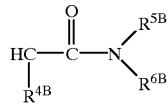

wherein $R^{4B}$ is hydrogen, lower alkyl, phenyl(lower alkyl), phenyl(lower alkyl) monosubstituted or disubstituted on the aromatic portion thereof with a halo, hydroxy, lower alkoxy, lower alkyl or tri-fluoromethoxy; (lower cycloalkyl)-(lower alkyl) or (Het)-(lower alkyl) wherein Het is as defined hereinbefore; $R^{5B}$ has the same significance as $R^{2B}$ hereinbefore and $R^{6B}$ has the same significance as defined for $R^{3B}$ hereinbefore; or $R^{3B}$ is $(CH_2)_tNR^{5B}R^{6B}$ wherein t is 1 or 2 and $R^{5B}$ and $R^{6B}$ are as defined hereinbefore; or $R^{3B}$ is $CH(R^7)CH_2OH$ wherein $R^{7B}$ has the same significance as $R^{4B}$ herein; or $R^{2B}$ and $R^{3B}$ together with the nitrogen to which they are attached form an unsubstituted, mono-substituted or disubstituted five or six membered, monovalent heterocyclic ring containing one or two heteroatoms selected from the group consisting of N, O or S, wherein each substituent is selected independently from the group consisting of halo, hydroxy, lower alkoxy, lower alkyl, phenyl(lower alkyl) and phenyl(lower alkyl) monosubstituted or disubstituted on the aromatic portion thereof with a halo, hydroxy, lower alkoxy or lower alkyl; with the proviso that when R is (lower alkoxycarbonyl)amino then $R^{2B}$ is hydrogen; or a therapeutically acceptable acid addition salt thereof; or Group 4 Compounds: A thiazolylphenyl derivative of formula G wherein R is as defined hereinbefore, and Z is $OCH_2C(O)NR^{2C}R^{3C}$ wherein $R^{2C}$ and $R^{3C}$ are independently hydrogen, lower alkyl, phenyl, phenyl(lower alkyl), phenyl(lower alkyl) monosubstituted or disubstituted on the aromatic portion thereof with a substituent selected independently from the group consisting of halo, hydroxy, lower alkoxy or lower alkyl; 1-indanyl, diphenylmethyl, lower cycloalkyl, (lower cycloalkyl)-(lower alkyl) or (Het)-(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl; with the provisos (a) that $R^{2C}$ and $R^{3C}$ cannot both be hydrogen, (b) that when R is hydrogen, methyl or dimethylamino then $R^{2C}$ and $R^{3C}$ cannot both be phenylmethyl, and (c) that when R is amino, then $R^{2C}$ and $R^{3C}$ cannot be the combination of hydrogen and 1,1-dimethylethyl or the combination of methyl and phenyl; or a therapeutically acceptable acid addition salt thereof; or Group 5 Compounds: A thiazolylphenyl derivative of formula G wherein R is as defined hereinbefore, and Z is $CH_2CH_2N(R^{2D})-C(O)R^{3D}$ wherein $R^{2D}$ is hydrogen, lower alkyl, phenyl(lower alkyl), phenyl(lower alkyl) monosubstituted or disubstituted on the aromatic portion thereof with a halo, hydroxy, lower alkoxy or lower alkyl; (lower cycloalkyl)-(lower alkyl), or (Het)-(lower alkyl) wherein Het represents an unsubstituted, monosubstituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl; and $R^{3D}$ is lower alkyl, lower alkyl monosubstituted, disubstituted or trisubstituted with a halo; phenyl unsubstituted, monosubstituted or disubstituted with a halo, hydroxy, lower alkoxy or lower alkyl; phenyl(lower alkyl) unsubstituted, monosubstituted or disubstituted on the aromatic portion thereof with a halo, hydroxy, lower alkoxy or lower alkyl; lower cycloalkyl, (lower cycloalkyl)-(lower alkyl), Het wherein Het is as defined hereinbefore, (Het)-(lower alkyl) wherein Het is as defined hereinbefore; lower alkylamino, di(lower alkyl)-amino, or phenyl(lower alkyl)amino unsubstituted, monosubstituted or disubstituted on the aromatic portion thereof with a halo, hydroxy, lower alkoxy or lower alkyl; or a therapeutically acceptable acid addition salt thereof.

With reference to greater detail, the five groups of thiazolylphenyl derivatives are described as follows:

Group 1: N-(Thiazolylphenyl)alkanamide Derivatives

According to one embodiment, the present application refers to Group 1 N-(thiazolylphenyl)alkanamide derivatives having antiherpes activity. The selective action of these compounds against these viruses, combined with a wide margin of safety, renders the compounds as desirable agents for combating herpes infections.

These N-(thiazolylphenyl)alkanamide derivatives can be characterized structurally by the presence of a N-{4-(4-thiazolyl)phenyl}amido moiety. Compounds possessing such a moiety have been reported previously, for example:

K. D. Hargrave et al., J. Med. Chem., 1983, 26, 1158;

C. G. Caldwell et al., U.S. Pat. No. 4,746,669, issued May 24, 1988;

A. Bernat et al., Canadian patent application 2,046,883, published Jun. 30, 1991;

A. Wissner, European patent application 458,037, published Nov. 27, 1991;

J. E. Macor and J. T. Nowakowski, PCT patent application WO 93/18032, published Sep. 16, 1993; and D. I. C. Scopes et al., UK patent application 2 276 164, published Sep. 21, 1994.

The present N-(thiazolylphenyl)alkanamide derivatives can be distinguished readily from the prior art compounds in that they possess different chemical structures and biological activities.

The Group 1 N-(thiazolylphenyl)alkanamide derivatives of this invention can also be represented by formula 1

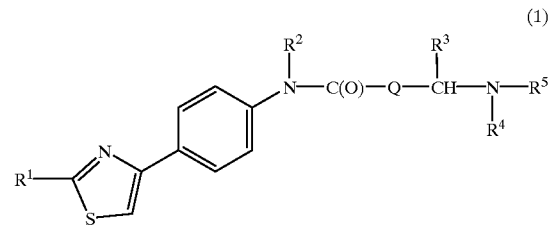

wherein $R^1$ has the same meaning as R as defined hereinbefore and $R^2$, Q, $R^3$, $R^4$ and $R^5$ are as defined hereinbefore.

A preferred set of Group 1 compounds of this invention is represented by Group 1-formula 1 wherein $R^1$ is selected from the group consisting of hydrogen, lower alkyl, amino, lower alkylamino, di(lower alkyl)amino, lower alkanoylamino, (lower alkoxycarbonyl)amino and ((lower alkylamino)carbonyl)amino; $R^2$ is hydrogen, methyl or ethyl; Q is absent or methylene; $R^3$ is hydrogen, lower alkyl, phenylmethyl or phenylmethyl substituted on the 4 position of the phenyl ring with halo, lower alkoxyl or lower alkyl; $R^4$ is hydrogen, (1-8C)alkyl, {di (lower alkyl)amino)-(lower alkyl), phenyl-(1-3C)alkyl, phenyl-(1-3C)alkyl monosubstituted on the aromatic portion thereof with halo, hydroxy, lower alkoxy or lower alkyl; 1-indanyl, 2-indanyl, (lower cycloalkyl)-(lower alkyl) or (Het)-lower alkyl wherein Het is as defined hereinbefore; or $R^3$ and $R^4$ together form a $CH_2CH_2$-W-group wherein W is as defined hereinbefore; and $R^5$ is (1-8C)alkyl, lower cyclohexyl, 1-pyrrolidinyl-ethyl, phenyl-(1-3C)alkyl, phenyl-(1-3C) alkyl monosubstituted on the aromatic portion thereof with halo, hydroxy, lower alkoxy or lower alkyl; 1-indanyl, 2-indanyl, (lower cycloalkyl)-(1-3C)alkyl, (Het)-(1-3C) alkyl wherein Het is as defined hereinbefore, phenylsulfonyl, 5-(dimethylamino)-1-naphthylsulfonyl, (lower alkylamino)sulfonyl, {di(lower alkyl) amino}sulfonyl, (Het)-sulfonyl wherein Het is as defined hereinbefore, lower alkanoyl, (lower cycloalkyl)-(lower alkanoyl), (1-methylcyclohexyl)carbonyl, (lower alkoxy) carbonyl, (phenylmethoxy)carbonyl, 2-phenoxyacetyl, 2-phenoxyacetyl monosubstituted or disubstituted on the phenyl ring with a substituent selected independently from the group consisting of bromo, chloro, fluoro, iodo, methoxy and methyl; phenyl-(1-3C)alkanoyl, phenyl-(1-3C)alkanoyl monosubstituted or disubstituted with a substituent selected independently from the group consisting of azido, bromo, chloro, fluoro, iodo, methoxy and methyl; (Het)-$(CH_2)_n$C(O) wherein Het and n are as defined hereinbefore, (Het)-Y-$(CH_2)_n$C(O) wherein, Het, Y and n are as defined hereinbefore, 2-{(lower alkoxy-carbonyl)amino}-1-oxoethyl, (lower alkylamino)-carbonyl, {di(lower alkyl) amino}carbonyl or (lower alkylamino)thiocarbonyl; or a therapeutically acceptable acid addition salt thereof.

A more preferred set of Group 1 compounds is represented by Group 1-formula 1 wherein $R^1$ is hydrogen, amino, methyl, methylamino, dimethylamino, acetylamino, (1,1-dimethylethoxycarbonyl)amino or {(1,1-dimethylethylamino)carbonyl}amino; $R^2$ is hydrogen or methyl; Q is absent or methylene; $R^3$ is hydrogen, methyl or phenylmethyl; $R^4$ is hydrogen, methyl, ethyl, propyl, butyl, 2-methylpropyl, 2,2-dimethylpropyl, 1-propylbutyl, 2-(dimethylamino)-ethyl, phenylmethyl, 1(R)-phenylethyl, 1(S)-phenylethyl, 2-phenylethyl, (4-chlorophenyl)methyl, (2-fluorophenyl)methyl, (3-fluorophenyl)methyl, (4-fluorophenyl)methyl, (4-methoxyphenyl)methyl, (2-methylphenyl)methyl, 1-indanyl, 2-indanyl, cyclopentylmethyl, cyclohexylmethyl, 1(S)-cyclohexyl-ethyl, 2-cyclohexylethyl, 2-(4-morpholinyl)ethyl, 2-pyridinylmethyl, 3-pyridinylmethyl, 4-pyridinyl-methyl, 2-(2-pyridinyl)ethyl, 2-(3-pyridinyl)ethyl, 2-(4-pyridinyl) ethyl, 2-thienylmethyl or 3-thienylmethyl; and $R^5$ is methyl, ethyl, propyl, butyl, 2,2-dimethylpropyl, 1-propylbutyl, cyclohexyl, 1-pyrrolidinylethyl, phenylmethyl, 1(R)-phenylethyl, 1(S)-phenylethyl, 2-phenylethyl, (4-chlorophenyl)methyl, (2-fluorophenyl)methyl, (3-fluorophenyl)methyl, (4-fluorophenyl)methyl, (2-hydroxyphenyl)methyl, 4-(methoxyphenyl)methyl, (2-methylphenyl)methyl, 1-indanyl, 2-indanyl, cyclopentylmethyl, cyclohexyl-methyl, 2-cyclohexylethyl, 2-(4-morpholinyl)ethyl, 2-pyridinylmethyl, 3-pyridinylmethyl, 4-pyridinyl-methyl, 2-thienylmethyl, phenylsulfonyl, 5-(dimethylamino)-1-naphthylsulfonyl, (dimethylamino)-sulfonyl, 4-morpholinylsulfonyl, acetyl, 2-methyl-propionyl, 2,2-dimethylpropionyl, 3,3-dimethyl-butyryl, cyclopentylcarbonyl, cyclohexylcarbonyl, cycloheptylcarbonyl, cyclopentylacetyl, cyclohexyl-acetyl, cycloheptylacetyl, (1-methylcyclohexyl)-carbonyl, (1-methylethoxy)carbonyl, (1,1-dimethylethoxy)carbonyl, (2-methylpropoxy)carbonyl, (phenylmethoxy)carbonyl, (2-phenoxy)acetyl, 2-( 4,6-dimethylphenoxy)acetyl, benzoyl, phenylacetyl, (4-azidophenyl)carbonyl, (2-fluorophenyl)carbonyl, (3-fluorophenyl)carbonyl, (4-fluorophenyl)carbonyl, (2,6-dimethylphenyl)carbonyl, 4-(1-methylpiperidinyl)carbonyl, 2-(4-imidazolyl)acetyl, 2-pyridinylcarbonyl, 3-pyridinylcarbonyl, 4-pyridinylcarbonyl, N-oxido-4-pyridinylcarbonyl, 2-pyridinylacetyl, 4-pyridinylacetyl, 6-(2,4-dihydroxypyrimidinyl)carbonyl, 2-pyrazinylcarbonyl, 2-thienylcarbonyl, 3-thienylcarbonyl, 4-morpholinylcarbonyl, 4-piperidinylcarbonyl, 2-(2-pyrimidinylthio)acetyl, 2-(4,6-dimethyl-2-pyrimidinylthio) acetyl, 4-{1-(1,1-dimethylethoxy)piperidinyl}carbonyl, 2-{(1,1-dimethylethoxycarbonyl)amino}-1-oxoethyl, (1,1-dimethylethylamino)carbonyl, (N,N-dibutylamino)-carbonyl, {N-methyl-N-(1,1-dimethylethyl)amino}-carbonyl, or (1,1-dimethylethylamino)thiocarbonyl; or $R^3$ and $R^4$ together form a $CH_2CH_2CH_2$ group and $R^5$ is butyl, 2,2-dimethylpropyl, 1-propylbutyl, benzyl, 1(R)-phenylethyl, 1(S)-phenylethyl, 2-phenylethyl, acetyl, 2-methylpropionyl, 2,2-dimethylpropionyl, 3,3-dimethylbutyryl, cyclopentylcarbonyl, cyclohexylcarbonyl, cycloheptylcarbonyl, cyclopentylacetyl, cyclohexylacetyl, cycloheptylacetyl, (1-methylcyclohexyl) carbonyl, (1-methylethoxy) carbonyl, (1,1-dimethylethoxy)carbonyl, (2-methylpropoxy)carbonyl or benzoyl, or $R^3$ and $R^4$ together form a $CH_2CH_2$C(O) group (wherein C(O) is linked to the adjoining nitrogen atom), and $R^5$ is butyl, phenylmethyl, 1(R) -phenylethyl, 1(S)-phenylethyl, 2-phenylethyl, cyclopentylmethyl, cyclohexylmethyl or 2-cyclohexylethyl; or a therapeutically acceptable acid addition salt thereof.

A most preferred set of Group 1 compounds is represented by Group 1-formula 1 wherein $R^1$ is hydrogen, amino, methylamino or dimethylamino; $R^2$ is hydrogen or methyl; Q is absent; $R^3$ is hydrogen, methyl or phenylmethyl; $R^4$ is methyl, phenylmethyl, 1(R)-phenylethyl, 1(S)-phenlylethyl, 2-phenylethyl, (4-chlorophenyl) methyl, (2-fluorophenyl) methyl, (4-fluorophenyl)methyl, (4-methoxyphenyl)methyl, (2-methylphenyl)methyl, 2-pyridinylmethyl, 3-pyridinylmethyl, 4-pyridinyl-methyl, 2-(2-pyridinyl)ethyl or 2-thienylmethyl; and $R^5$ is 2,2-dimethylpropionyl, 3,3-dimethylbutyryl, cyclopentylcarbonyl, cyclohexylcarbonyl, cycloheptylcarbonyl, cyclopentylacetyl, cyclohexylacetyl, (1-methylcyclohexyl)carbonyl, (1,1-dimethylethoxy) carbonyl, (2-methylpropoxy)carbonyl, benzoyl, (4-fluorophenyl)carbonyl, (2,6-dimethylphenyl)carbonyl, 2-pyridinylcarbonyl, 3-pyridinylcarbonyl, 4-pyridinylcarbonyl, 4-morpholinylcarbonyl or (1,1-dimethylethylamino)carbonyl; and the carbon atom bearing the $R^3$ group when $R^3$ is methyl or phenylmethyl has the (R) or (S) configuration; or $R^3$ and $R^4$ together form a $CH_2CH_2CH_2$ group and $R^5$ is cyclohexylcarbonyl, and the carbon atom bearing $R^3$ (i.e the carbon atom linked to the $CH_2CH_2CH_2$ group) has the (S) or (R) configuration; or a therapeutically acceptable acid addition salt thereof.

Still another set of most preferred Group 1 compounds is represented by Group 1-formula 1 wherein $R^1$ is amino, methylamino, dimethylamino, acetylamino, (1,1-dimethylethoxy)carbonylamino or {1,1-dimethylethylamino)carbonyl}amino; $R^2$ is hydrogen; Q is absent or methylene; $R^3$ is hydrogen or phenylmethyl; $R^4$ is hydrogen, methyl, 2,2-dimethylpropyl, phenylmethyl, 1(R)- phenylethyl, 1(S)-phenylethyl, 2-phenylethyl, (4-chlorophenyl)methyl, (2-methylphenyl)methyl, 1-indanyl, 2-indanyl, cyclohexylmethyl, 2-pyridinylmethyl, 3-pyridinylmethyl, 4-pyridinylmethyl, 2-(2-pyridinyl)ethyl or 2-thienylmethyl; and $R^5$ is methyl, phenylmethyl, (2-fluorophenyl)methyl, (4-fluorophenyl)methyl,(2-hydroxyphenyl)methyl, 4-morpholinylsulfonyl, 2,2-dimethylpropionyl, 3,3-dimethylbutyryl, cyclopentylcarbonyl, cyclohexylcarbonyl, cycloheptylcarbonyl, cyclopentylacetyl, cyclohexylacetyl, (1,1-dimethylethoxy)carbonyl, (2-methylpropoxy)carbonyl, (2-phenoxy)acetyl, 2-(2,6-dimethylphenoxy)acetyl, benzoyl, phenylacetyl, 2-pyridinylcarbonyl, 3-pyridinylcarbonyl, 4-pyridinylcarbonyl, 2-pyridinylacetyl, 4-morpholinylcarbonyl, 2-thienylcarbonyl, 2-thienylacetyl, {(1,1-dimethyl-ethyl)amino}carbonyl, ((1,1-dimethyl-ethyl)amino)thiocarbonyl or 2-(4,6-dimethyl-2-pyrimidinylthio)acetyl; and the carbon atom bearing the $R^3$ group when $R^3$ is phenylmethyl has the (R) or (S) configuration; or $R^3$ and $R^4$ together form a $CH_2CH_2CH_2$ group and $R^5$ is cyclohexylcarbonyl or benzoyl, and the carbon atom linked to the $CH_2CH_2CH_2$ group has the (R) or (S) configuration; or $R^3$ and $R^4$ together form a $CH_2CH_2C(O)$ group (wherein C(O) is linked to the adjoining nitrogen atom), and $R^5$ is phenylmethyl or cyclohexylmethyl, and the carbon linked to the terminal methylene of the $CH_2CH_2C(O)$ group has the (R) or (S) configuration; or a therapeutically acceptable acid addition salt thereof.

Included within the scope of this invention is a pharmaceutical composition comprising an antiherpes virally effective amount of a compound of Group 1 as defined herein, or a therapeutically acceptable acid addition salt thereof, and a pharmaceutically or veterinarily acceptable carrier.

Still another aspect of this invention involves a method for treating acyclovir-resistant herpes infections in a mammal which comprises administering to the mammal an anti-acyclovir-resistant herpes effective amount of a compound of Group 1 as defined herein, or a therapeutically acceptable acid addition salt thereof.

Process for preparing compounds of Group 1

The compounds of Group 1 can be prepared by a variety of processes. Description of some such methods are found in standard textbooks such as "Annual Reports In Organic Synthesis—1994", P. M. Weintraub et al., Eds., Academic Press, Inc., San Diego, Calif., USA, 1994 (and the preceding annual reports), "Vogel's Textbook of Practical Organic Chemistry", B. S. Furniss et al., Eds., Longman Group Limited, Essex, UK, 1986, and "Comprehensive Organic Synthesis", B. M. Trost and I. Fleming, Eds., Pergamon Press, Oxford, UK, 1991, Volumes 1 to 8.

One general process is represented by Group 1-scheme 1:

Group 1 - Scheme 1

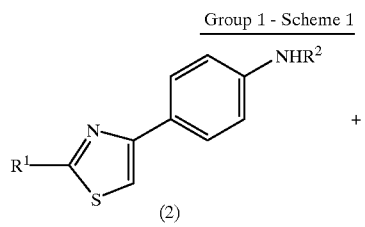

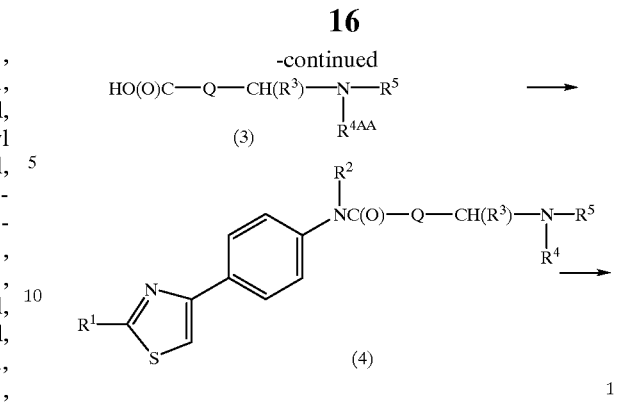

wherein $R^1$, $R^2$, Q, $R^3$ and $R^5$ are as defined herein and $R^{4AA}$ is an amino protecting group or a radical as defined for $R^4$ hereinbefore other than hydrogen.

According to Group 1-scheme 1, a thiazolylaniline derivative of formula 2 is coupled with an amino acid derivative of formula 3 to give a corresponding aminoamide of formula 4. In the instance where $R^{4AA}$ has the same significance as $R^4$ but excluding hydrogen, then the aminoamide of formula 4 so obtained is a compound of Group 1-formula 1. In the instance where $R^{4AA}$ is an amino protecting group, the compound of formula 4 so obtained can be deprotected to give the corresponding compound of Group 1-formula 1 in which $R^4$ is hydrogen. The latter product, albeit a compound of Group 1-formula 1, can also serve as an intermediate for further elaboration by standard methods to yield compounds of Group 1-formula 1 in which $R^4$ is other than hydrogen.

The coupling of the 4-thiazolylaniline derivative of formula 2 and the amino acid of formula 3 is effected by the classical dehydrative coupling of a free carboxyl of one reactant with the free amino group of the other reactant in the presence of coupling agent to-form a linking amide bond. Description of such coupling agents are found in general textbooks on peptide chemistry; for example, M. Bodanszky, "Peptide Chemistry", 2nd rev ed, Springer-Verlag, Berlin, Germany, 1993. Examples of suitable coupling agents are N,N'-dicyclohexylcarbodiimide, 1-hydroxybenzotriazole in the presence of N,N'-dicyclohexylcarbodiimide or N-ethyl-N'-((3-dimethylamino)propyl)carbodiimide. A very practical and useful coupling agent is the commercially available (benzotriazol-1-yloxy)tri-(dimethylamino)phosphonium hexafluorophosphate, either by itself or in the presence of 1-hydroxybenzotriazole. Still another very practical and useful coupling agent is commercially available 2-(1H-benzotriazol-1-yl)-N,N,N',N'-tetramethyl-uronium tetrafluoroborate.

The coupling reaction is conducted in an inert solvent, e.g. dichloromethane, dimethylformamide, tetrahydrofuran or acetonitrile. An excess of a tertiary amine, e.g. diisopropylethylamine or N-methylmorpholine, is added to maintain the reaction mixture at a pH of about eight. The reaction temperature usually ranges between 0° and 50° C. and the reaction time usually ranges between 15 minutes and 24 hours.

A practical and convenient variation of the preceding process (Group 1-scheme 1) can be practiced by replacing the 4-thiazolylaniline derivative 2 with 4'-aminoacetophenone. This process is illustrated by Group 1-scheme 2:

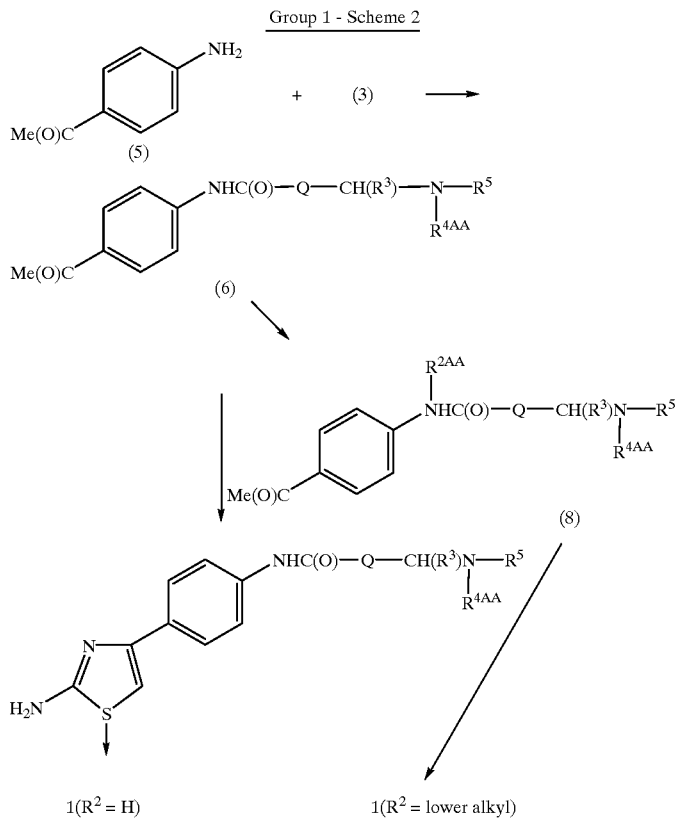

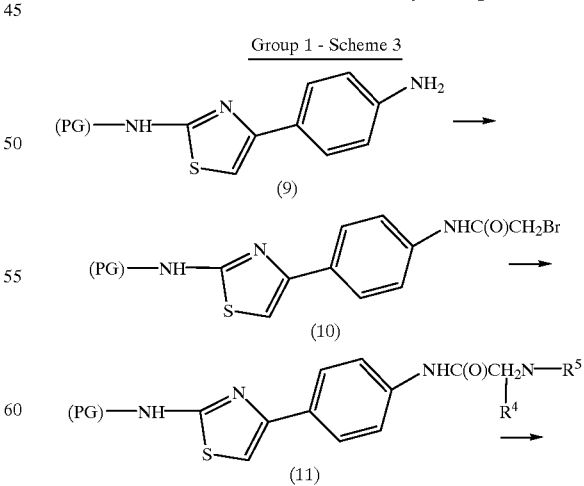

wherein $R^{2AA}$ is lower alkyl and $R^3$, $R^{4AA}$, $R^5$ and Q are as defined hereinbefore.

In Group 1-scheme 2, the compound of formula 5, namely 4'-aminoacetophenone, is coupled with amino acid derivative of formula 3, noted hereinbefore, to give a corresponding terminal methyl ketone of formula 6.

The methyl ketone 6 can be used to prepare compounds of Group 1-formula 1 wherein $R^2$ is hydrogen as follows: The methyl ketone was reacted with thiourea and iodine according to the method of R. M. Dodson and L. C. King, J. Amer. Chem Soc. 1945, 67, 2242 to give the corresponding aminothiazole derivative of formula 7. In the instance where $R^{4AA}$ has the same significance as $R^4$ but excluding hydrogen, then the aminothiazole derivative of formula 7 so obtained is a compound of Group 1-formula 1. In the instance where $R^{4AA}$ is an amino protecting group then the derivative of formula 7 so obtained can be deprotected to give a corresponding compound of Group 1-formula 1 wherein $R^4$ is hydrogen. If desired, the latter derivative can be converted by standard methods (e.g., N-alkylation, acylation, carbamate formation, etc.) with the appropriate agent to give corresponding compounds of formula 1 wherein $R^4$ is as defined hereinbefore other than hydrogen.

Alternately, the methyl ketone of formula 6 can be used to prepare compounds of Group 1-formula 1 wherein $R^2$ is lower alkyl. Accordingly, the methyl ketone of formula 6 is subjected to N-alkylation with an appropriate lower alkyl bromide, chloride or iodide in the presence of a base to give the corresponding N-alkylated derivative of formula 8 wherein $R^{2AA}$ is lower alkyl and Q, $R^3$, $R^{4AA}$ and $R^5$ are as defined hereinbefore. The latter compound, when $R^{4AA}$ is a radical as defined for $R^4$ of the compound of formula 1 other than hydrogen, can be transformed directly to the corresponding compound of Group 1-formula 1, wherein $R^1$ is amino, $R^2$ is lower alkyl, $R^4$ is a radical other than hydrogen and Q, $R^3$ and $R^5$ are as defined hereinbefore. The transformation is effected by employing the previously noted method of Dodson and King for aminothiazole formation. On the other hand, the N-alkylated derivative of formula 8 wherein $R^{4AA}$ is an amino protected group can be deprotected to give the corresponding compounds of Group 1-formula 1 wherein $R^1$ is amino, $R^2$ is lower alkyl, $R^4$ is hydrogen, and Q, $R^3$ and $R^5$ are as defined hereinbefore.

Still another variation is illustrated by Group 1-scheme 3:

1 ($R^1$ is $NH_2$, $R^2$ and $R^3$ each is H, Q is absent and $R^4$ and $R^5$ are defined herein)

wherein PG is an amino protecting group, $R^1$ is amino, $R^2$ and $R^3$ each is hydrogen, Q is absent and $R^4$ and $R^5$ are as defined hereinbefore.

According to Group 1-scheme 3, the protected aminothiazole derivative of formula 9 wherein PG represents an amino acid protecting group is reacted with bromoacetyl bromide to give the corresponding bromoacetamide 10. Displacement of the bromine of the latter compound with the appropriate primary or secondary amine gives the corresponding intermediate of formula 11. Removal of the protecting group PG from the latter intermediate gives the desired compound of Group 1-formula 1.

Still another variation, which can be used for preparing compounds of Group 1-formula 1 in which Q is methylene, is the process represented by Group 1-scheme 4:

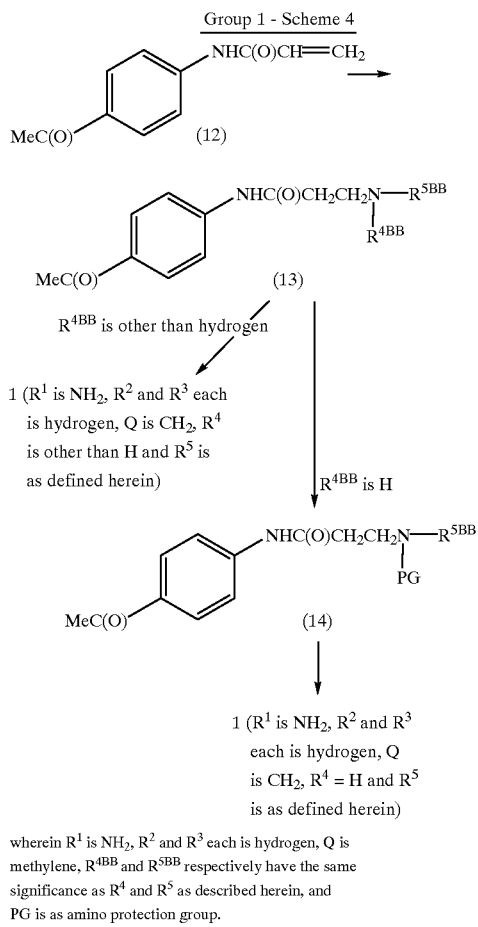

wherein $R^1$ is $NH_2$, $R^2$ and $R^3$ each is hydrogen, Q is methylene, $R^{4BB}$ and $R^{5BB}$ respectively have the same significance as $R^4$ and $R^5$ as described herein, and PG is as amino protection group.

According to Group 1-scheme 4, N-(4-acetylphenyl)-2-propenamide is reacted with the appropriate primary or secondary amine to give the Michael adduct of formula 13 wherein $R^{4BB}$ and $R^{5BB}$ respectively have the same significance as defined for $R^4$ and $R^5$ hereinbefore. Thereafter, the Michael adduct of formula 13 wherein $R^{4BB}$ is other than hyrogen is transformed to corresponding compounds of Group 1-formula 1 by the previously noted method of Dodson and King for aminothiazole formation. However, in the instance wherein $R^{4BB}$ of the Michael adduct is hydrogen, the transformation to corresponding compounds of Group 1-formula 1 proceeds with protecting the inherent secondary amine with an amino protecting group and the resulting amino protected derivative of formula 14 then is subjected to the Dodson and King method of aminothiazole formation, whereby the amino protecting group is cleaved in situ and the corresponding compound of Group 1-formula 1 wherein $R^4$ is hydrogen is obtained. If desired, the compounds of Group 1-formula 1 so obtained according to Group 1-scheme 4 can also serve as intermediates for elaboration to other compounds of Group 1-formula 1 in which Q is methylene by conventional methods.

The amino acid derivative of formula 3, noted in Group 1-schemes 1 and 2, can be prepared readily by methods used in peptide chemistry. For example, the N-monosubstituted and N,N-disubstituted glycine derivatives of formula 3, wherein Q is absent, can be prepared by substituting the bromine of the appropriate ethyl bromoacetate with an appropriate primary or secondary amine in the presence of a tertiary amine for example, triethylamine or N-methylmorpholine, to obtain the corresponding α-aminoester having either a monosubstituted or disubstituted amino group. Subsequent hydrolysis with lithium hydroxide of the latter product (or an amino protected derivative thereof in the process involving the primary amine), gives the desired protected N-monosubstituted, or the desired N,N-disubstituted amino acid derivative of formula 3 wherein Q is absent. Likewise, N,N-disubstituted β-amino acids of formula 3, wherein Q is methylene, can be prepared by a similar process wherein the ethyl bromoacetate derivative is replaced with the appropriate 3-bromopropionic ethyl ester derivative.

Examples of amino protective groups suitable for use in the above schemes include benzyloxycarbonyl, tert-butoxycarbonyl, 4-methoxybenzyloxycarbonyl or 2,2,2-trichloroethoxycarbonyl.

Other starting materials for the preceding processes are known or they can readily be prepared by standard methods from known starting materials. For example, 4'-aminoacetophenone (5) is available from the Aldrich Chemical Co., Milwaukee, Wis., USA; and the requisite thiazolylaniline derivatives of formula 2 can be obtained by applying the classical thiazole preparation involving reacting the appropriate thioamide or thiourea of formula $H_2N-C(S)-R^1$ wherein $R^1$ is hydrogen, amino, lower alkylamino or di(lower alkyl)amino with 2-bromo- 4'-nitroacetophenone (Aldrich Chemical Co.) according to method described by R. H. Wiley et al., Organic Reactions 1951, 6, 369–373 followed by reducing the intermediate product (with a nitro group) with iron powder in the presence of hydrochloric acid to obtain the desired thiazolylaniline derivative of formula 2 wherein $R^1$ is as defined in the last instance. Moreover, the preparation of N-(4-acetylphenyl)-2-propenamide (12) of Group 1-scheme 4 is described in example 8 herein; and the preparation of an example of the versatile starting material of formula 9 of Group 1-scheme 3 (wherein PG is tert-butoxycarbonyl) is given in example 1 herein.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, the reaction can be successfully performed by conventional modification known to those skilled in the art, e.g. by appropriate protection of interfering groups, by changing to alternative conventional reagents, by routine modification of reaction conditions, or by modification illustrated in the examples herein. Furthermore, if desired, the compound of Group 1-formula 1 can be obtained in the form of a therapeutically acceptable acid addition salt. Such salts can be considered as biological equivalent of the compounds of Group 1-formula 1. Examples of such salts are those formed with hydrochloric acid, sulfuric acid, phosphoric acid, formic acid, acetic acid or citric acid.

Antiherpes Activity

The antiviral activity of the compounds of Group 1-formula 1 can be demonstrated by biochemical, microbiological and biological procedures showing the inhibitory effect of the compounds on the replication of herpes simplex viruses, types 1 and 2 (HSV-1 and HSV-2), cytomegalovirus, as well as acyclovir-resistant herpes simplex viruses and ganciclovir-resistant cytomegaloviruses.

A biochemical procedure for demonstrating antiheroes activity for compounds of Group 1-formula 1 is described in the Group 1 examples hereinafter (see, for instance, Group 1, example 16). This particular assay is based on the evaluation of the ability of the test compound to inhibit HSV-1 helicase-primase, an essential enzyme for viral DNA replication.

Methods for demonstrating the inhibitory effect of the compounds of Group 1-formula 1 on herpes viral replication involving in vitro and cell culture techniques are desribed in example 16 herein.

The therapeutic effect of the compounds of Group 1-formula 1 can be demonstrated in laboratory animals, for instance, the hairless mouse model for the topical treatment of cutaneous HSV-1 infections, P. H. Lee et al., International Journal of Pharmaceutics, 1993, 93, 139; the (HSV-2)-induced genitalis mouse model, R. W. Sidewell et al., Chemotherapy, 1990, 36, 58; and BALB/C mouse model infected with murine cytomegalovirus, D. L. Barnard et al., Antiviral Res., 1993, 22, 77, and J. Neyts et al., Journal of Medical Virology, 1992, 37, 67.

When a compound of Group 1-formula 1, or one of its therapeutically acceptable acid addition salts, is employed as an antiviral agent, it is administered orally, topically or systemically to warm-blooded animals, e.g. humans, pigs or horses, in a vehicle comprising one or more pharmaceutically acceptable carriers, the proportion of which is determined by the solubility and chemical nature of the compound, chosen route of administration and standard biological practice. For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier. For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of Group 1-formula 1 is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's The Science and Pratice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of Group 1-formula 1 is most desirably administered at a concentration level that will generally afford antivirally effective results without causing any harmful or deleterious side effects.

For oral administration, the compound or a therapeutically acceptable salt is administered in the range of 10 to 200 mg per kilogram of body weight per day, with a preferred range of 25 to 150 mg per kilogram.

With reference to topical application, the compound of Group 1-formula 1 is administered topically in a suitable formulation to the infected area of the body e.g. the skin, the eye, the genitalia or part of the oral cavity, in an amount sufficient to cover the infected area. The treatment should be repeated, for example, every four to six hours until lesions heal.

For ocular administration, the compound of Group 1-formula 1 is administered either topically or intraocularly (injection or implant) in a suitable preparation. For example, an implant containing the compound in a suitable formulation can be surgically placed in the posterior segment of the eye through a small incision.

With reference to systemic administration, the compound of Group 1-formula 1 is administered at a dosage of 10 mg to 150 mg per kilogram of body weight per day, although the aforementioned variations will occur. However, a dosage level that is in the range of from about 10 mg to 100 mg per kilogram of body weight per day is most desirably employed in order to achieve effective results.

Although the formulations disclosed hereinabove are indicated to be effective and relatively safe medications for treating herpes viral infections, the possible concurrent administration of these formulations with other antiviral medications or agents to obtain beneficial results also included. Such other antiviral medications or agents include the antiviral nucleosides, for example, acyclovir, penciclovir, famciclovir, valacyclovir and ganciclovir, and antiviral surface active agents or antiviral interferons such as those disclosed by S. S. Asculai and F. Rapp in U.S. Pat. No. 4,507,281, Mar. 26, 1985.

The following examples (Group 1 examples) further illustrate this invention. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts ($\delta$) are reported in parts per million. The concentrations for the optical rotations are expressed in grams of the compound per 100 mL of solution. Abbreviations or symbols used in the Group 1 examples include ATP: adenosine triphosphate; Boc: tert-butoxycarbonyl or 1,1-dimethylethoxycarbonyl; BOP: (benzotriazole-1-yloxy)tris-(dimethylamino)phosphonium hexafluoro-phosphate; Bu: butyl; DIPEA: diisopropylethylamine; DMAP: 4-(dimethylamino)pyridine; DMF: dimethyl-formamide; DMSO: dimethylsulphoxide; Et: ethyl; EtOAc: ethyl acetate; $Et_2O$: diethyl ether; $Et_3N$: triethylamine; MS (FAB) or FAB/MS: fast atom bombardment mass spectrometry; Hex: hexane; mAb: monoclonal antibody; Me: methyl; MeOH: methanol; PFU: plaque forming units; Ph: phenyl; Pr: propyl; TBTU: 2-(1H-benzotriazol-1-yl)-N,N,N',N'-tetramethyluronium tetrafluoroborate; TFA: trifluoroacetic acid; THF: tetrahydrofuran.

GROUP 1 EXAMPLES

Example 1 tert-Butyl N-{4-(4-Aminophenyl)-2-thiazolyl}-carbamate a) 2,2,2-Trichloroethyl N-{4-(2-amino-4-thiazolyl)-phenyl}carbamate: 2,2,2-Trichloroethyl chloroformate (72.3 mL, 0.52 mol) was added (5 min) to an ice cold suspension of 4'-aminoacetophenone (67.6 g, 0.50 mol) and pyridine (50.5 mL, 0.62 mol). The reaction mixture was stirred at 0° for 15 min and then at room temperature (20–22°) for 45 min. The solvent was removed under reduced pressure. $Et_2O$ (500 mL) and 1N aqueous HCl (500 mL) were added to the residue. The resulting solid was collected by filtration, washed with $H_2O$ (1 L) and $Et_2O$ (1 L), and dried over $P_2O_5$ in a desiccator under reduced pressure for 15 h to yield the expected carbamate (137.8 g, 89% yield). A mixture of the crude carbamate (137.8 g, 0.44 mol), thiourea (135.0 g, 1.77 mol) and $I_2$ (202.6 g, 0.80 mol) in isopropanol (670 mL) was heated at reflux for 18 h. The reaction mixture was cooled to room temperature and EtOAc (1 L) was added. The solution was successively washed with $H_2O$ (2×600 mL), saturated aqueous $NaHCO_3$ (2×1 L) and then $H_2O$ (2×1 L). A mixture of the organic layer and saturated aqueous 4N HCl (750 mL) was stirred vigorously at room temperature for 1.5 h. $Et_2O$ (~800 mL) and $H_2O$ (~300 mL) were added to the mixture to facilitate stirring. The suspension was filtered and the solid was washed with a 1:1 mixture of EtOAc and $Et_2O$ (2 L). The solid was suspended in 20% aqueous NaOH (1.2 L). The mixture was extracted with EtOAc. The EtOAc extract was washed with brine (700 mL), dried ($MgSO_4$) and concentrated under reduced pressure to yield 2,2,2-trichloroethyl N-{4-(2-amino-4-thiazolyl)phenyl}carbamate (117.7 g, 75% yield) as a pale yellow solid: $^1$H NMR (400 MHz, DMSO-$d_6$) δ10.18 (s, 1H), 7.74 (d, J=8.6 Hz, 2H), 7.51 (d, J=8.6 Hz, 2H), 7.01 (s, 2H) 6.88 (s, 1H), 4.95 (s, 2H); MS (FAB) m/z 366/368/370/372 (MH)$^+$.

b) The title compound: A solution of $(Boc)_2O$ (87.7 g, 0.40 mol) in $CH_2Cl_2$ and DMAP(4.08 g, 33.0 mmol) was added (10 min) to a cooled (0°) solution of the product of preceding section a) (117.7 g, 0.33 mol) and pyridine (135.0 mL, 1.67 mol) in THF (500 mL) and $CH_2Cl_2$ (1 L). The reaction mixture was stirred at room temperature for 15 h. The reaction mixture was diluted with EtOAc (1.5 L) and $Et_2O$ (1 L). The resulting solution was washed serially with $H_2O$ (1 L), 10% (w/v) aqueous citric acid (2×500 mL), 1N aqueous HCl (500 mL), $H_2O$, saturated aqueous $NaHCO_3$ (2×1 L) and brine (1 L), dried ($MgSO_4$) and concentrated under reduced pressure to give a pale yellow foam (163 g). The latter foam (160 g, 0.34 mol) was diluted in 1,4-dioxane (1.72 L). The solution cooled to 10°. Zn powder (224 g, 3.43 mol) and 1N aqueous HCl (3.4 L) were added to the cooled solution. The reaction mixture was mechanically stirred at room temperature for 1.5 h. The suspension was filtered. The collected material was washed with 1N aqueous HCl (~1 L). Aqueous 20% NaOH (2 L) was added to the filtrate (including the acidic wash). The resulting mixture was extracted with EtOAc (9 L total). The EtOAc extract was filtered through diatomaceous earth. The filtrate was washed with brine, dried ($MgSO_4$) and concentrated under reduced pressure. Purification by flash chromatography ($SiO_2$, EtOAc: Hex, 1:2 to 2:3) of the residue gave the title compound (48.3 g, 49% yield) as a pale yellow foam: $^1$H NMR (400 MHz, DMSO-$d_6$) δ11.40 (s, 1H), 7.52 (d, J=7.2 Hz, 2H), 7.12 (s, 1H), 6.57 (d, J=7.2 Hz, 2H), 5.20 (s, 2H), 1.48 (s, 9H); MS (FAB) m/z 292 (MH)$^+$.

Example 2

N-{4-(2-Amino-4-thiazolyl)phenyl}-2-((phenylmethyl)-amino) acetamide (1: $R^1$, $R^2$, $R^3$ and $R^4$=H, $R^5$=$CH_2Ph$ and Q=valance bond)

a) tert-Butyl N-(2-hydroxy-2-oxoethyl)-N-(phenylmethyl)carbamate: To a cold (−20°) suspension of 60% NaH (120 g, 3.00 mol) in THF (700 mL) was added (30 min) a solution of Boc-glycine (175 g, 1.00 mol) in THF (300 mL). Thereafter, benzyl bromide was added to the mixture. After 15 min, the cooling bath was removed. The reaction mixture was stirred at room temperature for 1 h and then heated at reflux for 16 h. The reaction mixture was cooled to 0°. $H_2O$ (~50 mL) was added dropwise over a 30 min period. After another 30 min, $H_2O$ (600 mL) was added. The mixture was washed with hexane (3×500 mL). 1N Aqueous HCl (1.3 L) was added slowly to the aqueous layer, followed by the addition of 4N aqueous HCl (300 mL). The aqueous solution was extracted with EtOAc (1.5 L) and then $CH_2Cl_2$ (3×500 mL). The combined organic layers were serially washed with $H_2O$ and brine, dried ($MgSO_4$, $Na_2SO_4$, charcoal), filtered through diatomaceous earth and concentrated under reduced pressure to give the title compound (241 g, 91% yield) as a pale yellow solid: Mp 94–97°; $^1$H NM (400 MHz, DMSO-$d_6$) δ10.5 (broad s, 1H), 7.23–7.33 (m, 5H), 4.40 (s, 2H), 3.80, 3.72 (2s, 2H), 1.38, 1.35 (2s, 9H); MS (FAB) m/z 266 (MH)+; Anal. Calcd for $C_{14}H_{19}NO_4$ (and accounting for water content, 0.58% w/w as determined by Karl Fisher analysis): C, 63.01; H, 7.26; N, 5.25. Found: C, 62.79; H, 7.14; N, 5.13.

b) tert-Butyl N-(2-{(4-acetylphenyl)amino}-2-oxoethyl}-N-(phenylmethyl)carbamate: Isobutyl chloroformate (35.1 g, 0.26 mol) was added (15 min) to an ice-cold solution of tert-butyl N-(2-hydroxy-2-oxoethyl)-N-(phenylmethyl) carbamate (65.0 g, 0.24 mol), described in preceding section a), and $Et_3N$ (31.0 g, 0.31 mol) in $CH_2Cl_2$ (610 mL). The mixture was stirred at 0° for 45 min. Solid 4'-aminoacetophenone (34.8 g, 0.26 mol) was added portion wise to the reaction mixture. The reaction mixture was stirred at 0° for 1.5 h and then at room temperature for 16 h. $H_2O$ (10 mL) was added. The resulting solution was concentrated under reduced pressure. The residue was dissolved in EtOAc (1 L). The solution was washed successively with 1N aqueous HCl (2×300 mL), a saturated aqueous solution of $NaHCO_3$ (2×300 mL) and brine (200 mL), dried ($MgSO_4$) and concentrated under reduced pressure. The resulting brownish solid was crystallized (EtOAc: Hex) to give the title compound (56.8 g, 61% yield) as a white solid: $^1$H NMR (400 MHz, $CDCl_3$) δ9.72 (broad s, 1H), 7.90 (d, J=8.6 Hz, 2H), 7.40–7.54 (m, 2H), 7.26–7.39 (m, 5H), 4.55 (s, 2H), 3.96 (s, 2H), 2.56 (s, 3H), 1.51 (s, 9H); MS (FAB) m/z 383 (MH)$^+$.

c) The title compound: A mixture of tert-butyl N-{2-{(4-acetylphenyl)amino}-2-oxoethyl}-N-(phenylmethyl) carbamate (50.0 g, 0.13 mol), described in preceding section b), thiourea (39.8 g, 0.52 mol) and $I_2$ (66.4 g, 0.26 mol) in isopropanol (520 mL) was heated at reflux for 2.5 h. EtOAc (50 mL) was added to the cooled mixture. The resulting solid was collected by filtration. The filtrate was concentrated under reduced pressure. EtOAc (500 mL) was added to the concentrate and another portion of solid was obtained by filtration. The combined solid portions were suspended in 5% aqueous $Na_2CO_3$. The mixture was stirred vigorously. EtOAc (2 L) was added and the two immiscible phases were separated. The aqueous phase was extracted with EtOAc (2×800 mL). The combined organic phases were washed with brine, dried ($MgSO_4$) and concentrated under reduced pressure. Purification by flash chromatography ($SiO_2$, $CHCl_3$:EtOH, 10:1) gave the title compound (26.3 g, 59% yield) as a pale yellow solid: M.p. 162–163°; $^1$H NMR (400 MHz, DMSO-$d_6$) δ9.83 (s, 1H), 7.72 (d, J=8.7 Hz, 2H), 7.61 (d, J=8.7 Hz, 2H), 7.31–7.38 (m, 4H), 7.24 (t, J=7.2 Hz, 1H), 7.00 (s, 2H), 6.88 (s, 1H), 3.75 (s, 2H), 3.28 (s, 2H); MS (FAB) m/z 339 (MH)+; Anal. Calcd for $C_{18}H_{18}N_4OS$: C, 63.88; H, 5.36; N, 16.55. Found: C, 63.59; H, 5.32; N, 16.48.

Example 3

N-(4-(2-Amino-4-thiazolyl)phenyl)-2-{(cyclohexylmethyl)amino}acetamide (1: $R^1$, $R^2$ $R^3$ and $R^4$=H, $R^5$=cyclohexylmethyl and Q=valance bond)

Method A a) tert-Butyl N-(cyclohexylmethyl)-N-(2-hydroxy-2-oxoethyl)carbamate: Ethyl 2-bromoacetate (1.67 g, 10.0 mmol) was added (5 min) to a solution of cyclohexanemethylamine (1.13 g, 10.0 mmol) and $Et_3N$ (2.78 mL, 20.0 mmol) in THF (20 mL) at 0°. The mixture was stirred at 0° for 30 min, allowed to warm to room temperature, stirred at room temperature for 1 h and then cooled to 0°. A solution of $(Boc)_2O$ (2.20 g, 10.1 mmol) in THF (~5 mL) was added (10 min) to the reaction mixture. The solution was stirred at 0° for 30 min and then at room temperature for 1.5 h. A solution of $LiOH.H_2O$ (1.68 g, 40.0 mmol) in $H_2O$ (20 mL) and MeOH (10 mL) was added to the reaction mixture. The mixture was stirred at room temperature for 2.5 h. Thereafter, the organic solvents were removed from the reaction mixture under reduced pressure. The residual aqueous solution was diluted with $H_2O$ (125 mL) and washed with a 1:1 mixture of $Et_2O$:Hex (4×100 mL). The aqueous layer was rendered acidic with solid citric acid (pH=3) and then extracted with EtOAc (3×100 mL). The EtOAc extract was washed with brine (2×50 mL), dried ($MgSO_4$) and concentrated under reduced pressure to give the title compound (2.09 g, 77% yield) as a white solid, which was used without further purification: $^1$H NMR (400 mHz, $CDCl_3$) δ 3.96, 3.90 (2 broad s, 2H), 3.11 (broad s, 2H), 1.66–1.70 (m, 5H), 1.47, 1.43 (2s, 9H), 1.13–1.25 (m, 4H), 0.91 (broad s, 2H); MS (FAB) m/z 272 (MH)+.

b) tert-Butyl N-{2-{(4-acetylphenyl)amino}-2-oxoethyl}-N-(cyclohexylmethyl)carbamate: To a solution of the product of preceding section a) (1.43 g, 5.30 mmol) and 4-aminoacetophenone (712 mg, 5.30 mmol) in acetonitrile (10.6 mL) was added TBTU (1.69 g, 5.30 mmol) and DIPEA (1.85 mL, 10.6 mmol). The reaction mixture was stirred at room temperature for 18 h. The mixture was diluted with EtOAc (200 mL). The resulting solution was washed with $H_2O$ (50 mL), saturated aqueous $NaHCO_3$ (50 mL), brine (50 mL), dried ($MgSO_4$) and concentrated under reduced pressure. Purification by flash chromatography ($SiO_2$, EtOAc:Hex, 1:1) of the residue gave the desired tert-butyl N-{2-{(4-acetylphenyl)amino}-2-oxoethyl}-N-(cyclohexyl-methyl)carbamate (0.72 g, 35% yield) as a white solid: $^1$H NMR (400 MHz, $CDCl_3$) δ9.19 (broad s, 1H), 7.93 (d, J=8.6 Hz, 2H), 7.58 (d, J=8.6 Hz, 2H), 7.26 (s, 1H), 3.97 (s, 2H), 3.19 (d, J=7.0 Hz, 2H), 2.57 (s, 3H), 1.61–1.69 (m, 5H), 1.50 (s, 9H), 1.16–1.22 (m, 4H), 0.93 (broad s, 2H).

c) The title compound: A mixture of the product of preceding section b) (720 mg, 1.85 mmol), thiourea (282 mg, 3.71 mmol) and $I_2$ (704 mg, 2.78 mmol) in isopropanol (10 mL) was heated at reflux for 15 h. The reaction mixture was poured into $H_2O$ (125 mL) and the resulting mixture was washed with $Et_2O$ (4×100 mL). The aqueous layer was rendered basic by addition of saturated aqueous $NaHCO_3$ and then extracted with EtOAc (2×100 mL). The combined EtOAc extracts were dried ($MgSO_4$) and concentrated under reduced pressure. The residue was purified by flash chromatography ($SiO_2$, $CH_2Cl_2$: MeOH, 15:1) to give the title compound of this example (355 mg, 56% yield) as a light yellow solid: M.p. 164–166°; $^1$H NMR (400 MHz, DMSO-$d_6$) δ9.79 (broad s, 1H), 7.72 (d, J=8.7 Hz, 2H), 7.60 (d, J=8.7 Hz, 2H), 7.00 (s, 2H), 6.88 (s, 1H), 3.25 (s, 2H), 2.37 (d, J=6.6 Hz, 2H), 1.61–1.78 (m, 5H), 1.35–1.45 (m, 1H), 1.11–1.25 (m, 3H), 0.85–0.94 (m, 2H); MS (FAB) m/z 345 (MH)+; Anal. Calcd for $C_{18}H_{24}N_4OS$: C, 62.76; H, 7.02: N, 16.26. Found: C, 62.63; H, 7.10; N, 16.26.

Method B a) tert-Butyl N-{4-(4-{(2-bromo-1-oxoethyl)amino}-phenyl}-2-thiazolyl)carbamate: To an ice-cold solution of 2-bromoacetyl bromide (10.1 g, 50.0 mmol), in $CH_2Cl_2$ (200 mL) was added (30 min) a solution of tert-butyl N-{4-(4-aminophenyl)-2-thiazolyl}carbamate (14.6 g, 50.0 mmol, described in example 1) and pyridine (4.04 mL, 50.0 mmol) in $CH_2Cl_2$ (50 mL). The reaction mixture was stirred at 0° for 30 min and then at room temperature for 30 min. The reaction mixture then was diluted with in EtOAc (1.5 L). The resulting mixture was washed successively with $H_2O$ (500 mL), 10% (w/v) aqueous citric acid (2×500 mL), brine (500 mL), saturated aqueous $NaHCO_3$ (500 mL) and brine (500 mL), then dried ($MgSO_4$) and filtered. The organic solution was concentrated under reduced pressure to a volume of 500 mL. The resulting suspension was filtered and the collected solid was washed with EtOAc (2×10 mL) to yield 13.1 g of the title compound. An additional 2.4 g was obtained by concentration of the filtrate to a volume of 25 mL giving a total of 15.5 g (75% yield) of the tert-butyl N-{4-{4-{(2-bromo-1-oxoethyl)amino)phenyl}-2-thiazolyl}carbamate as a white solid: $^1$H NMR (400 MHz, DMSO-$d_6$) δ11.54 (s, 1H), 10.44 (s, 1H), 7.82 (d, J=8.7 Hz, 2H), 7.62 (d, J=8.7 Hz, 2H), 7.46 (s, 1H), 4.04 (s, 2H), 1.49 (s, 9H); MS (FAB) m/z 412/414 (MH)+.

b) tert-Butyl N-{4-{4-{{2-{(cyclohexylmethyl)amino}-1-oxoethyl}amino}phenyl}-2-thiazolyl}carbamate: To an ice-cold solution of the product of preceding section a) (2.48 g, 6.00 mmol) in THF (60 mL) were added cyclohexanemethylamine (781 μL, 6.00 mmol) followed by $Et_3N$ (1.67 mL, 12.0 mmol). The reaction mixture was stirred at room temperature for 4 h. $H_2O$ (10 mL) and saturated aqueous $NaHCO_3$ (10 mL) were added to the mixture. The solvent was removed under reduced pressure. EtOAc (200 mL), $H_2O$ (30 mL), and saturated aqueous $NaHCO_3$ (30 mL) were added to the residual aqueous solution. The phases were separated. The organic phase was washed with $H_2O$. The solid in the suspension in the organic phase was collected on a filter. The solid was washed with $H_2O$ (10 mL) and EtOAc (10 mL) to give a first crop of product (2.55 g). The filtrate was concentrated to 25 mL and the resulting suspension filtered to afford a second crop of 0.60 g of product. In this manner, a total of 3.15 g (81% yield) of the title compound of this section b) was collected as a white solid: $^1$H NMR (400 MHz, DMSO-$d_6$) δ9.82 (broad s, 1H), 7.79 (d, J=8.7 Hz, 2H), 7.65 (d, J=8.7 Hz, 2H), 7.44 (s, 1H), 3.25 (s, 2H), 2.37 (d, J=6.6 Hz, 2H), 1.59–1.78 (m, 5H), 1.35–1.44 (m, 1H), 1.14–1.27 (m, 3H), 0.85–0.94 (m, 2H).

c) The title compound of this example: A solution of the product of preceding section b) (2.40 g, 5.40 mmol) and TFA (40 mL) in $CH_2Cl_2$ (40 mL) was stirred at room temperature for 2 h. The reaction mixture was concentrated under reduced pressure. The residue was dissolved in EtOAc (250 mL), the resulting solution was washed with saturated aqueous $NaHCO_3$ and brine, dried ($MgSO_4$) and concentrated under reduced pressure to give the title compound of this example (1.60 g, 86% yield) as a white solid. This material was found to be identical to the product prepared by method A of this example.

Example 4

N-{2-{{4-(2-Amino-4-thiazolyl)phenyl}amino}-2-oxoethyl}-N-(phenylmethyl)cyclohexanecarboxamide (1: $R^1$, $R^2$ and $R^3$=H, $R^4$=PhCH$_2$, $R^5$=cyclohexylcarbonyl and Q=valance bond)

To a solution of N-{4-(2-amino-4-thiazolyl)phenyl}-2-{(phenylmethyl)amino}acetamide (352 mg, 1.04 mmol, described in example 2), cyclohexanecarboxylic acid (140 mg, 1.09 mmol) and DIPEA (269 mg, 2.08 mmol) in DMF (5.2 mL) was added TBTU (350 mg, 1.09 mmol). The mixture was stirred at room temperature for 6 h. The reaction mixture was diluted with EtOAc (125 mL). The resulting solution was washed with saturated aqueous NaHCO$_3$ (40 mL), H$_2$O (40 mL), and brine (40 mL), then dried (MgSO$_4$) and concentrated under reduced pressure. The residue was purified by flash chromatography (SiO$_2$, CHCl$_3$: EtOH, 15:1) to yield the title compound (341 mg, 73% yield) as a white solid: M.p. 214.5–215.5°; $^1$H NMR (400 MHz, DMSO-d$_6$) δ (2 rotamers, 1:1) 10.06, 9.92 (2 s, 1H), 7.73, 7.71 (2 d, J=8.5 Hz, 2H), 7.56, 7.55 (2 d, J =8.5 Hz, 2H), 7.20–7.41 (m, 5H), 7.01, 7.00 (2 s, 2H), 6.89, 6.88 (2 s, 1H), 4.70, 4.51 (2 s, 2H), 4.13, 4.02 (2 s, 2H), 2.64, 2.56 (2 broad t, J=10.5 Hz, 1H), 1.61–1.70 (m, 5H), 1.12–1.46 (m, 5H); MS (FAB) m/z 449 (MH)$^+$; Anal. Calcd for C$_{25}$H$_{28}$N$_4$O$_2$S: C, 66.94; H, 6.29; N, 12.49. Found: C, 66.54; H, 6.29; N, 12.32.

Example 5

N-{2-{{4-(2-Amino-4-thiazolyl)phenyl}amino}-2-oxoethyl}-N'-(1,1-dimethylethyl)-N-(phenylmethyl)-urea (1: $R^1$, $R^2$ and $R^3$=H, $R^4$=PhCH$_2$, $R^5$=C(O)NHCMe$_3$ and Q=valance bond)

tert-Butyl isocyanate (114 mL, 1.00 mmol) was added dropwise to a solution of N-{4-(2-amino-4-thiazolyl) phenyl}-2-{(phenylmethyl)amino}-acetamide•2HCl (411 mg, 1.00 mmol, the corresponding free base has been described in example 2) and Et$_3$N (558 mL, 4.00 mmol) in THF (10 mL) and CH$_2$Cl$_2$ (10 mL) at room temperature. The reaction mixture was stirred 18 h. The mixture was diluted with EtOAc (200 mL). The resulting solution was washed with saturated aqueous NaHCO$_3$ (75 mL), brine (75 mL), dried (MgSO$_4$), and concentrated under reduced pressure. The pale yellow solid residue (450 mg) was recrystallized from EtOAc to give the title compound of this example (295 mg, 67%) as white crystals: M.p. 207–209°; $^1$H NMR (400 MHz, DMSO-d$_6$) δ9.89 (s, 1H), 7.72 (d, J=8.7 Hz, 2H), 7.55 (d, J=8.7 Hz, 2H), 7.23–7.36 (m, 5H), 6.98 (s, 2H), 6.88 (s, 1H), 5.80 (s, 1H), 4.50 (s, 2H), 3.96 (s, 2H), 1.25 (s, 9H); MS (FAB) m/z 438 (MH)$^+$; Anal. Calcd for C$_{23}$H$_{27}$N$_5$SO$_2$: C, 63.13; H, 6.22; N, 16.01. Found: C, 63.03; H, 6.24; N, 16.03.

Example 6

N-{2-{{4-(2-Amino-4-thiazolyl)phenyl}amino}-2-oxoethyl}-N-(phenylmethyl)-4-morpholinecarboxamide (1: $R^1$, $R^2$ and $R^3$=H, $R^4$=PhCH$_2$, $R^5$=4-morpholinylcarbonyl and Q=valance bond)

To a cooled (0°) suspension of N-{4-(2-amino-4-thiazolyl)phenyl}-2-{(phenylmethyl)amino)acetamide (1.02 g, 3.00 mmol, described in example 2) in CH$_2$Cl$_2$ (30 mL) and Et$_3$N (836 μL, 6.00 mmol), were added DMAP (36.6 mg, 0.30 mmol) and 4-morpholinecarbonyl chloride (350 μL, 3.00 mmol). The reaction mixture was stirred at 0° for 30 min, and then at room temperature for 18 h. The reaction mixture was then dissolved in EtOAc (300 mL). The resulting solution was washed with saturated aqueous NaHCO$_3$ (100 mL), brine (100 mL), then dried (MgSO$_4$), and concentrated under reduced pressure. The residue was purified by flash chromatography (SiO$_2$, EtOAc) to afford the title compound (925 mg, 68% yield) as a white solid: M.p. 1050 (decomp.); $^1$H NMR (400 MHz, DMSO-d$_6$) δ9.94 (s, 1H), 7.71 (d, J=8.7 Hz, 2H), 7.55 (d, J=8.7 Hz, 2H), 7.25–7.39 (m, 5H), 6.99 (s, 2H), 6.88 (s, 1H), 4.47 (s, 2H), 3.84 (s, 2H), 3.59 (t, J=4.9 Hz, 4H), 3.19 (t, J=4.9 Hz, 4H); MS (FAB) m/z 452 (MH)+; Anal. Calcd for C$_{23}$H$_{25}$N$_5$SO$_3$: C, 61.18; H, 5.58; N, 15.51. Found: C, 60.61; H, 5.60; N, 15.35.

Example 7

N-{4-(2-Amino-4-thiazolyl)phenyl}-2-{(4-morpholinylsulfonyl)(phenylmethyl)amino}acetamide (1: $R^1$, $R^2$ and $R^3$=H, $R^4$=PhCH$_2$, $R^5$=4-morpholinylsulfonyl and Q=valance bond)

4-Morpholinesulfonyl chloride (213 mg, 1.15 mmol) was added (5 min) to an ice-cold solution of N-{4-(2-amino-4-thiazolyl)phenyl}-2-{(phenylmethyl-amino}acetamide•2HCl (450 mg, 1.09 mmol), the corresponding free base has been described in example 2) and Et$_3$N (443 mg, 4.38 mmol) in CH$_2$Cl$_2$ (10.9 mL). The reaction mixture was allowed to warm to room temperature and DMAP (14.0 mg, 0.11 mmol) was added. After standing for 37 h at room temperature, the mixture was dissolved in EtOAc (125 mL). The solution was washed successively with saturated aqueous NaHCO$_3$ (50 mL) and brine (50 mL), dried (MgSO$_4$) and concentrated under reduced pressure. Purification of the resulting residue by flash chromatography (SiO$_2$, EtOAc) gave the title compound (200 mg, 38% yield) as a white solid: M.p. 193–194°; $^1$H NMR (400 MHz, DMSO-d$_6$) δ10.02 (s, 1H), 7.73 (d, J=8.7 Hz, 2H), 7.55 (d, J=8.7 Hz, 2H), 7.30–7.41 (m, 5H), 7.01 (s, 2H), 6.89 (s, 1H), 4.59 (s, 2H), 3.91 (s, 2H), 3.58 (t, J=4.6 Hz, 4H), 3.18 (t, J=4.6 Hz, 4H); MS (FAB) m/z 488 (MH)$^+$; Anal. Calcd for C$_{22}$H$_{25}$N$_5$O$_4$S$_2$: C, 54.19; H, 5.17; N; 14.36. Found: C, 53.63; H, 5.07; N, 14.34.

Example 8

N-{4- (2-Amino-4-thiazolyl)phenyl}-3-{(phenylmethyl)-amino}propanamide (1: $R^1$, $R^2$, $R^3$=H and $R^4$=H, $R^5$=PhCH$_2$ and Q=CH$_2$)

a) N-(4-Acetylphenyl)-2-propenamide: A solution of acryloyl chloride (29.5 mL, 363 mmol) in CH$_2$Cl$_2$ (50 mL) was added dropwise (30 min) to an ice-cold solution of 4'-aminoacetophenone (49.0 g, 363 mmol) and Et$_3$N (50.6 mL, 363 mmol) in CH$_2$Cl$_2$ (300 mL). The reaction mixture was stirred at 0° for 15 min and then was concentrated under reduced pressure. The residue was dissolved with EtOAc. The solution was washed successively with 10% aqueous HCl, saturated aqueous NaHCO$_3$ and H$_2$O. The organic phase was dried (MgSO$_4$) and concentrated under reduced pressure to afford the desired N-(4-acetylphenyl)-2-propenamide (52 g, 76% yield) as a yellow solid: $^1$H NMR (400 MHz, CDCl$_3$) δ8.17 (broad s, 1H), 7.93 (d, J=8.9 Hz, 2H), 7.72 (d, J=8.9 Hz, 2H), 6.47 (dd, J=1.0, 16.9 Hz, 1H), 6.33 (dd, J=10.2, 16.9 Hz, 1H), 5.80 (dd, J=1.0, 10.2 Hz, 1H), 2.58 (s, 3H); MS (FAB) m/z 190 (MH)$^+$.

b) N-(4-Acetylphenyl)-3-{(phenylmethyl)amino}-propanamide: A solution of the product of preceding section a) (2.00 g, 10.6 mmol) and benzylamine (1.27 mL, 11.6 mmol) in THF (50 mL) was heated at reflux for 25.5 h. The cooled mixture was concentrated under reduced pressure. The residue was dissolved with EtOAc. The EtOAc solution was washed with 10% aqueous HCl. The resulting solid was collected on a filter and then combined with the aqueous acidic phase. This acidic suspension was rendered basic (pH=~12) with 10N aqueous NaOH. The mixture was extracted with EtOAc. The EtOAc extract was dried ($MgSO_4$) and concentrated under reduced pressure to afford N-(4-acetylphenyl)-3-{(phenylmethyl)amino}propanamide (2.92 g) as a yellow oil which could be used directly in the next step or purified by flash column chromatography ($SiO_2$, EtOAc) to afford 2.05 g (65% yield) of a pale yellow solid: $^1$H NMR (400 MHz, $CDCl_3$) δ7.91 (d, J=11.1 Hz, 2H), 7.59 (d, J=11.1 Hz, 2H), 7.26–7.40 (m, 5H), 3.88 (s, 2H), 3.05 (dd, J=5.7, 6.7 Hz, 2H), 2.57 (s, 3H), 2.54 (dd, J =5.7, 6.7 Hz, 2H), 1.69 (s, 1H); MS (FAB) m/z 297 (MH)$^+$.

c) tert-Butyl N-{3-{(4-acetylphenyl)amino}-3-oxopropyl}-N-(phenylmethyl)carbamate: To a solution of the product of section b) (1.78 g, 5.99 mmol) and DIPEA (2.00 mL, 12.0 mmol) in THF (30 mL) was added $(Boc)_2O$ (1.23 g, 6.59 mmol). The resulting solution was stirred at room temperature for 18 h and then concentrated under reduced pressure. The residue was dissolved with EtOAc. The EtAOc solution was washed successively with 10% aqueous HCl, saturated aqueous $NaHCO_3$ and brine. The organic phase was dried ($MgSO_4$) and concentrated under reduced pressure. Purification of the residue by flash chromatography ($SiO_2$, EtOAc:Hex, 1:1) gave tert-butyl N-{3-{(4-acetylphenyl)amino}-3-oxopropyl}-N-(phenylmethyl) carbamate (2.33 g, 98% yield) as a white foam: $^1$H NNR (400 MHz, $CDCl_3$) δ9.20 (broad s, 1H), 7.92 (d, J=8.3 Hz, 2H), 7.68 (broad d, J=8.3 Hz, 2H), 7.22–7.35 (m, 5H), 4.47 (s, 2H), 3.62 (t, J=6.7 Hz, 2H), 2.64 (broad s, 2H), 2.57 (s, 3H), 1.46 (s, 9H); MS (FAB) ml/z 397 (MH$^+$).

d) The title compound: A solution of the product of preceding section c) (2.17 g, 5.47 mmol), thiourea (1.67 g, 21.9 mmol) and $I_2$ (2.78 g, 10.9 mmol) in isopropanol (11 mL) was heated at reflux for 5 h. The resulting suspension was cooled to room temperature and then filtered. The collected solid was suspended in a mixture of saturated aqueous $NaHCO_3$ (200 mL) and 1ON aqueous NaOH (1 mL). The suspension was extracted with EtOAc. The EtAOc extract was dried ($MgSO_4$) and concentrated under reduced pressure. The residue was purified by recrystallisation from EtOAc to afford the title compound (1.23 g, 64% yield) as a pale yellow solid: M.p. 131–133°; $^1$H NMR (400 MHz, DMSO-$d_6$) δ10.10 (s, 1H), 7.70 (d, J=8.6 Hz, 2H), 7.56 (d, J=8.6 Hz, 2H), 7.22–7.32 (m, 5H), 6.99 (s, 2H), 6.87 (s, 1H), 3.73 (s, 2H), 2.80 (broad s, 2H), 2.39 (broad s, 2H); MS (FAB) m/z 353 (MH)$^+$; Anal. Calcd for $C_{19}H_{20}N_4OS$: C, 64.75; H, 5.72; N, 15.90. Found: C, 63.95; H, 5.67; N, 15.92.

Example 9 tert-Butyl N-{2-{{4-{2-(Dimethylamino)-4-thiazolyl}phenyl}amino}-2-oxoethyl}-N-(phenylmethyl) carbamate (1: $R^1$=$NMe_2$, $R^2$ and $R^3$=H, $R^4$=$PhCH_2$, $R^5$=C (O)$OCMe_3$ and Q=valance bond)

a) N,N-Dimethyl-4-(4-nitrophenyl)-2-thiazolamine: A solution of 2-bromo-4-nitroacetophenone (4.42 g, 18.1 mmol), N,N,-dimethylthiourea (3.77 g, 36.2 mmol) in isopropanol (60 mL) was heated at reflux for 45 min. The cooled reaction mixture was diluted with EtOAc. The solution was washed with saturated aqueous $NaHCO_3$, $H_2O$ and brine, dried ($MgSO_4$) and concentrated under reduced pressure to give N,N-dimethyl-4-(4-nitrophenyl)-2-thiazolamine (2.92 g, 65% yield) as an orange solid: $^1$H NMR (400 MHz, DMSO-$d_6$) δ8.24 (d, J=8.8 Hz, 2H), 8.11 (d, J=8.8 Hz, 2H), 7.56 (s, 1H), 3.11 (s, 6H); MS (FAB) m/z 250 (MH)$^+$.

b) N,N-dimethyl-4-(4-aminophenyl)-2-thiazolamine: Iron powder (6.51 g, 116.7 mmol) and 1N aqueous HCl (2.3 mL) were added to a solution of N,N-dimethyl-4-(4-nitrophenyl)-2-thiazolamine of section a) (2.91 g, 11.7 mmol) in EtOH (39 mL) at room temperature. The mixture was stirred and heated at reflux for 3 h. The hot reaction mixture was filtered through diatomaceous earth. The solid on the filter was washed with hot EtOH (200 mL). The filtrate was diluted with EtOAc and $Et_2O$ (1:1, 100 mL) and then concentrated to about 25% of its original volume. This solution was diluted with EtOAc (150 mL). The mixture was washed successively with saturated aqueous $NaHCO_3$, $H_2O$ and brine, then dried ($MgSO_4$) and concentrated under reduced pressure to give N,N-dimethyl-4-(4-aminophenyl)-2-thiazolamine (2.24 g, 87% yield) as a light brown oil: $^1$H NMR (400 MHz, DMSO-$d_6$) δ7.53 (d, J=8.4Hz, 2H), 6.74 (s, 1H), 6.56 (d, J=8.4 Hz, 2H), 5.16 (s, 2H), 3.05 (s, 6H); MS (FAB) m/z 220 (MH)$^+$. This product was used without further purification in the next section.

c) The title compound: DIPEA (4.21 mL, 24.2 mmol) was added to a solution of N,N-dimethyl-4-(4-aminophenyl)-2-thiazolamine (1.77 g, 8.07 mmol, described in the previous section), tert-butyl N-(2-hydroxy-2-oxoethyl)-N-(phenylmethyl)carbamate {2.35 g, 8.87 mmol, described in example 2, section a)} and BOP (3.92 g, 8.87 mmol) in DMF (8 mL) at room temperature. The reaction mixture was stirred at room temperature for 2 h then diluted with EtOAc (300 mL). The solution was washed successively with $H_2O$ (2×60 mL), saturated aqueous $NaHCO_3$ (60 mL) and brine (60 mL), dried ($MgSO_4$) and concentrated under reduced pressure. Purification of the residue by flash chromatography ($SiO_2$, Hex:EtOAc:EtOH, 5:2:1) gave the title compound (3.13 g, 83% yield) as a beige solid: $^1$H NMR (400 MHz, DMSO-$d_6$) δ9.98, 9.92 (2s, 1H), 7.80 (d, J=8.4 Hz, 2H), 7.59 (d, J=8.4 Hz, 2H), 7.26–7.38 (m, 5H), 7.06 (s, 1H), 4.48 (s, 2H), 3.97, 3.86 (2s, 2H), 3.08 (s, 6H), 1.37 (s, 9H); MS (FAB) m/z 467 (MH)$^+$; Anal. Calcd for $C_{25}H_{30}N_4O_3S$: C, 64.35; H, 6.48; N, 12.01. Found: C, 64.54; H, 6.56; N, 12.12.

Example 10

N-{4-(2-Amino-4-thiazolyl)phenyl}-N-methyl-2-{(phenylmethyl)amino}acetamide (1: $R^1$=$NH_2$, $R^2$=$CH_3$, $R^3$=H, $R^4$=H and $R^5$=$PhCH_2$)

a) tert-Butyl N-{2-{(4-acetylphenyl)methylamino}-2-oxoethyl}-N-(phenylmethyl)carbamate: A solution of tert-butyl N-{2-{(4-acetylphenyl)amino}-2-oxoethyl}-N-(phenylmethyl)carbamate (1.50 g, 3.92 mmol), described in section b) of example 2, in DMF (5.5 mL) was added rapidly to a suspension of NaH (94 mg, 3.92 mmol) in DMF (10 mL) at room temperature. The mixture was stirred at room temperature for 30 min. Methyl iodide (366 mL, 5.88 mmol) was added to the solution. The reaction mixture was stirred at room temperature for 18 h. The mixture was diluted with $H_2O$ (100 mL) and the resulting solution was extracted with EtOAc (200 mL). The organic layer was washed with $H_2O$ (3×75 mL) and brine (75 mL), dried ($MgSO_4$) and concentrated under reduced pressure. The residue was purified by flash chromatography ($SiO_2$, Hex:EtOAc, 1:1) to give the title compound (0.80 g, 52% yield) as a colorless foam: $^1$H NMR (400 MHz, $CDCl_3$) δ7.94 (d, J=8.3 Hz, 2H), 7.15–7.30 (m, 7H), 4.53, 4.56 (2s, 2H), 3.59, 3.74 (2 broad s, 2H), 3.29 (s, 3H), 2.59 (s, 3H), 1.45, 1.47 (2s, 9H); MS (FAB) m/z 397 (MH)+.

b) The title compound: A solution of the product of preceding section a) (0.79 g, 1.99 mmol), thiourea (0.61 g, 7.97 mmol) and $I_2$ (1.01 g, 3.98 mmol) in isopropanol (5 mL) was heated at reflux for 2 h. The cooled mixture was partitioned between saturated aqueous $NaHCO_3$ and EtOAc (200 mL). The organic layer was washed with brine (50 mL), dried ($MgSO_4$) and concentrated under reduced pressure. Purification by flash chromatography ($SiO_2$, $CHCl_3$:EtOH, 8:1) yielded the title compound (358 mg, 51% yield) as a pale yellow solid: M.p. 160–2°; $^1$H NMR (400 MHz, DMSO-$d_6$) δ7.80 (d, J=8.4 Hz, 2H), 7.17–7.27 (m, 7 H), 7.06 (s, 2H), 7.05 (s, 1H), 3.61 (broad s, 2H), 3.19 (s, 3H), 3.04 (broad s, 2H), 2.33 (broad s, 1H); MS (FAB) m/z 353 (MH)+; Anal. Calcd for $C_{19}H_{20}N_4OS$: C, 64.75; H, 5.72; N, 15.90. Found: C, 64.46; H, 5.63; N, 15.80.

Example 11 tert-Butyl N-{2-{{4-(2-Amino-4-thiazolyl)phenyl}-amino}-2-oxo-1(S)-(phenylmethyl)ethyl}carbamate (1: $R^1=NH_2$, $R^2=H$, $R^3=PhCH_2$, $R^4=H$ and $R^5=Boc$, and the carbon atom bearing $R^3$ has the (S) configuration)

TBTU (1.61 g, 5.00 mmol) was added to a solution of 4-(4-aminophenyl)-2-thiazolamine (956 mg, 5.00 mmol), (L)-Boc-phenylalanine (1.33 g, 5.00 mmol) and DIPEA (1.74 mL, 10.0 mmol) in DMF (50 mL) at room temperature. The reaction mixture was stirred at room temperature for 16 h. The mixture was diluted with EtOAc (250 mL). The resulting solution was washed with saturated aqueous $NaHCO_3$ (2×150 mL) and brine (100 mL), then dried ($MgSO_4$) and concentrated under reduced pressure. The residue was purified by flash chromatography ($SiO_2$, EtOAc:Hex, 1:1) to give the title compound (1.11 g, 51% yield) as a pale brown solid. Colorless crystals can be obtained by recrystallisation from EtOAc: M.p. 183–5°; $[\alpha]_D^{25}$+52.60 (c 0.53 NeOH); $^1$H NMR (400 MHz, DMSO-$d_6$) δ10.04 (s, 1H), 7.73 (d, J=8.7 Hz, 2H), 7.57 (d, J=8.7 Hz, 2H), 7.26–7.33 (m, 4H), 7.19 (t, J=7.1 Hz, 1H), 7.08 (d, J=8.4 Hz, 1H), 7.00 (s, 2H), 6.88 (s, 1H), 4.33 (m, 1H), 3.00 (dd, J=4.5, 13.4 Hz, 1H), 2.84 (dd, J=10.0, 13.4 Hz, 1H), 1.32 (s, 9H); MS (FAB) m/z 439 (MH)+; Anal. Calcd for $C_{23}H_{26}N_4SO_3$: C, 62.99; H, 5.98; N, 12.78. Found: C, 62.69; H, 5.99; N, 12.65.

Example 12

N-{4-(2-Amino-4-thiazolyl)phenyl}-5-oxo-1-(phenylmethyl)-2(R)-pyrrolidinecarboxamide (1: $R^1=NH_2$, $R^2=H$, $R^3$ and $R^4$ together form a $CH_2CH_2C(O)$ group and $R^5=PhCH_2$, and the carbon atom bearing $R^3$ has the (R)configuration)

a) N-(Phenylmethyl)glutamic acids {(R) and (S)}: N-(Phenylmethyl)glutamic acids were prepared using known procedures (P. Quitt, J. Hellerbach, K. Vogler, *Helv. Chim. Acta*, 1963, 46, 327 and J. S. Petersen, G. Fels, H. Rapoport, *J. Am. Chem. Soc.*, 1984, 106, 4539) with a minor modification. The solid obtained by precipitation of N-(phenylmethyl)glutamic acid from the aqueous reaction mixture at the isoelectric point (pH 3–4) was not dried as described but used as such in the next step.

b) 5-Oxo-1-(phenylmethyl)-2-pyrrolidinecarboxylic acids {2(R) and 2(S)}: 5-Oxo-1-(phenylmethyl)-2-pyrrolidinecarboxylic acids (2(R) and 2(S)) were prepared according to a known procedure (J. S. Petersen, G. Fels, H. Rapoport, *J. Am. Chem. Soc.*, 1984, 106, 4539) and gave colorless oils which crystallized on standing and were sufficiently pure to be used in the next step. For example, (D)-glutamic acid (50 g, 340 mmol) produced the title compound (2 (R); 27.66 g, 37% yield): $[\alpha]_D^{25}$ −47.4° (c 1.29 MeOH); $^1$H NMR (400 MHz, CDCl$_3$) δ8.2 (broad s, 1H), 7.19–7.38 (m, 5H), 5.16 (d, J=15.2 Hz, 1H), 4.02 (dd, J=9.5, 2.9 Hz, 1H), 3.98 (d, J=15.2 Hz, 1H), 2.55–2.69 (m, 1H), 2.43–2.54 (m, 1H), 2.24–2.36 (m, 1H), 2.11–2.22 (m,1H).

c) The title compound: To an ice-cold solution of 5-oxo-1-(phenylmethyl)-2(R)-pyrrolidinecarboxylic acid (13.81 g, 62.99 mmol) in dry THF (126 mL) under nitrogen were added N-methylmorpholine (8.3 mL, 75.58 mmol) and isobutyl chloroformate (9.0 mL, 69.29 mmol). The mixture was stirred at 0° for 30 min. 4-(4-Aminophenyl)-2-thiazolamine (12.05 g, 62.99 mmol) was added to the mixture. The reaction mixture was allowed to warm to room temperature and was stirred for an additional 19 h. The mixture was diluted with EtOAc (500 mL) and the resulting solution was extracted with 10% aqueous HCl (2×250 mL). The aqueous phase was rendered basic (pH=12) with 10N aqueous NaOH and extracted with EtOAc. This organic phase was washed with brine, dried (MgSO$_4$) and concentrated under reduced pressure to afford an orange solid (21.72 g). Purification by flash chromatography (SiO$_2$, EtOAc:MeOH, 1:0 to 10:1) followed by recrystallisation from ethanol yielded the title compound as a pale yellow solid (5.66 g, 23% yield): M.p. 245–6°; $[\alpha]_D^{25}$ +123.6 (c 1.006 MeOH); $^1$H NMR (400 MHz, DMSO-$d_6$) δ10.14 (s, 1H), 7.73 (d, J=8.5 Hz, 2H), 7.56 (d, J=8.5 Hz, 2H), 7.21–7.35 (m, 5H), 7.01 (s, 2H), 6.90 (s, 1H), 4.90 (d, J=15.3 Hz, 1H), 4.11 (dd, J=8.7, 3.3 Hz, 1H), 3.79 (d, J=15.2 Hz, 1H), 2.25–2.47 (m, 3H), 1.93–1.99 (m, 1H); MS (FAB) m/z 393 (MH)+; Anal. Calcd for $C_{21}H_{20}N_4OS_2$: C, 64.27; H, 5.14;, N, 14.27. Found: C, 63.45; H, 5.16; N 14.17.

Example 13 tert-Butyl 2(S)-{{(4-(2-Amino-4-thiazolyl)phenyl}-amino}carbonyl}-1-pyrrolidinecarboxylate (1: $R^1$-$NH_2$, $R^2=H$, $R^3$ and $R^4$ together form a $CH_2CH_2CH_2$ group and $R^5=Boc$, and the carbon atom bearing $R^3$ has the (S)configuration)

To (L)-Boc-proline (935 mg, 4.35 mmol) in dry THF (9 mL) were added successively 4-(4-aminophenyl)-2-thiazolamine (831 mg, 4.35 mmol), DIPEA (2.3 mL, 13.04 mmol) and TBTU (1.535 g, 4.79 mmol). The mixture was stirred at room temperature for 18 h. The reaction mixture was concentrated under reduced pressure. The residue thus obtained was diluted with EtOAc and extracted with 10% aqueous HCl. The resulting aqueous phase was rendered basic (pH =12) with 10N aqueous NaOH and extracted with EtOAc. The organic extract was dried (MgSO$_4$) and concentrated under reduced pressure. Purification by flash chromatography (SiO$_2$, EtOAc) afforded the desired product (1.04 g, 62% yield) as an off-white solid which could be used as such in the next transformation or further purified by recrystallisation from EtOAc-MeOH to give a white solid: M.p. 238–239°; $[\alpha]_D^{25}$ −33.6 (c 1.03 DMSO); $^1$H NMR (400 MHz, DMSO-$d_6$) δ (2:1 mixture of rotamers) 9.98 (s, 1H), 7.72 (d, J=8.4 Hz, 2H), 7.59 (d, J=8.4 Hz, 2H), 7.00 (s, 2H), 6.88 (s, 1H), 4.19 (maj.) and 4.26 (dd, J=8.1, 4.5 Hz and d, J=6.6 Hz, 1H), 3.30–3.45 (m, 2H), 2.15–2.25 (m, 1H), 1.75–1.95 (m, 3H), 1.27 (maj.) and 1.40 (2s, 9H); MS (FAB) m/z 389 (MH)+; Anal. Calcd for $C_{19}H_{24}N_4O_3S$: C, 58.74; H, 6.23; N, 14.42. Found: C, 58.35; H, 6.26; N, 14.35.

Example 14

N-{4-(2-Amino-4-thiazolyl)phenyl}-1-benzoyl-2(S)-pyrrolidinecarboxamide: (1: $R^1=NH_2$, $R^2=H$, $R^3$ and $R^4$ together form a $CH_2CH_2CH_2$ group and $R^5$=H, and the carbon atom bearing $R^3$ has the (S) configuration)

a) N-{4-(2-Amino-4-thiazolyl)phenyl}-2(S)-pyrrolidinecarboxamide: Trifluoroacetic acid (5 mL) was added to a solution of the title compound of example 13 (610 mg, 1.57 mmol) in $CH_2Cl_2$ (20 mL). The mixture was stirred at room temperature for 1.5 h. The mixture was then diluted with EtOAc and the resulting solution was washed with 2N aqueous NaOH and brine, then was dried ($MgSO_4$) and concentrated under reduced pressure to afford the desired product (400 mg, 88% yield) as a beige foam: $^1$H NMR (400 MHz, DMSO-$d_6$) δ9.96 (s, 1H), 7.72 (d, J=8.7 Hz, 2H), 7.64 (d, J=8.7 Hz, 2H), 6.99 (s, 2H), 6.89 (s, 1H), 3.69 (dd, J=8.8, 5.6 Hz, 1H), 2.90 (t, 2H, J=6.6 Hz), 2.69 (s, 1H), 2.00–2.10 (m, 1H), 1.74–1.83 (m, 1H), 1.65 (quint., 2H, J=6.9 Hz).

b) The title compound: The product of preceding section a) (200 mg, 0.694 mmol) was dissolved in dry THF (3.5 mL). Benzoic acid (85 mg, 0.694 mmol), N-methylmorpholine (153 μL, 1.39 mmol) and TBTU (245 mg, 0.763 mmol) were added to the solution. The mixture was stirred at room temperature for 1.5 h, and then concentrated under reduced pressure. The residue was dissolved in EtOAc. The solution was extracted with 10% aqueous HCl. The aqueous phase was rendered basic (pH 12) with 10% aqueous NaOH and then extracted with EtOAc. The extract was dried ($Na_2SO_4$) and concentrated under reduced pressure to afford a yellow oil. The oil was purified by flash chromatography ($SiO_2$, EtOAc) and then lyophilized from acetonitrile-$H_2O$ to afford the title compound (141 mg, 52% yield) as an off-white solid of >96.5% purity (containing acetonitrile): Mp 132–133°; $[\alpha]_D^{25}$ –122.3 (c 1.00, MeOH); $^1$H NMR (400 MHz, DMSO-$d_6$), (4:1 mixture of rotamers), δ10.10 (major) and 9.74 (s, 1H), 7.74 (d, J=8.7 Hz, 2H), 7.62 (d, J=8.7 Hz, 2H), 7.65–7.70, 7.55–7.57 and 7.33–7.37 (m, 5H), 6.99 (s, 2H), 6.89 (major) and 6.87 (s, 1H), 4.60 (major) and 4.38 [(dd, J=7.9, 5.2 Hz) and (d, J=7.1 Hz), 1H], 3.49–3.69 (m, 2H), 2.20–2.35 (m, 1H), 1.80–2.00 (m, 3H); MS (FAB) m/z 393 (MH)$^+$;Anal. Calcd for $C_{21}H_{20}N_4O_2S$: C, 64.27; H, 5.14; N, 14.27. Found: C, 61.64; H, 5.34; N, 14.50.

Example 15

N-{4-(2-Amino-4-thiazolyl)phenyl}-1-(phenylmethyl)-2 (S)-pyrrolidinecarboxamide (1: $R^1$=NH2, $R^2$=$CH_3$, $R^3$ and $R^4$ together form a $CH_2CH_2CH_2$ group and $R^5$=$PhCH_2$, and the carbon atom bearing $R^3$ has the (S) configuration)

The title compound (573 mg, 31% yield) was prepared from (L)-N-(phenylmethyl)proline (1.00 g, S. W. Goldstein, L. E. Overman, M. H. Rabinowitz, J. Org. Chem. 1992, 57, 1179) and 4-(4-aminophenyl)-2-thiazolamine using the procedure described for the tert-butyl carboxylate derivative in example 13. The title compound had m.p. 207–9°; $[\alpha]_D^{25}$ –88.7 (c 1.00 $CHCl_3$); $^1$H NMR (400 Mz, DMSO-$d_6$) δ9.69 (s, 1H), 7.72 (d, J=8.7 Hz, 2H), 7.59 (d, J=8.7 Hz, 2H), 7.39 (d, J=6.9 Hz, 2H), 7.31 (t, J=7.2 Hz, 2H), 7.22 (t, J=7.2 Hz, 1H), 6.99 (s, 2H), 6.89 (s, 1H), 3.84 (d, J=12.9 Hz, 1H), 3.60 (d, J=12.9 Hz, 1H), 3.24 (dd, J=9.3, 4.8 Hz, 1H), 3.01–3.06 (m, 1H), 2.40 (q, J=8.4 Hz, 1H), 2.11–2.21 (m, 1H), 1.72–1.89 (m, 3H); MS (FAB) m/z 379 (MH)$^+$; Anal. Calcd for $C_{21}H_{22}N_4OS$: C, 66.64; H, 5.86; N, 14.80. Found: C, 66.24; H, 5.77; N, 14.48.

Example 16

The following four assays (A, B and Ci and Cii) were used to evaluate antiherpes activity, and a fifth assay (D) was used to measure the stabilization of the DNA-herpes helicase-primase interaction.

A) HSV-1 DNA-Dependent ATP Assay (an in vitro assay based on the inhibition of HSV-1 helicase-primase).

a) Preparation of enzyme: HSV-1 helicase-primase holoenzyme was produced in triply infected Sf21 cells using recombinant baculoviruses expressing the UL5, UL8 and UL52 helicase-primase subunits, as described by S. Dracheva et al., J. Biol. Chem. 1995, 270, 14148. The crude enzyme was purified by ammonium sulfate precipitation, Source 15Q® chromatography and Sephacryl® S-300 HR gel filtration (both purification systems can be obtained from Pharmacia Biotech Inc., Montreal, Quebec, Canada), see S. Dracheva et al., supra.

b) Assay: The DNA-dependent ATPase assay, described by J. J. Crute et al., Nucleic Acids Res. 1988, 16, 6585, was modified and used to evaluate the capability of the compounds of Group 1-formula 1 to inhibit HSV-1 helicase-primase activity. The reaction mixtures (80 μL each) contained 40 mM 4-(2-hydroxyethyl)-1-piperazineethanesulfonic acid (HEPES, pH 7.5), 10% (v/v) glycerol, 5.5 MM $MgCl_2$, 1 mM DL-dithiothreitol (DTT), 50 μg/mL acetylated bovine serum albumin, 3.3% (v/v) DMSO, 4 mM ATP, 25 μM single-stranded M13 DNA hybridized to double-tailed 68-mer oligonucleotide and 3 μg/mL HSV-1 helicase-primase. After incubation for 20 min at 34°, formation of inorganic phosphate from hydrolysis of ATP was monitored spectrophotometrically at 650 nm using acidic ammonium molybdate/malachite green reagent, P.A. Lanzetta et al., Anal. Biochem. 1979, 100, 95. DNA-dependent ATPase activity was calculated from the net absorbance change in the presence and absence of inhibition.

B) Inhibition of Herpes Simplex Virus (HSV-1) Replication in Cell Culture

Assay: BHK-21 cells clone 13 (ATCC CCL10) were incubated for two days in 850 cm$^2$ roller bottles (2×10$^7$ cells/bottle) with α-MEM medium (Gibco Canada Inc., Burlington, Ontario, Canada) supplemented with 8% (v/v) fetal bovine serum (FBS, Gibco Canada, Inc.). The cells were trypsinized and then 3,000 cells in 100 μL of fresh medium were transferred into each well of a 96-well microtiter plate. The cells were incubated at 37° for a period of 3 days to reach a density of 50,000 cells per well. The cells were washed twice with 100 μL of α-MEM supplemented with 2% heat inactivated FBS and incubated for 1–2 hours in 100 μL of the same medium.

Thereafter, the cells were infected with HSV-1 strain F or KOS (multiplicity of infection =0.05 PFU/cell) in 50 μL of α-MEM supplemented with 2% heat inactivated FBS. Following one hour of virus absorption at 37°, the medium was removed and the cells were washed with α-MEM supplemented with 2% heat inactivated FBS (2×100 μL). The cells were incubated with or without 100 μL of the appropriate concentration of test reagent in α-MEM medium supplemented with 2% heat inactivated FBS. After 24 hours of incubation at 37°, the extent of viral replication was determined by an ELISA assay; for instance, the following assay that detects the late glycoprotein C of HSV-1.

Cells were fixed in the microtiter plate with 100 μL of 0.063% glutaraldehyde in phosphate buffered saline for 30 min at room temperature. The microtiter plate was then washed once with casein blocking solution and blocked with 200 μL of the same solution for one hour at room temperature. Thereafter, 100 μL of mAb C11 recognizing the glycoprotein C of HSV-1 (see E. Trybala et al., Journal of General Virology, 1994, 75, 743) was added to each well for two hours at room temperature. The plate was washed three times with phosphate buffered saline containing 0.05% polyoxyethylene (20) sorbitan monooleate. The cells were incubated with 100 μL of sheep anti-mouse IgG horseradish peroxidase for one hour at room temperature in the dark.

The plate was washed three times with 200 μL of the above-noted phosphate buffer saline preparation, and then once with 0.1M sodium citrate (pH 4.5). Thereafter, 100 μL of orthophenylenediamine dihydrochloride (OPD, Gibco, Canada Inc.) was added to each well. The plate was agitated on a microplate shaker for 30 min in the dark. Color development was monitored at 450 nm using a microplate spectrophotometer.

SAS was used to calculate % inhibition of viral replication and to generate $EC_{50}$ values.

C) Inhibition of Human Cytomegalovirus (HCMV) replication

The effect of compounds on the replication of HCMV has been measured by using an ELISA-based assay (ELISA) and a plaque reduction assay (PRA).

Ci) ELISA ASSAY

Hs-68 cells (ATCC # CRL 1635) were seeded in 96 well microtiter plates at 10,000 cells/well in 100 μL of DMEM medium (Gibco Canada Inc.) supplemented with 10% fetal bovine serum (FBS, Gibco Canada Inc.). The plates were incubated for 3 days at 37° to allow the cells to reach 80–90% confluency prior to the assay.

The medium was removed from wells by aspiration. The cells then were infected at a multiplicity of infection (MOI) of 0.01 PFU/cell with 50 μL of HCMV (strain AD169, ATCC VR-538) in DMEM medium supplemented with 5% heat inactivated FBS (assay medium). The virus was allowed to adsorb to cells for 2 h at 37°. Following viral adsorption, the medium was removed from the wells by aspiration. The cells were washed twice with 200 μL of assay medium to remove unabsorbed virus. The cells were then incubated with or without 100 μL of appropriate concentrations of test reagent in assay medium. After 8 days of incubation at 37°, the extent of viral replication was determined by an ELISA assay which detects the late structural protein p28 of HCMV.

Eight days after infection, the medium was aspirated from the wells. Non-specific binding sites were blocked by adding 200 μL of phosphate buffered saline containing 1% (w/v) bovine serum albumin (blocking buffer) to each well and incubating the plates for 30 min at room temperature. After removal of the blocking buffer by aspiration, the cells were fixed with 100 μL of cold ethanol-acetone solution (95:5) per well. The plates were placed at −20° for 30 min. The plates were washed 4 times with phosphate buffered saline containing 0.05% (v/v) polyoxyethylene sorbitan monolaurate (Tween 20 ®). Thereafter, 100 μL of mAb UL99 (Advanced Biotechnologies Inc., # 13-130-100) recognizing HCMV protein p28 was added to each wells and plates were incubated for 2 h at room temperature. The plates were washed four times with 200 μL of the above-noted phosphate buffered saline/Tween-20® solution. The cells were then incubated with 100 μL of sheep anti-mouse IgGγ horseradish peroxidase conjugated for 2 h at room temperature. The plates were then washed four times with 200 μL of above-noted phosphate buffered saline/Tween-20® solution. Thereafter, 100 μL of ortho phenylenediamine dihydrochloride (OPD, Gibco Canada Inc.) solution was added to each well and the plates were agitated on a microplate shaker for 30 min in the dark.

Color development was monitored at 450 nm using a microplate spectrophotometer.

The SAS program was used to calculate the % inhibition of viral replication and to generate $EC_{50}$ values.

The $EC_{50}$ values obtained according to this assay method for certain thiazolylphenyl derivatives of this invention are listed in the following tables under the heading ELISA CMV.

Cii) PRA ASSAY

Hs-68 cells (ATCC # CRL 1635) were seeded in 12-well plates at 83,000 cells/well in 1 mL of DMEM medium (Gibco Canada Inc.) supplemented with 10% fetal bovine serum (FBS, Gibco Canada Inc.). The plates were incubated for 3 days at 37° to allow the cells to reach 80–90% confluency prior to the assay.

The medium was removed from the cells by aspiration. The cells were then infected with approximately 50 PFU of HCMV (strain AD169, ATCC VR-538) in DMEM medium supplemented with 5% inactivated FBS (assay medium). The virus was allowed to adsorb to cells for 2 h at 37°. Following viral adsorption, the medium was removed from the wells by aspiration. The cells were then incubated with or without 1 mL of appropriate concentrations of test reagent in assay medium. After 4 days of incubation at 37°, the medium was exchanged with fresh medium containing test compound and 4 days later the cells were fixed with 1% aqueous formaldehyde and stained with a 2% crystal violet solution in 20% ethanol in water. Microscopic plaques were counted using a stereomicroscope. Drug effects were calculated as a percent reduction in the number of plaques in the presence of each drug concentration compared to the number observed in the absence of drug. Ganciclovir was used as a positive control in all experiments.

The $EC_{50}$ values obtained according to this assay for certain thiazolyl derivatives of this invention are listed in the following tables under the heading PRA CMV.

D) HSV-1 Helicase-primase-DNA stabilization assay

The following represents a preferred protocol which was used for designing single-stranded fluorescently labeled DNA substrate to measure the stabilization of the DNA-herpes helicase-primase interaction (Tenney, D. J., Scheaffer, A. K., Hurlburt, W. W., Bifano, M., and Hamatake, R. K. (1995) *J. Biol. Chem.*, 270, 9129–9136):

A foldback 86-mer oligonucleotide designed to mimic a replication fork-like structure was prepared, where one nucleic acid base was replaced with fluorescein using phosphoramidite chemistry. An example of such a substrate is 5'-CCAACGTCCFGTATAATGAGGTACCCGGGGATCC-TCTAGGATATATCCTAGAGGATCCCCGGGTACGGTA-TAATGAGCCAGTTCTT-3', where F=fluorescein. Other oligonucleotide sequences may be used as long as the secondary structure (replication fork) is maintained. The fluorescent probe may be located anywhere within the sequence, except at either the 5' or 3' ends. Single stranded oligonucleotides containing the primase consensus binding site may also be used. An example of such a substrate is 5'-CCAACGTCCCTACCCTCCCGAFTATAATGAG-3', where F=fluorescein. Other sequences containing the primase consensus binding site (CCCTCCCGA) may be used. The fluorescent probe may be located anywhere within the sequence, except at either the 5' or 3' ends or within the primase binding site.

Solutions for fluorescence anisotropy analysis (2 mL total) contained 40 mM 4-(2-hydroxyethyl)-1-piperazineethanesulfonic acid (HEPES, pH 7.5), 10% (v/v) glycerol, 5.5 mM $MgCl_2$, 1 mM DL dithiothreitol (DTT), 0.1%–3.0% (v/v) DMSO, 100 μM ATPγS, 150 mM NaCl, 25 nM fluorescein-labeled oligonucleotide, 250 nM helicase-primase (UL5/UL52 subassembly). Fluorescence anisotropy was measured through a LG-530 filter (Corion) using an excitation wavelength of 490 nm. Anisotropy values were converted to fraction oligonucleotide bound to enzyme in the presence and absence of inhibitor. Stabilization of enzyme-DNA complex by an inhibitor was demonstrated by an increase in fraction oligonucleotide bound.

The effect was further characterized by measuring the binding affinities of oligonucleotide for enzyme in the presence and absence of inhibitor. The solutions (2 mL total) contained 40 mM HEPES, pH 7.5, 10% (v/v) glycerol, 5.5 mM $MgCl_2$, 1 mM DL dithiothreitol (DTT), 0.1%–3.0% (v/v) DMSO, 100 µM ATPγS, 150 mM NaCl, 25 nM fluorescein labeled oligonucleotide. Aliquots of helicase-primase (UL5/UL52 subassembly) were added and fluorescence anisotropy was measured after each addition until no further anisotropy change was observed. Nonlinear regression analysis was used to calculate dissociation constants from the anisotropy values for enzyme binding to oligonucleotide in the presence and absence of inhibitor.

Figure 5:
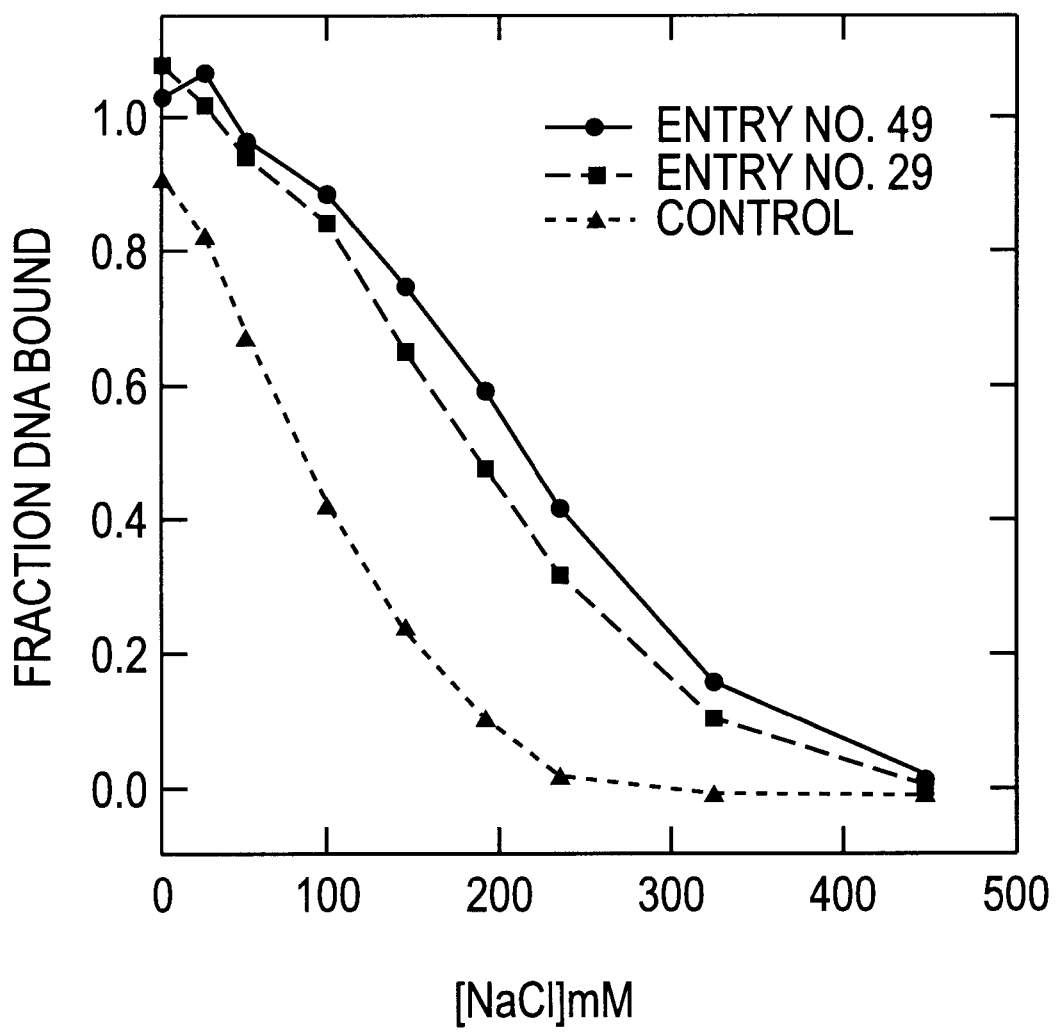
FIG. 5 graphically illustrates the ability of two thiazolylphenyl derivatives of Group 1 to stabilize the interaction between the herpes HSV-1 helicase-primase and a DNA substrate.

Examples of results obtained in accordance with this assay for two thiazolyphenyl derivatives are illustrated in FIG. 5. The two derivatives are N-{2-{{4-(2-amino-4-thiazolyl)phenyl}amino}-2-oxoethyl}-N-(4-pyridinylmethyl)cyclohexane-carboxamide(Entry No. 49 of Table 1 of Group 1) and N-{2-{(4-(2-amino-4-thiazolyl)phenyl)amino}-2-oxoethyl)-N-(phenylmethyl)-4-pyridinecarboxamide (Entry No 29 of Table 1 of Group 1).

Example 17

In conjunction with the appropriate starting materials and intermediates, the procedures of Group 1-examples 1 to 15 can be used to prepare other compounds of Group 1-formula 1. Examples of compounds thus prepared are listed in Tables 1 to 6 of Group 1-example 17, together with mass spectrum data for the individual compounds and the results obtained from three assays demonstrating antiheroes activity.

(Symbols used in the following Group 1 tables, and in subsequent tables, include 4-ClPh: 4-chlorophenyl; 4-Cl-3-IPh: 4-chloro-3-iodophenyl; 2-FPh: 2-fluorophenyl; 3-FPh: 3-fluorophenyl; 4-FPh: 4-fluorophenyl;(4-$Me_2$NPh)$CH_2$: (4-(dimethylamino)-phenyl}methyl; 2-MePh: 2-methylphenyl; 4-MePh: 4-methylphenyl; 2,6-$Me_2$Ph: 2,6-dimethylphenyl; 4-MeOPh: 4-methoxyphenyl; 5-Cl-2-MeOPh: 5-chloro-2-methoxyphenyl.)

TABLE 1

Compound of formula 1 having the structure

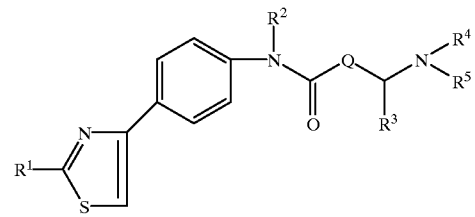

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) (MH)$^+$ | HSV-1 $IC_{50}$ (µM) | HSV-1 $EC_{50}$ (µM) | ELISA CMV $EC_{50}$ (µM) | PRA CMV $EC_{50}$ (µM) |
|---|---|---|---|---|---|---|---|
| 1 | H | $PhCH_2$ | 339 | 6.4 | 2.7 | 25 | >60 |
| 2 | H | $PhCH_2CH_2$ | 353 | 4.7 | 6 | 3.1 | |
| 3 | H | $PhCH_2CH_2CH_2$ | 367 | 7.6 | 18 | 1.8 | >14* |
| 4 | H | (4-FPh)$CH_2$ | 357 | 3.5 | 1.8 | | 16 |
| 5 | H | (4-ClPh)$CH_2$ | 373/375** | 5.4 | 42 | | |
| 6 | H | (4-MePh)$CH_2$ | 353 | 19 | 18 | | |
| 7 | H | (4-MeOPh)$CH_2$ | 369 | 48 | 7 | | |
| 8 | H | cyclohexyl-$CH_2$ | 345 | 2.9 | 8 | 3.6 | |
| 9 | H | (3-FPh)$CH_2$ | | ca.5 | | | |
| 10 | H | Ph-(S)—CHMe | 353 | 6.9 | 2.2 | 2.2 | >30* |
| 11 | H | Ph-(R)—CHMe | 353 | 3.7 | 1.3 | 19 | 19 |
| 12 | H | 2-pyridyl-$CH_2$ | 340 | 8 | 1.5 | | 84* |
| 13 | H | 2-thienyl-$CH_2$ | 345 | 3.8 | 3.7 | 8.3 | |

TABLE 1-continued

Compound of formula 1 having the structure

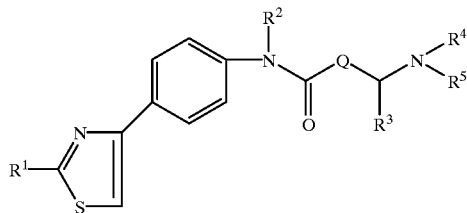

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 14 | H | morpholine-$NCH_2CH_2$ | 362 | 7.7 | 3.2 | 67 | |
| 15 | $PhCH_2$ | Me | 353 | 3.3 | 0.95 | 6.2 | 6.5 |
| 16 | $PhCH_2$ | $PhCH_2$ | 429 | 0.55 | 0.45 | 3.8 | 13 |
| 17 | (2-FPh)$CH_2$ | (2-FPh)$CH_2$ | | 1.8 | 4.0 | | |
| 18 | (3-FPh)$CH_2$ | (3-FPh)$CH_2$ | | 0.4 | 0.1 | | |
| 19 | H | 2-pyridyl-C(O) | 354 | 13 | 4.5 | | 20 |
| 20 | H | 3-pyridyl-C(O) | | 23 | | | 60 |
| 21 | H | 4-pyridyl-C(O) | | 4.2 | 1.3 | | >71 |
| 22 | Me | 4-pyridyl-C(O) | 368 | 5.9 | 1.8 | 110 | 110* |
| 23 | $PhCH_2$ | PhC(O) | 443 | 0.072 | 0.007 | 12 | 36 |
| 24 | $PhCH_2$ | (4-FPh)C(O) | 461 | 0.048 | 0.002 | 14 | 15 |
| 25 | $PhCH_2$ | (2,6-$Me_2$Ph)C(O) | 471 | 0.047 | 0.011 | 4.4 | |
| 26 | $PhCH_2$ | $PhCH_2$C(O) | 455 | 0.5 | 0.05 | 1.8 | 15 |
| 27 | $PhCH_2$ | 2-pyridyl-C(O) | 444 | 1.0 | 0.28 | 7 | >36* |
| 28 | $PhCH_2$ | 3-pyridyl-C(O) | 444 | 0.43 | 0.13 | 4.6 | 35 |
| 29 | $PhCH_2$ | 4-pyridyl-C(O) | 444 | 0.24 | 0.035 | 12 | 27 |

TABLE 1-continued

Compound of formula 1 having the structure

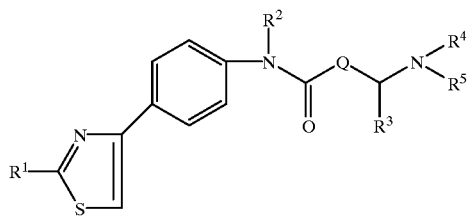

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) (MH)+ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|
| 30 | PhCH$_2$ | 4-pyridyl N-oxide-C(O)- | 460 | 0.44 | 0.43 | 77 | >88 |
| 31 | PhCH$_2$ | 2-pyridyl-CH$_2$C(O)- | 458 | 1.6 | 0.4 | 1.3 | 8.1 |
| 32 | PhCH$_2$ | 2-thienyl-C(O)- | 449 | 0.42 | 0.04 | 5.4 | 8.5 |
| 33 | PhCH$_2$ | pyrazinyl-C(O)- | 445 | 1.1 | 0.17 | 28.2 | 20 |
| 34 | PhCH$_2$ | cyclohexyl-C(O)- | 449 | 0.026 | 0.004 | 1 | 15 |
| 35 | PhCH$_2$ | 1-methylcyclohexyl-C(O)- | 463 | 0.035 | 0.006 | 8.1 | |
| 36 | PhCH$_2$ | cyclopentyl-C(O)- | 435 | 0.041 | 0.005 | 2.8 | 16 |
| 37 | PhCH$_2$ | cycloheptyl-C(O)- | 463 | 0.029 | 0.002 | | >74 |
| 38 | PhCH$_2$ | cyclohexyl-CH$_2$C(O)- | 463 | 0.088 | 0.016 | 4 | 4.6 |

TABLE 1-continued

Compound of formula 1 having the structure

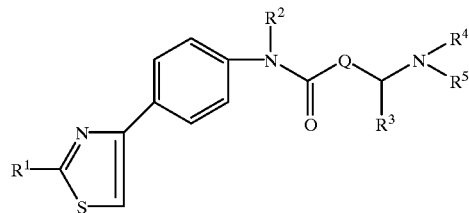

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 39 | PhCH$_2$ | cyclopentyl-CH$_2$C(O) | 449 | 0.059 | 0.009 | 6.1 | 8.5 |
| 40 | PhCH$_2$ | Boc-N-piperidinyl-C(O) | 550 | 1.7 | 0.7 | 25 | |
| 41 | PhCH$_2$ | Me$_3$CC(O) | 423 | 0.80 | 0.036 | 14 | 34 |
| 42 | PhCH$_2$ | Me$_3$CCH$_2$C(O) | 437 | 0.026 | 0.002 | 6 | 20 |
| 43 | PhCH$_2$ | Me$_2$CHC(O) | 409 | 1.6 | 0.13 | 25 | 13 |
| 44 | PhCH$_2$ | MeC(O) | 381 | 3.3 | 0.75 | 16 | 37 |
| 45 | (4-ClPh)CH$_2$ | cyclohexyl-C(O) | 483/485** | 0.050 | 0.001 | | 5.5 |
| 46 | (4-MeOPh)CH$_2$ | cyclohexyl-C(O) | 479 | 0.075 | 0.094 | 8 | |
| 47 | 2-pyridyl-CH$_2$ | cyclohexyl-C(O) | 450 | 0.072 | 0.013 | 19 | >103 |
| 48 | 3-pyridyl-CH$_2$ | cyclohexyl-C(O) | 450 | 0.14 | 0.04 | 5 | 49 |
| 49 | 4-pyridyl-CH$_2$ | cyclohexyl-C(O) | 450 | 0.037 | 0.012 | 25 | 23 |
| 50 | 2-pyridyl-CH$_2$CH$_2$ | cyclohexyl-C(O) | 464 | 0.6 | 0.068 | 1.6 | 13 |
| 51 | 2-thienyl-CH$_2$ | cyclohexyl-C(O) | 455 | 0.063 | 0.002 | 6 | 11 |

TABLE 1-continued

Compound of formula 1 having the structure

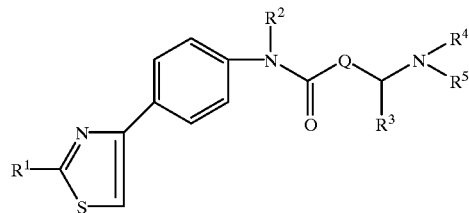

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 52 | Ph-(R)—CHMe | cyclohexyl-C(O) | 463 | 0.087 | 0.013 | 1.3 | 6 |
| 53 | Ph-(S)—CHMe | cyclohexyl-C(O) | 463 | 0.038 | 0.003 | 3.2 | 12 |
| 54 | morpholino-NCH$_2$CH$_2$ | cyclohexyl-C(O) | 466 | 16 | 3.5 | 31 | 63 |
| 55 | (4-ClPh)CH$_2$ | 4-pyridyl-C(O) | 478/480** | 0.57 | 0.095 | 11.9 | |
| 56 | 2-pyridyl-CH$_2$ | 4-pyridyl-C(O) | 445 | 1.2 | 0.55 | 38 | |
| 57 | cyclohexyl-CH$_2$ | 4-pyridyl-C(O) | 450 | 3.9 | 0.95 | 2.6 | 15.8 |
| 58 | Ph-(S)—CHMe | 4-pyridyl-C(O) | 458 | 0.19 | 0.04 | 5.2 | 30 |
| 59 | (4-FPh)CH$_2$ | PhC(O) | 461 | 0.30 | 0.015 | | |
| 60 | cyclohexyl-CH$_2$ | PhC(O) | 449 | 1.5 | 0.54 | 3 | 15 |
| 61 | cyclohexyl-CH$_2$ | Boc-N-piperidinyl-C(O) | 556 | 4.4 | 1.6 | | |
| 62 | cyclohexyl-CH$_2$ | HN-piperidinyl-C(O) | 456 | 29% inhibition at 50 $\mu M$ | 5.5 | 2.2 | 38 |

TABLE 1-continued

Compound of formula 1 having the structure

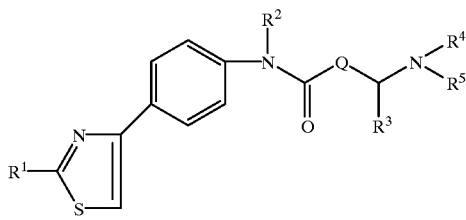

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 63 | cyclohexyl-CH$_2$ | cyclopentyl-C(O) | 441 | 0.78 | 0.25 | 2.2 | >21* |
| 64 | cyclohexyl-CH$_2$ | 3-pyridyl-C(O) | 450 | 2.5 | 1.7 | 0.75 | 20 |
| 65 | (4-ClPh)CH$_2$ | 4-N$_3$-Ph-C(O) | 519 | 0.84 | | | |
| 66 | PhCH$_2$CH$_2$ | cyclopentyl-C(O) | 449 | 0.40 | 0.090 | 0.35 | >10 |
| 67 | PhCH$_2$CH$_2$ | 3-pyridyl-C(O) | 458 | 0.35 | 0.21 | 2.1 | 93 |
| 68 | PhCH$_2$CH$_2$ | cyclohexyl-C(O) | 463 | 0.18 | 0.05 | >5 | |
| 69 | (4-ClPh)CH$_2$ | cyclohexyl-CH$_2$C(O) | 497 | 0.43 | 0.18 | | 8 |
| 70 | (4-Cl-3-IPh)CH$_2$ | 4-pyridyl-C(O) | 478/480** (M-I) | 0.57 | 0.16 | | |
| 71 | PhCH$_2$ | NH$_2$CH$_2$C(O) | 396 | 30 | | | >32 |
| 72 | PhCH$_2$ | Me$_3$COC(O)—NHCH$_2$C(O) | 496 | 0.65 | 0.67 | 7.5 | 24 |
| 73 | 4-pyridyl-CH$_2$ | (4-FPh)C(O) | 462 | 0.088 | 0.017 | 12.6 | |

TABLE 1-continued

Compound of formula 1 having the structure

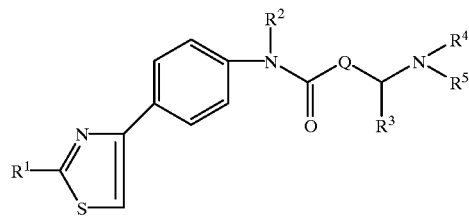

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 74 | PhCH$_2$ | N$_3$-Ph-C(O) | 484 | 0.28 | 0.12 | | |
| 75 | Cyclohexyl-CH$_2$ | Cyclopentyl-CH$_2$C(O) | 455 | 0.21 | 0.24 | 48 | |
| 76 | Cyclohexyl-CH$_2$ | Cyclohexyl-CH$_2$C(O) | 469 | 0.08 | 0.16 | 25 | |
| 77 | Cyclohexyl-CH$_2$ | PhCH$_2$C(O) | 464 | 0.37 | 0.19 | 6.1 | 7.5 |
| 78 | 4-Pyridyl-CH$_2$ | N$_3$-Ph-C(O) | 485 | 1 | 0.18 | | |
| 79 | 2-Pyridyl-CH$_2$CH$_2$ | Cyclopentyl-C(O) | 450 | 0.84 | 0.16 | 3.8 | 55 |
| 80 | Me$_3$CCH$_2$ | Cyclohexyl-C(O) | 429 | 0.96 | 0.31 | 9.5 | 9.5 |
| 81 | Me$_2$CHCH$_2$ | Cyclohexyl-C(O) | 415 | 0.48 | 0.18 | 14 | |
| 82 | Pr$_2$CH | Cyclohexyl-C(O) | 457 | 0.62 | 0.060 | 8.1 | 7* |
| 83 | (4-FPh)CH$_2$ | Cyclohexyl-C(O) | 467 | 0.042 | 0.006 | 8.1 | |

TABLE 1-continued

Compound of formula 1 having the structure

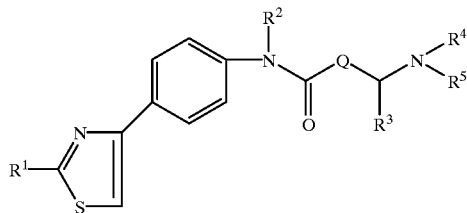

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu$M) | HSV-1 $EC_{50}$ ($\mu$M) | ELISA CMV $EC_{50}$ ($\mu$M) | PRA CMV $EC_{50}$ ($\mu$M) |
|---|---|---|---|---|---|---|---|
| 84 | (4-FPh)CH$_2$ | ![pyridine-4-C(O)] | 462 | 0.36 | 0.14 | 5.6 | 37 |
| 85 | PhCH$_2$ | Me$_3$COC(O) | 439 | 0.016 | 0.010 | 0.6 | 12 |
| 86 | PhCH$_2$ | Me$_2$CHCH$_2$OC(O) | 439 | 0.17 | 0.088 | 3.8 | 24 |
| 87 | PhCH$_2$ | MeOC(O) | 397 | 2.8 | 1.1 | 18 | |
| 88 | Ph-(R)—CHMe | Me$_3$COC(O) | 453 | 2.4 | 1.2 | >47 | |
| 89 | Ph-(S)—CHMe | Me$_3$COC(O) | 453 | 0.098 | 0.036 | 0.9 | 38 |
| 90 | pyridin-4-yl-CH$_2$ | Me$_3$COC(O) | 440 | 0.058 | 0.015 | 3.5 | 88 |
| 91 | (4-ClPh)CH$_2$ | Me$_3$COC(O) | 473/475** | 0.070 | 0.025 | 1.6 | |
| 92 | PhCH$_2$ | Me$_3$CNHC(O) | 438 | 0.076 | 0.034 | 0.9 | 65 |
| 93 | PhCH$_2$ | Me$_3$CNHC(S) | 454 | 0.16 | 0.12 | 0.25 | >24 |
| 94 | PhCH$_2$ | Me$_3$CN(Me)—C(O) | 452 | 0.026 | 0.065 | >8 | >24 |
| 95 | PhCH$_2$ | morpholine-NC(O) | 452 | 0.14 | 0.037 | 57 | 90 |
| 96 | PhCH$_2$ | morpholine-NS(O)$_2$ | 488 | 0.29 | 0.12 | 0.35 | 12 |
| 97 | PhCH$_2$ | PhS(O)$_2$ | 479 | 0.31 | 0.13 | >5 | 15 |
| 98 | PhCH$_2$ | 5-NMe$_2$-naphth-1-yl-S(O)$_2$ | 572 | 0.5 | 2.1 | >2 | |
| 99 | pyridin-4-yl-CH$_2$ | 5-NMe$_2$-naphth-1-yl-S(O)$_2$ | 573 | 1.6 | 0.67 | | |

TABLE 1-continued

Compound of formula 1 having the structure

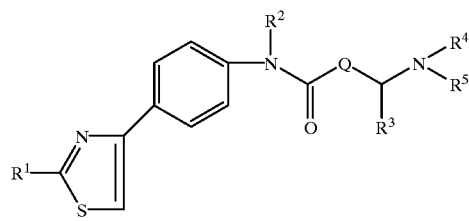

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu$M) | HSV-1 $EC_{50}$ ($\mu$M) | ELISA CMV $EC_{50}$ ($\mu$M) | PRA CMV $EC_{50}$ ($\mu$M) |
|---|---|---|---|---|---|---|---|
| 100 | cyclohexyl-CH$_2$ | Me$_3$COC(O) | 445 | 0.76 | 0.85 | 14 | |
| 101 | 2-pyridyl-CH$_2$CH$_2$ | Me$_3$COC(O) | 454 | 2.2 | 0.74 | 1.9 | |
| 102 | (2-MePh)CH$_2$ | 4-pyridyl-C(O) | 458 | 0.19 | 0.011 | 11 | 18 |
| 103 | cyclohexyl-CH$_2$CH$_2$ | cyclohexyl-C(O) | 469 | 0.15 | 0.24 | >41 | |
| 104 | PhCH$_2$ | Et$_2$CHC(O) | 437 | 0.078 | 0.016 | 1.9 | >18* |
| 105 | Ph-(S)—CHMe | Me$_3$CNHC(O) | 452 | 0.7 | 0.29 | 11 | |
| 106 | PhCH$_2$ | Me$_2$NS(O)$_2$ | 446 | 1.0 | 0.16 | >6 | |
| 107 | cyclohexyl-CH$_2$ | morpholino-N—S(O)$_2$ | 494 | 2.6 | 0.83 | 1.1 | 12* |
| 108 | cyclohexyl-(S)—CHMe | Me$_3$COC(O) | 459 | 0.46 | 0.39 | 6.8 | |
| 109 | PhCH$_2$ | PhCH$_2$OC(O) | 473 | 0.31 | 0.2 | >20 | |
| 110 | Me$_2$CHCH$_2$ | PhCH$_2$OC(O) | 439 | 3.2 | 1.6 | >40 | |
| 111 | Pr$_2$CH | Me$_3$COC(O) | 447 | 0.37 | 0.24 | 4.0* | |
| 112 | Me$_2$CHCH$_2$ | Me$_3$COC(O) | 405 | 1.8 | 1.2 | 3.2 | |
| 113 | PhCH$_2$ | 3-pyridyl-CH$_2$C(O) | 458 | 2.0 | | | >50* |
| 114 | PhCH$_2$ | 4-pyridyl-CH$_2$C(O) | 458 | 0.80 | | | 23 |

TABLE 1-continued

Compound of formula 1 having the structure

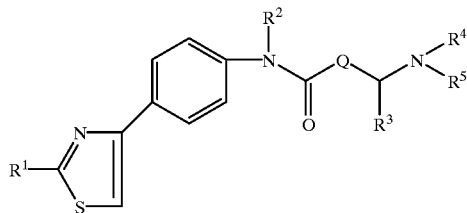

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu$M) | HSV-1 $EC_{50}$ ($\mu$M) | ELISA CMV $EC_{50}$ ($\mu$M) | PRA CMV $EC_{50}$ ($\mu$M) |
|---|---|---|---|---|---|---|---|
| 115 | PhCH$_2$ | 3-thienyl-C(O) | 449 | | | | 49 |
| 116 | PhCH$_2$ | 2-thienyl-CH$_2$C(O) | 463 | | | | 19 |
| 117 | PhCH$_2$ | 3-thienyl-CH$_2$C(O) | 463 | | | | 35 |
| 118 | (2-FPh)CH$_2$ | 4-pyridyl-C(O) | 462 | 0.047 | | | 60 |
| 119 | PhCH$_2$ | 2-amino-thiazol-4-yl-CH$_2$C(O) | 479 | 0.68 | | 25 | |
| 120 | PhCH$_2$ | PhOCH$_2$C(O) | 473 | 0.54 | | | 15 |
| 121 | PhCH$_2$ | 2,6-diMe-PhOCH$_2$C(O) | 501 | 0.49 | | | >31 |
| 122 | PhCH$_2$ | 4,6-diMe-pyrimidin-2-yl-SCH$_2$C(O) | 519 | | | | 3.3 |
| 123 | PhCH$_2$ | 1-Me-piperidin-4-yl-C(O) | 464 | >50 | | 41 | |

TABLE 1-continued

Compound of formula 1 having the structure

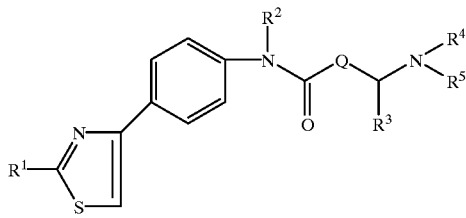

wherein R¹ is NH₂, R² and R³ are each H, Q is absent and R⁴ and R⁵ are designated as follows:

| ENTRY No | R⁴ | R⁵ | FAB/MS (m/z) (MH)⁺ | HSV-1 IC₅₀ (μM) | HSV-1 EC₅₀ (μM) | ELISA CMV EC₅₀ (μM) | PRA CMV EC₅₀ (μM) |
|---|---|---|---|---|---|---|---|
| 124 | (4-FPh)CH₂ | 2-pyridyl-CH₂C(O) | 476 | | | | 28 |
| 125 | PhCH₂CH₂ | 4-pyridyl-C(O) | 458 | 0.159 | | | 80 |
| 126 | (3-FPh)CH₂ | 2-pyridyl-CH₂C(O) | 476 | | | | 35 |
| 127 | (2-MePh)CH₂ | 2-pyridyl-CH₂C(O) | 472 | 0.99 | | 8.8 | 25* |
| 128 | (2-MePh)CH₂ | 2-thienyl-C(O) | 463 | | | | 28 |
| 129 | (2-MePh)CH₂ | 2,6-Me₂-Ph-OCH₂C(O) | 515 | | | | 12 |
| 130 | (2-MePh)CH₂ | 4,6-Me₂-pyrimidin-2-yl-SCH₂C(O) | 533 | | | | 8.8 |
| 131 | (2-MePh)CH₂ | 2-thienyl-CH₂C(O) | 477 | | | | 16 |
| 132 | (2-MePh)CH₂ | 3-thienyl-CH₂C(O) | 477 | | | | 14 |

TABLE 1-continued

Compound of formula 1 having the structure

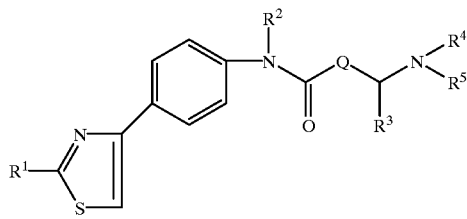

wherein $R^1$ is $NH_2$, $R^2$ and $R^3$ are each H, Q is absent and $R^4$ and $R^5$ are designated as follows:

| ENTRY No | $R^4$ | $R^5$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 133 | (2-MePh)CH$_2$ | thiophene-3-C(O) | 463 | | | | 17 |
| 134 | Ph-(S)—CHMe | pyridine-3-C(O) | 458 | 0.26 | | | 18 |
| 135 | Ph-(S)—CHMe | pyridine-2-CH$_2$C(O) | 472 | 0.78 | | | 38 |
| 136 | Ph-(R)—CHMe | pyridine-2-CH$_2$C(O) | 472 | 4.2 | | | 31 |
| 137 | Ph-(R)—CHMe | pyridine-4-C(O) | 458 | 0.98 | | | 49 |
| 138 | cyclohexyl-CH$_2$ | Me-N-piperidine-4-C(O) | 470 | >50 | | 31.6 | |
| 139 | cyclohexyl-CH$_2$ | pyridine-2-CH$_2$C(O) | 464 | 0.77 | | | 20 |
| 140 | Me$_2$NCH$_2$CH$_2$ | cyclohexyl-C(O) | 430 | 48 | 9.2 | 1.4 | 29 |
| 141 | Pr$_2$CH | PhCH$_2$OC(O) | 481 | 4 | 3.5 | >121 | |
| 142 | Me$_3$CCH$_2$ | Me$_3$COC(O) | 419 | 6.3 | 2.4 | 4.0 | |
| 143 | PhCH$_2$ | PhCH$_2$NHS(O)$_2$ | 508 | 0.8 | 1.0 | >64 | |

*Cytotoxic at this concentration
**Includes isotopic peak due to chlorine

TABLE 2

Compound of formula 1 having the structure

[Structure: thiazole (R¹ at 2-position, S) connected to phenyl (4-position) with N(R²)-C(=O)-O-CH(R³)-N(R⁴)(R⁵)]

wherein R¹ is NH₂, R₂ and R₃ each is H, and Q, R4 and R5 are designated as follows:

| ENTRY No | Q | R⁴ | R⁵ | FAB/MS (m/z) (MH)⁺ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|---|
| 1 | CH₂ | H | PhCH₂ | 353 | 21 | 6 | 3.2 | 30 |
| 2 | CH₂ | PhCH₂ | PhCH₂ | 443 | 1.2 | 2.2 | 0.55 | 4.7 |
| 3 | CH₂ | PhCH₂ | PhC(O) | 457 | 2.1 | 2.2 | 1.2 | 9.2 |
| 4 | CH₂ | H | (3-FPh)CH₂ | 371 | 5.2 | 2.2 | 6.6 | >3.7* |
| 5 | CH₂ | (3-FPh)CH₂ | PhC(O) | 447 | 1.3 | 2.0 | 5.8 | 8.8* |
| 6 | CH₂ | PhCH₂ | 3-pyridyl-C(O) | 458 | 5.7 | 4.8 | 1.1 | 22 |
| 7 | CH₂ | PhCH₂ | 4-pyridyl-C(O) | 458 | 7.6 | 3.2 | 7.8 | 42 |
| 8 | CH₂ | PhCH₂ | cyclohexyl-C(O) | 463 | 1.7 | 1.1 | 8.6 | 13* |
| 9 | CH₂ | H | indan-1-yl | 379 | 4.0 | 0.95 | 6.0 | >10.4 |
| 10 | CH₂ | H | indan-2-yl | 379 | 21 | 3.9 | 7.5 | 14* |
| 11 | CH₂ | indan-2-yl | 3-pyridyl-C(O) | 484 | 15 | 4 | 15 | 20 |
| 12 | CH₂ | | | 484 | 10 | 7.6 | 6.5 | 8 |
| 13 | CH₂ | indan-2-yl | Me₃COC(O) | 479 | 2.6 | 3.4 | 3.7 | 9* |
| 14 | CH₂ | indan-1-yl | Me₃COC(O) | 479 | 1.7 | 1.8 | 0.2 | >28 |
| 15 | CH₂ | PhCH₂ | Me₃COC(O) | 453 | 0.28 | 0.64 | 11.3 | 9 |
| 16 | CH₂ | PhCH₂ | PhCH₂OC(O) | 487 | 1.8 | 2.6 | 7 | 8* |

TABLE 2-continued

Compound of formula 1 having the structure wherein R¹ is NH₂, R₂ and R₃ each is H, and Q, R4 and R5 are designated as follows:

| ENTRY No | Q | R⁴ | R⁵ | FAB/MS (m/z) (MH)⁺ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|---|
| 17 | CH₂ | PhCH₂ | cyclohexyl-CH₂ | 449 | 0.76 | 1.8 | 4.7 | >5 |
| 18 | CH₂ | Ph-(S)—CHMe | Me₃COC(O) | 467 | 1.0 | 1.6 | 2.9 | 3.3 |
| 19 | CH₂ | PhCH₂ | Ph-(S)—CHMe | 457 | 0.46 | 0.89 | 3.1 | 4 |
| 20 | CH₂ | H | Ph-(S)—CHMe | 367 | 7.2 | 1.3 | 0.8 | 13 |
| 21 | CH₂ | cyclohexyl-CH₂ | Me₃COC(O) | 459 | 0.028 | 0.45 | 4.2 | 6.5 |
| 22 | CH₂ | H | cyclohexyl-CH₂ | 359 | 29 | 6 | 4.8 | >6* |
| 23 | CH₂ | H | Pr₂CH | 361 | 45 | 6 | 4.0 | >9* |
| 24 | CH₂ | cyclohexyl-CH₂ | pyridin-3-yl-C(O) | 464 | 1.2 | 1.7 | 0.45 | 31 |
| 25 | CH₂ | H | Ph-(R)—CHMe | 367 | 13.6 | 2.6 | 1.0 | >6 |
| 26 | CH₂ | PhCH₂ | pyridin-2-yl-CH₂ | 444 | | | | 14 |
| 27 | CH₂ | PhCH₂ | pyrrolidin-1-yl-CH₂CH₂ | 450 | | | | 15 |
| 28 | CH₂ | Ph-(S)—CHMe | Me | 367 | 7.9 | 2.0 | 18 | |
| 29 | CH₂ | PhCH₂ | pyridin-3-yl-CH₂ | 444 | | | | 14 |
| 30 | CH₂ | PhCH₂ | 2-HO-C₆H₄-CH₂ | 459 | | | | 13 |

*Cytotoxic at this concentration

TABLE 3

Compound of formula 1 having the structure

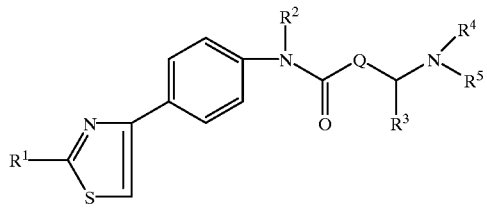

wherein R³ is H, Q is absent and R¹, R², R⁴ and R⁵ are designated as follows:

| ENTRY No | R¹ | R² | R⁴ | R⁵ | FAB/MS (m/z) (MH)⁺ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|---|---|
| 1 | NH₂ | Me | PhCH₂ | cyclohexyl-C(O) | 463 | 0.053 | 0.016 | >46 | 24 |
| 2 | NH₂ | Me | PhCH₂ | 4-pyridyl-C(O) | 458 | 1.5 | 0.34 | 78 | |
| 3 | NH₂ | Me | H | PhCH₂ | 353 | 13 | 4 | | 80 |
| 4 | Me | H | PhCH₂ | cyclohexyl-C(O) | 448 | 0.19 | 0.12 | 12 | |
| 5 | H | H | PhCH₂ | cyclohexyl-C(O) | 434 | 0.10 | 0.012 | >63 | 16 |
| 6 | NHMe | H | PhCH₂ | PhC(O) | 457 | 0.33 | 0.012 | 51 | 16 |
| 7 | NHMe | H | H | PhCH₂ | 353 | 15.0 | 4.1 | | |
| 8 | NHMe | H | PhCH₂ | cyclohexyl-C(O) | 463 | 0.05 | 0.002 | 9.0 | |
| 9 | NHMe | H | cyclohexyl-CH₂ | 3-pyridyl-C(O) | 464 | 10.0 | 1.3 | 5.0 | |
| 10 | NHMe | H | PhCH₂ | Me₃COC(O) | 453 | 0.31 | 0.008 | 1.1 | |
| 11 | NMe₂ | H | PhCH₂ | PhC(O) | 471 | >50 | 0.024 | 3.5 | 18 |
| 12 | NMe₂ | H | H | PhCH₂ | 367 | >50 | 21 | >79 | |
| 13 | NMe₂ | H | H | cyclohexyl-CH₂ | 373 | >50 | >4 | 36 | |
| 14 | NMe₂ | H | PhCH₂ | 4-pyridyl-C(O) | 472 | >50 | 0.5 | 20 | |
| 15 | NMe₂ | H | PhCH₂ | 3-pyridyl-C(O) | 478 | >50 | >23 | 28 | |

TABLE 3-continued

Compound of formula 1 having the structure

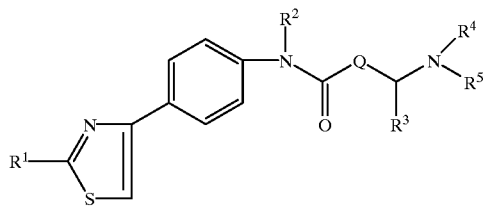

wherein R³ is H, Q is absent and R¹, R², R⁴ and R⁵ are designated as follows:

| ENTRY No | R¹ | R² | R⁴ | R⁵ | FAB/MS (m/z) (MH)⁺ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|---|---|
| 16 | NMe₂ | H | PhCH₂ | Me₃COC(O) | 467 | >50 | 0.009 | 4.8 | |
| 17 | NMe₂ | H | cyclohexyl-CH₂ | Me₃COC(O) | 473 | >50 | >8 | 4 | |
| 18 | Me-C(O)NH | H | PhCH₂ | CH₃C(O) | 423 | >100 | >30 | 2.8 | >81 |
| 19 | Me-C(O)NH | H | PhCH₂ | 4-pyridyl-C(O) | 486 | >50 | 9 | 28 | |
| 20 | Me₂CH | H | PhCH₂ | PhC(O) | 470 | >50 | >25 | 3.3 | 70 |
| 21 | Me₃CO—C(O)NH | H | PhCH₂ | 4,6-dimethylpyrimidin-2-yl-SCH₂C(O) | 619 | | | | 1.2 |
| 22 | Me₃CO—C(O)NH | H | Ph-(R)—CHMe | cyclohexyl-C(O) | 563 | | | | 1.3 |
| 23 | Me₃CO—C(O)NH | H | Ph-(R)—CHMe | 2-pyridyl-CH₂C(O) | 572 | | | | 2.8 |
| 24 | Me₃CO—C(O)NH | H | Ph-(R)—CHMe | 4-pyridyl-C(O) | 558 | | | | 3.7 |
| 25 | Me₃CO—C(O)NH | H | Ph-(S)—CHMe | 2-pyridyl-CH₂C(O) | 572 | | | | 2.7 |
| 26 | Me-C(O)NH | H | Ph-(R)—CHMe | cyclohexyl-C(O) | 505 | | | | 15 |

TABLE 4

Compound of formula 1 having the structure

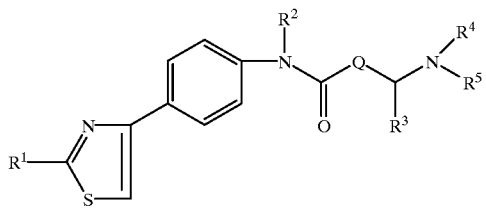

| | wherein R² and R³ each is H, Q is CH₂ and R¹, R⁴ and R⁵ are designated as follows: | | | FAB/MS (m/z) | HSV-1 $IC_{50}$ | HSV-1 $EC_{50}$ | ELISA CMV $EC_{50}$ | PRA CMV $EC_{50}$ |
|---|---|---|---|---|---|---|---|---|
| ENTRY No | R¹ | R⁴ | R⁵ | (MH)⁺ | ($\mu$M) | ($\mu$M) | ($\mu$M) | ($\mu$M) |
| 1 | Me₃COC(O)NH | PhCH₂ | PhCH₂ | 543 | | | | 1.6 |
| 2 | Me₃CNHC(O)NH | PhCH₂ | PhCH₂ | 542 | | | | 1.5 |

TABLE 5

Compound of formula 1 having the structure

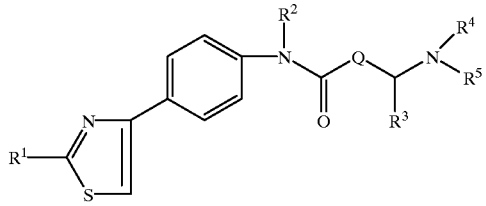

| | wherein R¹ is amino, R² is H, Q is absent and R³, R⁴ and R⁵ are designated as follows: | | | FAB/MS (m/z) | HSV-1 $IC_{50}$ | HSV-1 $EC_{50}$ | ELISA CMV $EC_{50}$ | PRA CMV $EC_{50}$ |
|---|---|---|---|---|---|---|---|---|
| ENTRY No | R³ | R⁴ | R⁵ | (MH)⁺ | ($\mu$M) | ($\mu$M) | ($\mu$M) | ($\mu$M) |
| 1 | (S)-PhCH₂ | H | cyclohexyl-C(O) | 449 | 0.052 | 0.079 | 14* | |
| 2 | (R)-PhCH₂ | H | cyclohexyl-C(O) | 449 | 0.64 | 0.17 | 52 | |
| 3 | (S)-PhCH₂ | H | Me₃COC(O) | 439 | 0.046 | 0.016 | 0.14 | 24 |
| 4 | (R)-PhCH₂ | H | Me₃COC(O) | 439 | 1.5 | 0.57 | 0.25 | 22 |
| 5 | (S)-PhCH₂ | Me | cyclohexyl-C(O) | 463 | 0.22 | 0.15 | 9.5 | |
| 6 | (S)-PhCH₂ | H | PhCH₂ | 429 | 1.06 | 0.83 | 0.14 | 7 |
| 7 | (R)-PhCH₂ | H | PhCH₂ | 429 | 6.6 | 2.1 | >9 | |
| 8 | (S)-PhCH₂ | H | Me | 353 | 45 | 14 | 1.1 | 33 |
| 9 | (R)-PhCH₂ | PhCH₂ | cyclohexyl-C(O) | 539 | 0.052 | 0.29 | 4.0 | 8.7 |
| 10 | (S)-PhCH₂ | Me | Me₃COC(O) | 453 | 0.090 | 0.059 | 2.5 | 12 |

TABLE 5-continued

Compound of formula 1 having the structure

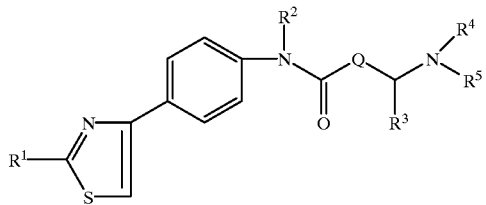

|  | wherein $R^1$ is amino, $R^2$ is H, Q is absent and $R^3$, $R^4$ and $R^5$ are designated as follows: | | | FAB/MS (m/z) | HSV-1 IC$_{50}$ | HSV-1 EC$_{50}$ | ELISA CMV EC$_{50}$ | PRA CMV EC$_{50}$ |
|---|---|---|---|---|---|---|---|---|
| ENTRY No | $R^3$ | $R^4$ | $R^5$ | (MH)$^+$ | ($\mu$M) | ($\mu$M) | ($\mu$M) | ($\mu$M) |
| 11 | (S)-PhCH$_2$ | PhCH$_2$ | cyclohexyl-C(O) | 539 | 0.40 | 0.51 | 1.4 | 8 |
| 12 | (S)-Me | H | PhCH$_2$ | 353 | 1.3 | 0.82 | 4.1 |  |
| 13 | (R)-Me | H | PhCH$_2$ | 353 | 2.0 | 2.0 | 14 |  |
| 14 | (S)-Me | PhCH$_2$ | cyclohexyl-C(O) | 463 | 0.11 | 0.009 | 10 |  |
| 15 | (R)-Me | PhCH$_2$ | cyclohexyl-C(O) | 463 | 0.041 | 0.006 | 3.2 |  |
| 16 | (S)-Me | PhCH$_2$ | Me$_3$COC(O) | 453 | 0.46 | 0.079 | 2.8 |  |
| 17 | (R)-Me | PhCH$_2$ | Me$_3$COC(O) | 453 | 0.11 | 0.055 | 7.6 |  |
| 18 | (R)-PhCH$_2$ | H | Me | 353 | 24.5 |  |  | >48 |
| 19 | (S)-PhCH$_2$ | H | Me$_3$CCH$_2$C(O) | 437 | 0.051 | 0.040 | 3.8 | 21* |
| 20 | (S)-PhCH$_2$ | H | Me$_3$CC(O) | 423 | 1.3 | 0.60 | 10 |  |
| 21 | (S)-PhCH$_2$ | H | MeC(O) | 381 | 3.1 | 4.7 | 4.4 |  |
| 22 | (S)-PhCH$_2$ | H | Me$_2$CHOC(O) | 425 | 0.83 | 0.25 | 18 |  |
| 23 | (S)-PhCH$_2$ | H | PhCH$_2$OC(O) | 473 | 0.60 | 0.094 |  |  |
| 24 | (S)-cyclohexyl-CH$_2$ | H | Me$_2$COC(O) | 445 | 0.017 | 0.043 | 8.1 |  |
| 25 | (S)-PhCH$_2$ | H | morpholino-S(O)$_2$ | 488 | 0.17 | 0.10 | 0.6 | 55 |
| 26 | (S)-pyridin-3-yl-CH$_2$ | H | Me$_3$COC(O) | 440 | 0.13 | 0.043 | 19.9 |  |

*Cytotoxic at this concentration

TABLE 6

Compound of formula 1 having the structure

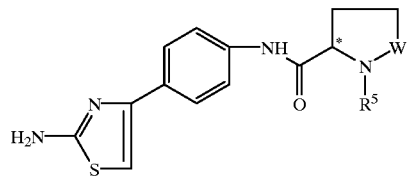

wherein W and R⁵ are designated as follows:

| ENTRY No | W | R⁵ | Configuration* | FAB/MS (m/z) (MH)⁺ | HSV-1 $IC_{50}$ ($\mu$M) | HSV-1 $EC_{50}$ ($\mu$M) | ELISA CMV $EC_{50}$ ($\mu$M) | PRA CMV $EC_{50}$ ($\mu$M) |
|---|---|---|---|---|---|---|---|---|
| 1 | C(O) | PhCH$_2$ | R | 393 | 12 | 3.4 | 0.25 | 80 |
| 2 | C(O) | PhCH$_2$ | S | 393 | 6.2 | 2.6 | 22 | 50 |
| 3 | C(O) | C$_6$H$_{11}$-CH$_2$ | R | 399 | 6.2 | 2.1 | 1.4 | 45 |
| 4 | CH$_2$ | Me$_3$COC(O) | S |  | 0.46 | 0.21 | >64 |  |
| 5 | CH$_2$ | PhC(O) | S | 393 | 1.6 | 0.17 | 63 | >89 |
| 6 | CH$_2$ | C$_6$H$_{11}$-C(O) | S | 399 | 0.052 | 0.016 | 28 | 22 |
| 7 | CH$_2$ | PhCH$_2$ | S | 379 | 1.5 | 1.1 | >33 |  |
| 8 | CH$_2$ | Me$_3$COC(O) | R | 389 | 7.5 | 1.8 | 11 | >83 |
| 9 | CH$_2$ | PhC(O) | R | 393 | 1.6 | 0.59 | 0.30 | >88 |
| 10 | CH$_2$ | C$_6$H$_{11}$-C(O) | R | 399 | 0.13 | 0.025 | 0.60 | 48 |

*Configuration of the asymmetric carbon atom linked to the —(CH$_2$)$_2$W— group In addition to the above results, certain Group 1 compounds have been tested against cutaneous HSV-1 infection in the SKH-1 hairless mouse model (P. H. Lee et al., supra). In this instance, viral pathology was monitored using a subjective scoring system and infection was initiated by spreading a viral inoculum (HSV-1 KOS, 7.3×10⁷ PFU) over punctured skin. Following suspension/dissolution of the test compound in 0.03N aqueous HCl, oral administration for five days tid, commencing three hours post infection, resulted in a significant reduction of viral pathology for the Group 1 compounds from TABLE 1 as follows:

TABLE 1

| Entry No. | $ED_{50}$ (mg/kg/day) |
|---|---|
| 58 | 31 |
| 36 | 51 |
| 29 | 56 |
| 49 | 129 |

Antiviral activity for Group 1 compounds was also observed in the mouse genital model of R. W. Sidwell et al., supra. Vaginal HSV-2 infection in the Swiss Webster mouse was initiated by vaginal irritation and instillation of HSV-2 (HSV-2 HG-52, 1×10⁷ PFU). Viral pathology was measured as described above. Following oral administration in the above vehicle, and commencing three hours post infection, the following reductions in viral pathology were observed for the Group 1 compounds in TABLE 1: Entry 29 produced a dose-dependent ($ED_{50}$=60 mg/kg/day) reduction of viral pathology and Entry 28 at 100 mg/kg/day produced a 30% reduction of viral pathology.

Furthermore, certain Group 1 compounds have been subjected to cutaneous testing. The compounds were formulated as a 3% (w/w) composition in an emulsion cream having the following composition: Pegoxal 7 Stearate® (a mixture of different molecular weight steric acid esters of polyethylene glycol) 14%; Peglicol 5 Oleate® (glycosylated glycerides) 3%; light mineral oil 2%; Transcutol® (diethoxy glycol) 10%; parabens (a mixture of methyl and propyl esters of 4-hydroxybenzoic acid) 0.15%; and deionized water qs to 100%). Cutaneously HSV-1 infected hairless mice (see above for protocol) were treated qid beginning 3 h post inoculation for five days by liberally applying the cream over the inoculation area. Evidence of disease was scored as described above. The following results were obtained.

| Compound (3% w/w Cream) | % Reduction of Cutaneous Pathology |
|---|---|
| Entry No. 1 | 95 |
| Entry No. 28 | 79 |
| Entry No. 24 | 88 |
| Entry No. 29 | 95 |
| Entry No. 29 (Treatment 24 h post inoculation) | 23 |

In addition the dose-dependence of Entry No. 29 following topical application to the skin was evaluated and the $ED_{50}$ was found to be 0.1% w/w.

Still furthermore, oral doses of Entry No. 29 of Group 1 at 50 mg/kg/day and 100 mg/kg/day were active in the preceding mouse model when treatment was initiated at 65 h post inoculation. Also, topical treatment of cutaneous HSV-2 infections, namely HG-52 or the acyclovir resistant HSV-2 strain VK-1 (C. S. Crumpacker, New Engl. J. Med., 1989, 320, 293) infections, in the mouse model with the above noted 3% w/w formulation of Entry No. 29 was therapeutically effective, producing a 58 to 72% reduction of viral pathology.

Figure 2:
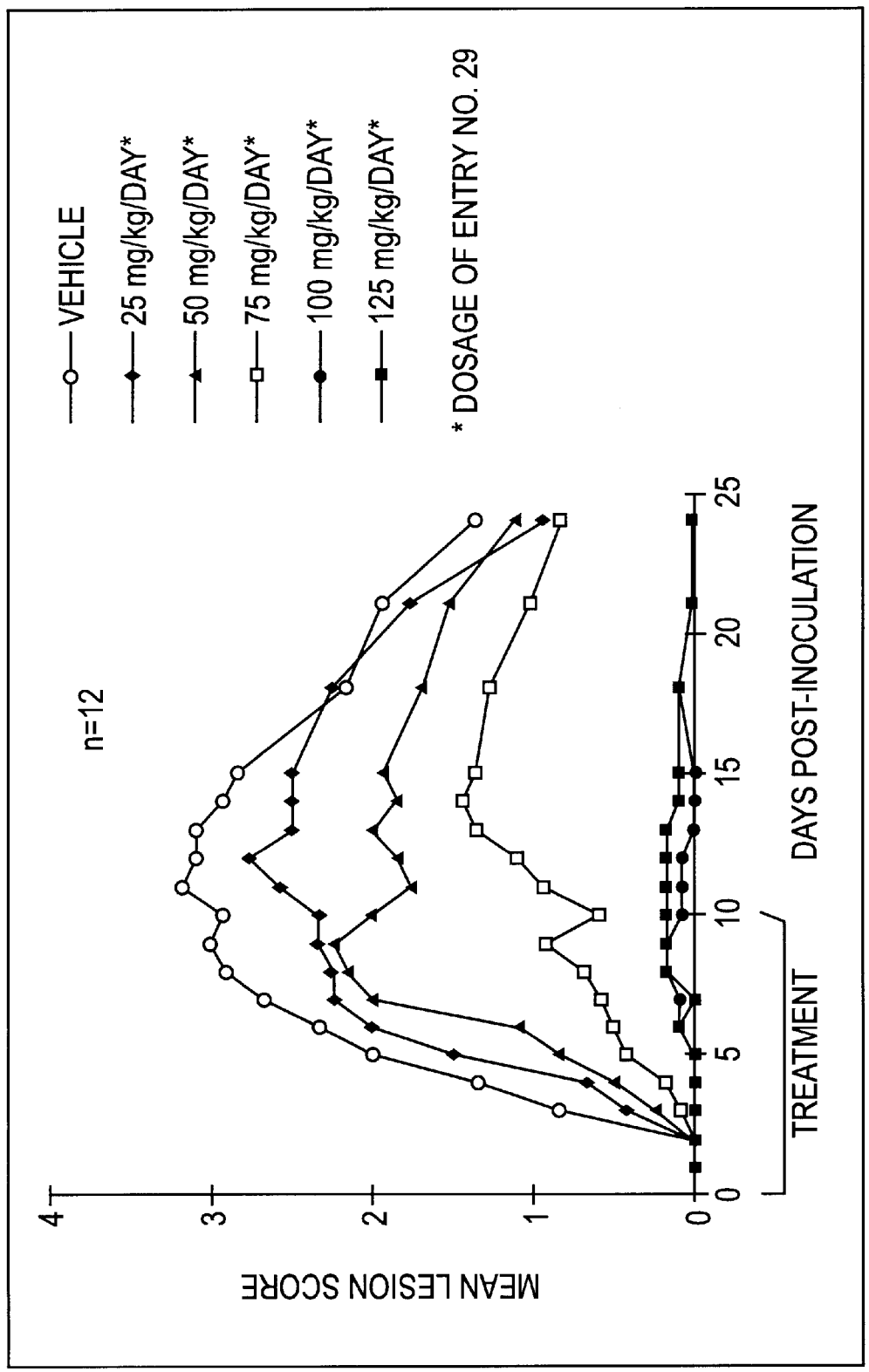
FIG. 2 shows a dose response curve for a thiazolylphenyl derivative of Group 1 against the acyclovir-resistant ESV-1 strain, noted for FIG. 1, in the same mouse model.
Figure 3:
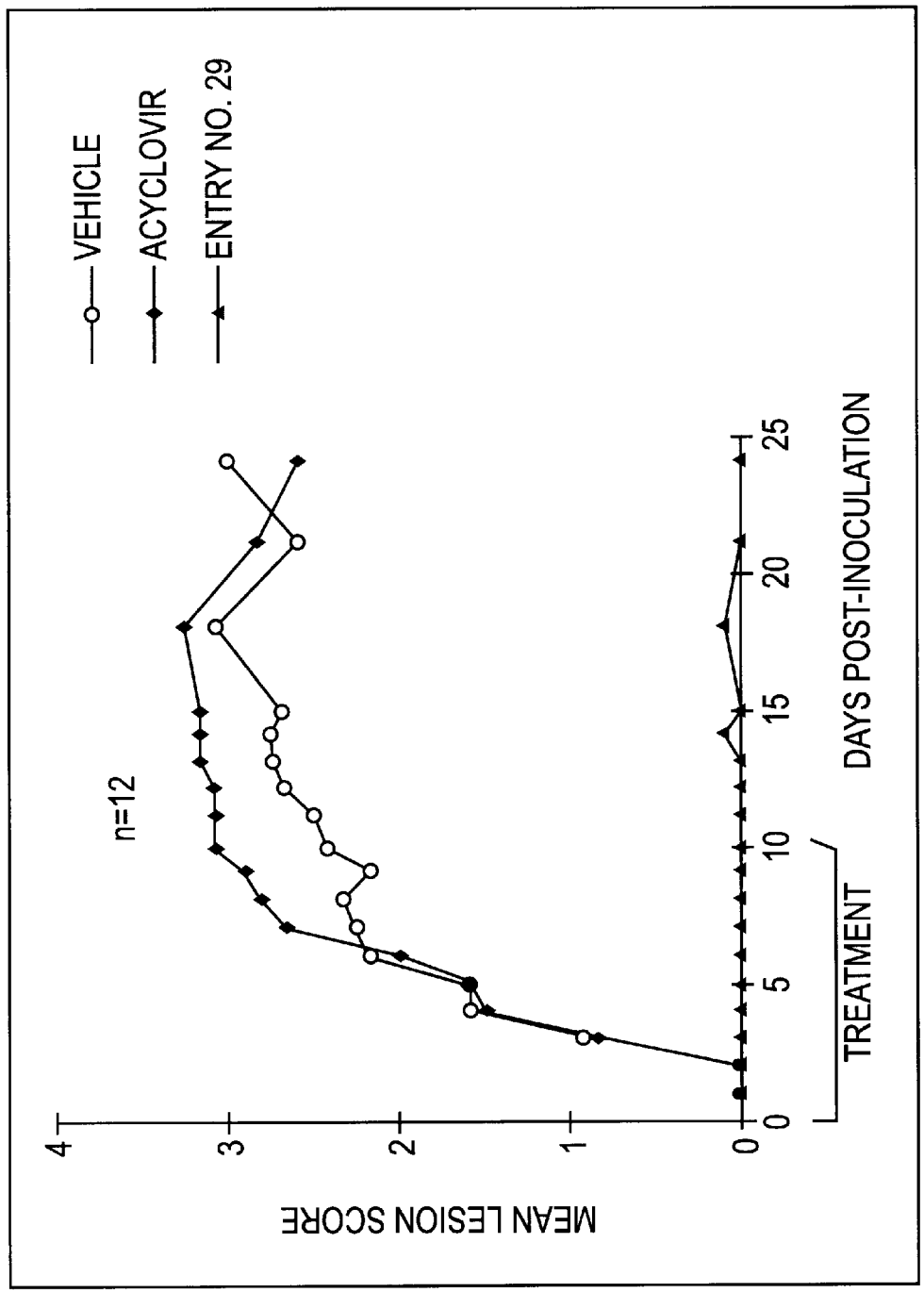
FIG. 3 graphically illustrates the therapeutic effect of acyclovir and a thiazolylphenyl derivative of Group 1 against an acyclovir-resistant HSV infection in the immunodeficient mouse model. The HSV strain in this instance is HSV-1 dlsptk.
Figure 4:
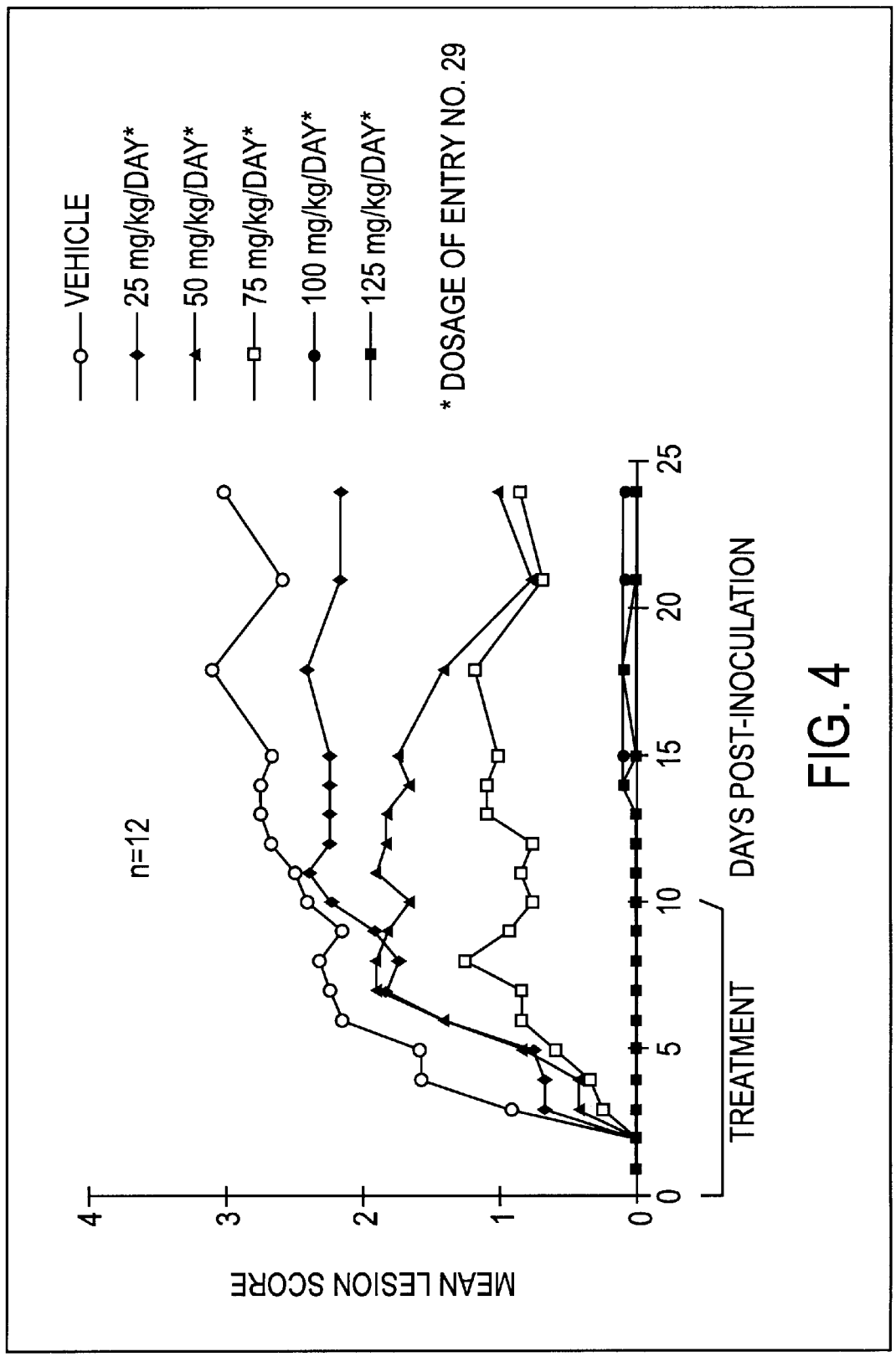
FIG. 4 shows a dose-response curve of a thiazolylphenyl derivative of Group 1 against the acyclovir-resistant strain noted for FIG. 3, in the same mouse model.

The therapeutic effectiveness of the compounds of Group 1 for treating acyclovir-resistant herpes infections in a mammal can be demonstrated by testing the compounds in an immunodeficient animal model (female nu/nu mice, 5–6 weeks old). Animals were cutaneously inoculated with $10^7$ PFU of HSV-1 acyclovir resistant mutant viruses. The resulting cutaneous lesions were scored according to a subjective scoring system. The compound of Group 1 (Entry No. 29 in table 1) was administered orally (gavage) in an acidified vehicle (0.033N aqueous HCl, tid for 10 days). Animals were similarly treated with acyclovir in 0.033N aqueous HCl or only with the vehicle (0.033N aqueous HCl). In animals infected with the HSV-1 acyclovir-resistant mutant strain PAA′5, Entry No. 29 dose-despondently reduced cutaneous lesions (FIGS. 1 and 2). The cutaneous lesions were almost abolished by treatment with Entry No. 29 at a dose of 100 mg/kg/day (-▲-), while acyclovir at the same dose (-♦-), or vehicle alone (-○-), had no effect on cutaneous lesions (FIG. 1). The dose-dependent effect of treatment with Entry No. 29 at 25 mg/kg/day (-♦-) 50 mg/kg/day (-▲-) 75 mg/kg/day (-□-), 100 mg/kg/day (-●-) or 125 mg/kg/day (-■-), compared to treatment with vehicle alone (-○-), is shown in FIG. 2. The $ED_{50}$ of Entry No. 29 was about 60 mg/kg/day. Similar experiments were done using the HSV-1 acyclovir-resistant mutant strain dlsptk (FIGS. 3 and 4). In this case the cutaneous lesions were again almost abolished by treatment with Entry No. 29 at a dose of 100 mg/kg/day (-▲-), while acyclovir at the same dose (-♦-), or vehicle alone (-○-), had no effect on cutaneous lesions (FIG. 3). The dose-dependent effect of treatment with Entry No. 29 at 25 mg/kg/day (-♦-), 50 mg/kg/day (-♦-), 75 mg/kg/day (-□-), 100 mg/kg/day (-●-) or 125 mg/kg/day (-■-), compared to treatment with vehicle alone (-○-), is shown in FIG. 4.

The acyclovir-resistant HSV-1 strains, pAA′5 and dlsptk, have been described by P. A. Furman et al., J. Virol., 1981, 40, 936 and by D. M. Coen et al., Proc. Natl. Acad. Sci., 1989, 86, 4736, respectively.

Group 2: N-(Thiazolylphenyl)ureido Derivatives

According to another embodiment of this invention, the present application refers to Group 2-N-(thiazolylphenyl) ureido derivatives having antiherpes activity. The selective action of these compounds against these viruses, combined with a wide margin of safety, renders the compounds desirable agents for combating herpes infections.

The N-(thiazolylphenyl)ureido derivatives of the present invention can be characterized structurally by the presence of N-{4-(4-thiazolyl)phenyl}ureido moiety. Compounds possessing such a moiety have been reported previously, for example:

K. D. Hargrave et al., J. Med. Chem., 1983, 26, 1158;

C. G. Caldwell et al., U.S. Pat. No. 4,746,669, issued May 24, 1988;

A. Wissner, European patent application 458,037, published Nov. 27, 1991; and

A. Leonardi et al., PCT patent application WO 95/04049, published Feb. 9, 1995.

The present N-(thiazolylphenyl)ureido derivatives can be distinguished readily from the prior art compounds in that they possess different chemical structures and biological activities.

The Group 2 N-(thiazolylphenyl)ureido derivatives of this invention can also be represented by formula 1a:

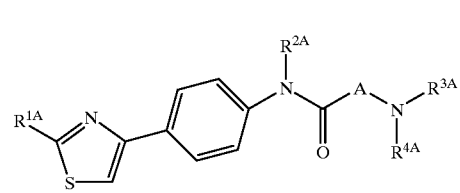

(1a)

wherein $R^{1A}$ has the same meaning as R as defined hereinbefore and $R^{2A}$, A, $R^{3A}$ and $R^{4A}$ are as defined hereinbefore.

A preferred set of Group 2 compounds of this invention is represented by Group 2-formula 1a wherein $R^{1A}$ is selected from the group consisting of hydrogen, lower alkyl, amino, lower alkylamino, di(lower alkyl)amino, lower alkanoylamino, (lower alkoxycarbonyl)amino, {(lower alkylamino)carbonyl}amino and 2-, 3- or 4-pyridinylamino; $R^{2A}$ is hydrogen, methyl or ethyl; A is absent or carbonyl; $R^{3A}$ is hydrogen, (1-8C)alkyl, is 2-hydroxyethyl, 3-hydroxypropyl,(1-3C)alkyl monosubstituted with cyano, phenyl-(1-3C)alkyl, phenyl-(1-3C)alkyl monosubstituted or disubstituted on the aromatic portion thereof with halo, hydroxy, di(lower alkyl)amino, lower alkoxy or lower alkyl; (lower cycloalkyl)-(lower alkyl) or (Het)-(lower alkyl) wherein Het is as defined hereinbefore; and $R^{4A}$ is (1-8C) alkyl, phenyl-(1-3C)alkyl, phenyl-(1-3C)alkyl monosubstituted or disubstituted on the aromatic portion thereof with halo, hydroxy, di(lower alkyl)amino, lower alkoxy or lower alkyl; 1-indanyl, 2-indanyl, 1-(hydroxymethyl)-2-phenylethyl, (lower cycloalkyl)-(1-3C)alkyl, Het as defined hereinbefore, (Het)-(1-3C)alkyl wherein Het is as defined hereinbefore or 3-1H-indolylethyl; or $R^{4A}$ is:

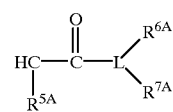

wherein L is oxygen or nitrogen, with the proviso that when L is oxygen, one of $R^{6A}$ or $R^{7A}$ is absent; $R^{5A}$ and $R^{6A}$ are independently selected from the group defined for $R^{3A}$ herein; and $R^{7A}$ is independently selected from the group defined for $R^{4A}$ herein; or $R^{3A}$ and $R^{4A}$ together with the nitrogen to which they are attached form an unsubstituted, monosubstituted or disubstituted five or six membered, monovalent heterocyclic ring containing one or two heteroatoms selected from the group consisting of N, O or S, wherein each substituent is selected independently from the group consisting of halo, hydroxy, lower alkoxy and lower alkyl; or a therapeutically acceptable acid addition salt thereof.

A more preferred set of Group 2 compounds are represented by Group 2-formula 1a wherein $R^{1A}$ is hydrogen, amino, methyl, methylamino, butylamino, dimethylamino, acetylamino, (1,1-dimethylethoxycarbonyl)amino, 2-pyridinylamino or 3-pyridinylamino; $R^{2A}$ is hydrogen or methyl; A is absent or carbonyl; $R^{3A}$ is hydrogen, methyl, ethyl, propyl, butyl, 2-methylpropyl, 2,2-dimethylpropyl, 1-propylbutyl, 2-hydroxyethyl, cyanomethyl, phenylmethyl, 2-phenylethyl, (4-chlorophenyl)methyl, (2-fluorophenyl) methyl, (3-fluorophenyl)methyl, (4-fluorophenyl)methyl, (4-(dimethylamino)phenyl}-methyl, (4-methoxyphenyl) methyl, (2-methylphenyl)methyl cyclopentylmethyl, cyclohexylmethyl, 2-cyclohexylethyl, 2-(4-morpholinyl) ethyl, 2-pyridinylmethyl, 3-pyridinylmethyl, 4-pyridinyl-methyl, 2-(2-pyridinyl)ethyl, 2-(3-pyridinyl)ethyl, 2-(4-pyridinyl)ethyl, 2-thienylmethyl or 3-thienyl-methyl; and $R^{4A}$ is 1,1-dimethylethyl, butyl, 2,2-dimethylpropyl, 1-propylbutyl, phenylmethyl, 1(R)-phenylethyl, 1(S)-phenylethyl, 2-phenylethyl, (4-chlorophenyl)methyl, (2-fluorophenyl)methyl, (3-fluorophenyl)methyl, (4-fluorophenyl)methyl, 4-(methoxyphenyl)methyl, {4-(dimethylamino)phenyl}-methyl, (2-methylphenyl)methyl, 1-indanyl, 2-indanyl, (S or R)-1-(hydroxymethyl)-2-phenylethyl, cyclopentylmethyl, cyclohexylmethyl, 1(S)-cyclohexylethyl, 1(R)-cyclohexylethyl, 2-cyclohexylethyl, 1-piperidinyl, 2-(4-morpholinyl)ethyl, 2-pyridinylmethyl, 3-pyridinyl-methyl, 4-pyridinylmethyl, 2-(2-pyridinyl) ethyl, 2-(3-pyridinyl)ethyl, 2-(4-pyridinyl)ethyl, 2-thienylmethyl, 3-(1H-imidazol-1-yl)propyl or 3-1H-indolylethyl; or $R^{4A}$ is:

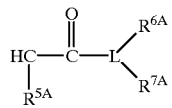

wherein L oxygen or nitrogen, with the proviso that when L is oxygen, one of $R^{6A}$ or $R^{7A}$ is absent; $R^{5A}$ and $R^{6A}$ are independently selected from the group defined for $R^{3A}$ herein; and $R^{7A}$ is independently selected from the group defined for $R^{4A}$ herein; or $R^{3A}$ and $R^{4A}$ together with the nitrogen atom to which they are attached form a pyrrolidino, piperidino, morpholino or thiomorpholino; or a therapeutically acceptable acid addition salt thereof.

A most preferred set of Group 2 compounds are represented by Group 2-formula 1a wherein $R^{1A}$ is amino, methylamino, dimethylamino or (1,1-dimethylethoxycarbonyl)amino; $R^{2A}$ is hydrogen; A is absent; $R^{3A}$ is hydrogen, methyl or butyl; and $R^{4A}$ is 1,1-dimethylethyl, butyl, 1-propylbutyl, phenylmethyl, 2-phenylethyl, 4-fluorophenylmethyl, 1-piperidinyl, 2-pyridinylmethyl, 2-(2-pyridinyl)-ethyl, 4-pyridinylmethyl, 3-(1H-imidazol-1-yl)-propyl, or $R^{4A}$ is:

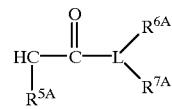

wherein L is nitrogen, $R^{5A}$ is phenylmethyl, $R^{6A}$ is methyl and $R^{7A}$ is 2-(2-pyridinyl)ethyl, or L is oxygen, $R^{5A}$ is phenylmethyl, $R^{6A}$ is absent and $R^{7A}$ is 1,1-dimethylethyl; or a therapeutically acceptable acid addition salt thereof.

Another most preferred set of Group 2 compounds are represented by Group 2-formula 1a wherein $R^{1A}$ is amino, methylamino, butylamino, dimethylamino, (1,1-dimethylethoxycarbonyl)amino, 2-pyridinylamino or 3-pyridinylamino; $R^{2A}$ is hydrogen; A is absent; $R^{3A}$ is hydrogen, methyl, ethyl, butyl, 2-hydroxyethyl, cyanomethyl or phenylmethyl; and $R^{4A}$ is butyl, phenylmethyl or 2-(4-pyridinyl)ethyl; or a therapeutically acceptable acid addition salt therof.

Still another most preferred set of Group 2 compounds are represented by Group 2-formula 1a wherein $R^{1A}$ is amino, $R^{2A}$ is hydrogen, A is carbonyl, $R^{3A}$ is butyl or phenylmethyl, and $R^{4A}$ is butyl or phenylmethyl, or a therapeutically acceptable acid addition salt therof.

Included within the scope of this invention is a pharmaceutical composition comprising an antiherpes virally effective amount of a compound of Group 2 as defined herein, or a therapeutically acceptable acid addition salt thereof, and a pharmaceutically or veterinarily acceptable carrier.

Still another aspect of this invention involves a method for treating acyclovir-resistant herpes infections in a mammal which comprises administering to the mammal an anti-acyclovir-resistant herpes effective amount of a compound of Group 2 as defined herein, or a therapeutically acceptable acid addition salt thereof.

Process for Preparing the Compounds of Group 2

The compounds of Group 2 can be prepared by a variety of processes. Description of such methods are found in standard textbooks such as "Annual Reports In Organic Synthesis—1994", P. M. Weintraub et al., Eds., Academic Press, Inc., San Diego, Calif., USA, 1994 (and the preceding annual reports), "Vogel's Textbook of Practical Organic Chemistry", B. S. Furniss et al., Eds., Longman Group Limited, Essex, UK, 1986, and "Comprehensive Organic Synthesis", B. M. Trost and I. Fleming, Eds., Pergamon Press, Oxford, UK, 1991, Volumes 1 to 8.

Generally speaking, the compounds of Group 2-formula 1a can be prepared by a process selected from the following processes (a), (b), (c) or (d):

(a) reacting in the presence of N,N'-carbonyldiimidazole a compound of the formula:

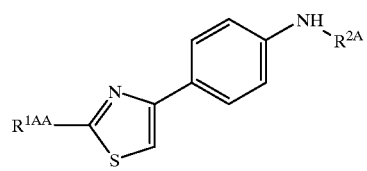

wherein $R^{1AA}$ is hydrogen, lower alkyl, (amino protecting group)-amino, (amino protecting group)-(lower alkylamino) or di(loweralkyl)amino and $R^{2A}$ is hydrogen or lower alkyl, with an amine of the formula:

wherein $R^{3A}$ and $R^{4A}$ are as defined herein, followed by, if required, removing any N-protecting groups and effecting standard transformations, to obtain the corresponding compound of Group 2-formula 1a wherein A is absent and $R^{1A}$, $R^{2A}$, $R^{3A}$ and $R^{4A}$ are as defined herein;

(b) reacting an isocyanate of the formula:

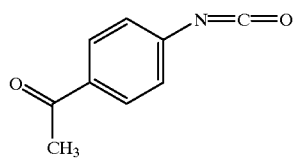

with an amine of the formula:

wherein $R^{3A}$ and $R^{4A}$ are as defined herein, to obtain the corresponding ureido derivative of the formula:

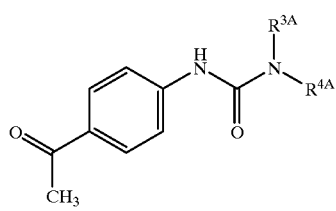

and either (i) reacting the latter ureido derivative with a thiourea derivative of the formula $H_2N\text{-}C(S)\text{-}R^{1BB}$ wherein $R^{1BB}$ is amino, lower alkylamino or di(lower alkyl)amino, and a halogen, selected from $Br_2$, $Cl_2$ or $I_2$, to obtain the corresponding compound of formula 1a wherein $R^{1A}$ is amino, lower alkylamino or di(lower alkyl)amino, $R^{2A}$ is hydrogen, A is absent and $R^{3A}$ and $R^{4A}$ are as defined herein; or (ii) reacting the latter ureido derivative with $Br_2$, $Cl_2$ or $I_2$ whereby the methyl ketone moiety of the ureido derivative is converted to a haloketone moiety to give the corresponding α-haloketone and reacting the α-haloketone with a thioamide of the formula $H_2N\text{-}C(S)\text{-}R^{1CC}$ wherein $R^{1CC}$ is hydrogen, lower alkyl, amino, lower alkylamino or di(lower alkyl)-amino to obtain the corresponding compound of formula 1a wherein $R^{1A}$ is hydrogen, lower alkyl, amino, lower alkylamino or di(lower alkyl)amino, $R^{2A}$ is hydrogen, A is absent and $R^{3A}$ and $R^{4A}$ are as defined herein; and, if required, eliminating from the instant product of (i) or (ii) any protective groups, and effecting standard transformations to obtain the corresponding compound of Group 2-formula 1a wherein A is absent, $R^{1A}$, $R^{3A}$ and $R^{4A}$ are as defined herein and $R^{2A}$ is hydrogen;

(c) reacting a compound of the formula:

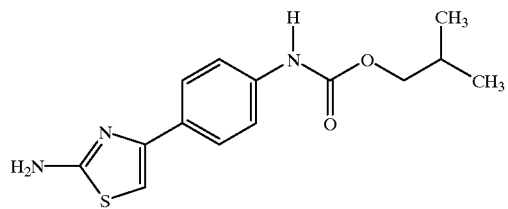

with an amine of the formula:

wherein $R^{3A}$ and $R^{4A}$ are as defined herein, to obtain the corresponding compound of formula 1a wherein $R^{1A}$ is amino, $R^{2A}$ is hydrogen, and $R^{3A}$ and $R^{4A}$ are as defined herein;

(d) reacting a compound of the formula:

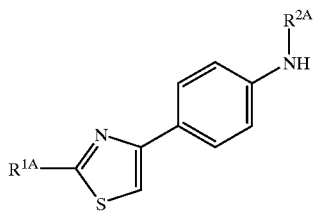

wherein $R^{1A}$ and $R^{2A}$ are as defined herein (prepared as described in the following Group 2-schemes 1 and 2), with a reagent of the formula:

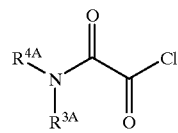

wherein $R^{3A}$ and $R^{4A}$ are as defined herein, to obtain the corresponding compound of Group 2-formula 1a wherein A is carbonyl, and $R^{1A}$, $R^{2A}$, $R^{3A}$ and $R^{4A}$ are as defined herein. The above reagent is prepared by reacting an equivalent amount of oxalyl chloride and the corresponding amine of the formula:

in the presence of a tertiary organic amine, for example diisopropylethylamine.

More explicitly, a practical and convenient procedure to prepare compounds of Group 2-formula 1a is illustrated by Group 2-scheme 1:

Group 2-Scheme 1

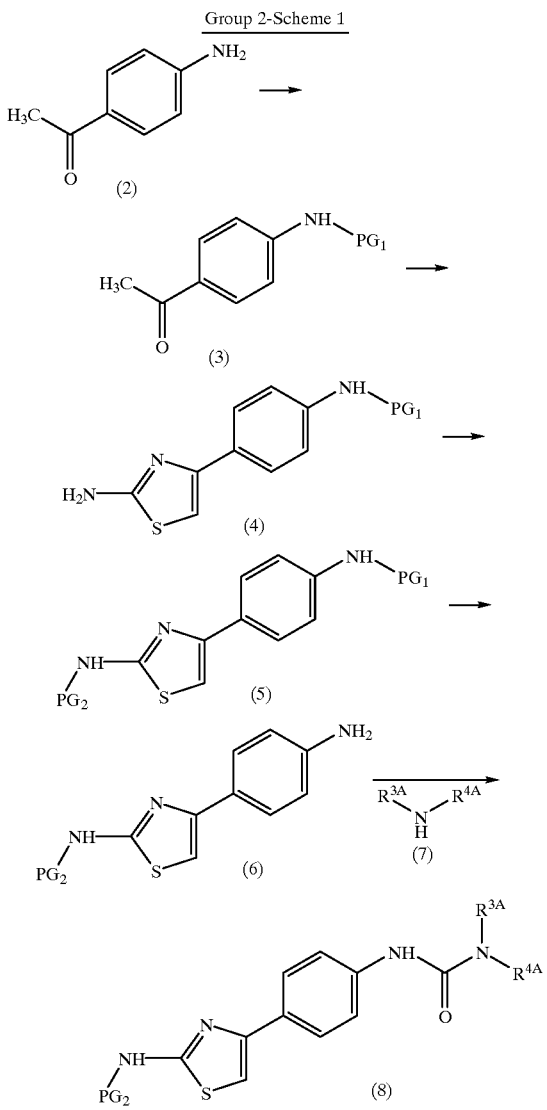

According to Group 2-scheme 1, the amino substituent of 4'-aminoacetophenone (2) is protected with a known amino protecting group $PG_1$ (for example 2,2,2-trichloroethoxycarbonyl, (phenylmethoxy)carbonyl, tert-butoxycarbonyl, {(4-methoxyphenyl)methoxy}-carbonyl or the like) to yield the amino protected compound of formula 3. The terminal methyl ketone moiety of the compound of formula 3 is converted to a 2-aminothiazolyl moiety by reaction with thiourea and iodine according to the method of R. M. Dodson and L. C. King, J. Amer. Chem Soc. 1945, 67, 2242 to give the corresponding aminothiazole derivative of formula 4. The 2-amino moiety of the 2-amino-thiazolyl moiety is then protected with an amino protecting group $PG_2$ to give the compound of formula 5. The amino protecting groups $PG_1$ and $PG_2$ are selected such that one of the groups can be selectively removed while leaving the other group intact. The amino protecting group $PG_1$ is then removed under conditions that do not affect the amino protecting group $PG_2$ to give the compound of formula 6. The compound of formula 6 is converted to the ureido derivative of formula 8 by reaction with N,N'-carbonyldiimidazole and an amine of formula 7 wherein $R^{3A}$ and $R^{4A}$ are as defined herein. In the instance where $NH-PG_2$ has the same significance as RIA as defined herein, then the compound of formula 8 is also compound of formula 1a. Alternatively, the compound of formula 8 can be deprotected to give the corresponding compound of formula 1a wherein $R^{1A}$ is amino. This latter product, albeit a compound of Group 2-formula 1a, can also serve as an intermediate for further elaboration by standard methods to yield other compounds of Group 2-formula 1a.

Another general procedure for preparing compounds of Group 2-formula 1a can be represented by Group 2-scheme 2:

Group 2-Scheme 2

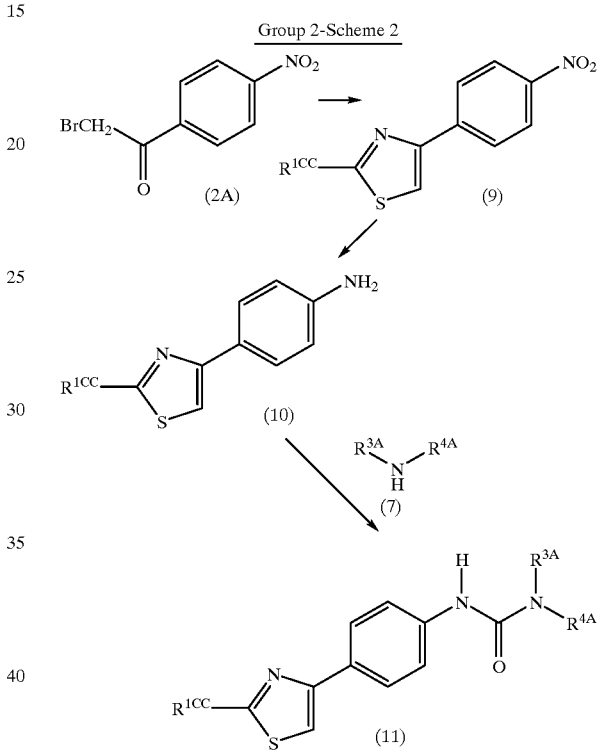

According to Group 2-scheme 2, 2-bromo-4'-nitroacetophenone of formula 2A is reacted with the appropriate thioamide of formula $H_2N-C(S)-R^{1CC}$ wherein $R^{1CC}$ is hydrogen, lower alkyl, amino, lower alkylamino or di(lower alkyl amino) to give the corresponding nitro derivative of formula 9. The nitro derivative of formula 9 is reduced with iron and hydrochloric acid to give the thiazolyl derivative of formula 10. The compound of formula 10 is converted to the ureido derivative of formula 11 by reaction with N,N'-carbonyldiimidazole and an amine of formula 7 wherein $R^{3A}$ and $R^{4A}$ are as defined herein. The ureido derivative of formula 11, which is also a compound of Group 2-formula 1a, can also serve as an intermediate for further elaboration by standard methods to yield other compounds of Group 2-formula 1a.

Another general procedure for preparing compounds of Group 2-formula 1a can be represented by Group 2-scheme 3:

83

Group 2 - Scheme 3

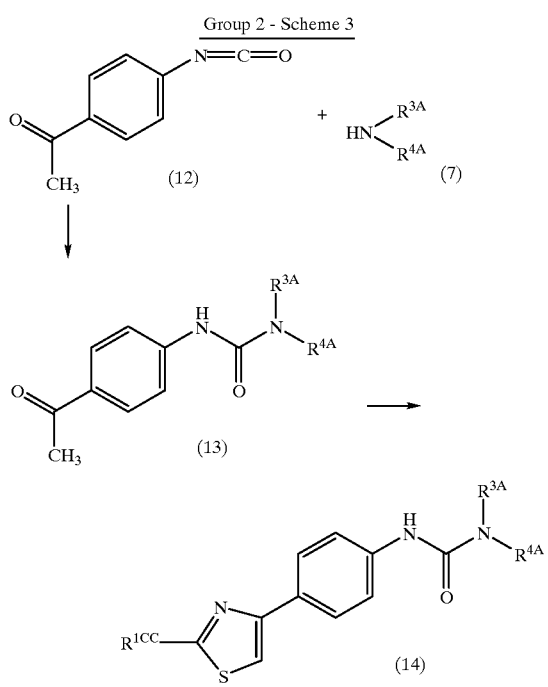

According to Group 2-scheme 3, the classical method for preparing a urea (see, for example, P. A. S. Smith, Organic Reactions, 1946, 3, 376–377) is applied by reacting directly a free N-terminal derivative of formula 7, wherein $R^{3A}$ and $R^{4A}$ are as defined herein, with 4-acetylphenyl isocyanate (12) to yield the ureido derivative of formula 13. The terminal ketone moiety of the ureido derivative of formula 13 is converted to a thiazolyl moiety by first reacting the ureido derivative 13 with $Br_2$, $Cl_2$ or $I_2$ to give the corresponding α-haloketone and reacting the α-haloketone with the appropriate thioamide as described before to give the corresponding thiazole derivative of formula 14 wherein $R^{1CC}$ is as defined herein, which is also a compound of Group 2-formula 1a. Alternatively, the ureido derivative of formula 13 can be directly converted to the thiazolyl derivative of formula 14 wherein $R^{1CC}$ is amino, lower alkylamino or di(lower alkyl)amino by heating the ureido derivative of formula 13 with an appropriate thiourea derivative of the formula $H_2N$—C(S)—$R^{1CC}$, wherein $R^{1CC}$ is amino, lower alkylamino or di(lower alkyl)amino, in the presence of $Br_2$, $Cl_2$ or $I_2$ according to the classical methods of R. M. Dodson and L. C. King, J. Amer. Chem. Soc. 1945, 67, 2242.

The compound of formula 14 can also serve as an intermediate for further elaboration by standard methods to yield other compounds of Group 2-formula 1a.

Another general procedure for preparing compounds of Group 2-formula 1a can be represented by Group 2-scheme 4:

Group 2 - Scheme 4

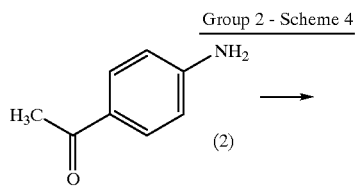

84

-continued

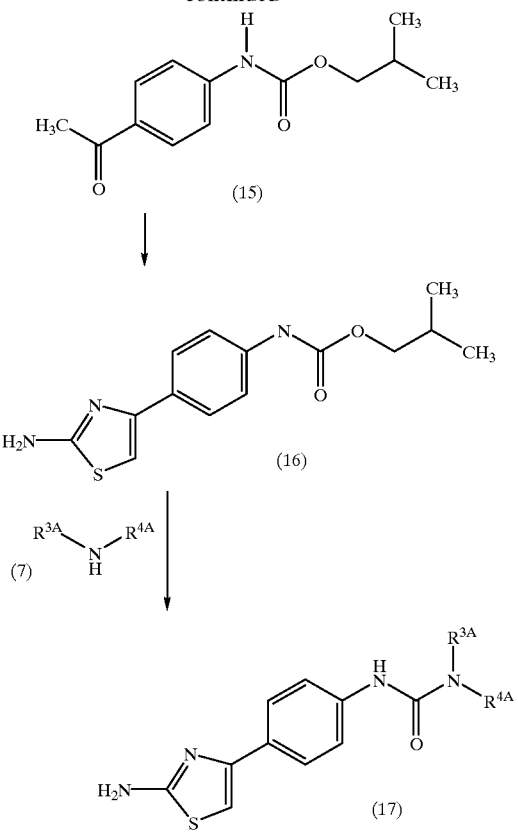

According to Group 2-scheme 4, the free amino moiety of 4'-aminoacetophenone (2) is converted to the carbamate derivative of formula 15 by reation with isobutyl chloroformate. The terminal methyl ketone moiety of the carbamate derivative of formula 15 is converted to 2-aminothiazolyl by reaction with thiourea and iodine according to the method of R. M. Dodson and L. C. King, J. Amer. Chem. Soc. 1945, 67, 2242 to give the corresponding aminothiazole derivative of formula 16. The aminothiazole derivative of formula 16 is reacted with an amine of formula 7, wherein $R^{3A}$ and $R^{4A}$ are as defined herein, to give the ureido derivative of formula 17, which is also a compound of formula 1a. The compound of formula 17 can also serve as an intermediate for further elaboration by standard methods to yield other compounds of Group 2-formula 1a.

Starting materials for the preceding processes are known or can be readily prepared from known starting materials. 4'-Aminoacetophenone (2) of Group 2-schemes 1 and 4 is available from the Aldrich Chemical Co., Milwaukee, Wis., USA. 2-Bromo-4'-nitroacetophenone also is available from the Aldrich Chemical Co. 4-Acetylphenyl isocyanate (12) of Group 2-scheme 3 is available from Lancaster Synthesis Inc., Windham, N.H., USA.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, the reaction can be successfully performed by conventional modification known to those skilled in the art, e.g. by appropriate protection of interfering groups, by changing to alternative conventional reagents, by routine modification of reaction conditions, or by modification illustrated in the examples herein.

Furthermore, if desired, the compound of Group 2-formula 1a can be obtained in the form of a therapeutically acceptable acid addition salt. Such salts can be considered as biological equivalent of the compounds of Group 2-formula 1a. Examples of such salts are those formed with hydrochloric acid, sulfuric acid, phosphoric acid, formic acid, acetic acid or citric acid.

Antiherpes Activity

The antiviral activity of the compounds of Group 2-formula 1a, or their corresponding therapeutically acceptable acid addition salts, can be demonstrated in the same manner as described hereinbefore for the compounds of Group 1-formula 1. Likewise, the compounds of Group 2-formula 1a, or their corresponding therapeutically acceptable acid addition salts, can be formulated and employed as antiviral agents in the same manner as described hereinbefore for the compounds of Group 1-formula 1.

The following examples (Group 2 examples) further illustrate this invention. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts ($\delta$) are reported in parts per million. The concentrations for the optical rotations are expressed in grams of the compound per 100 mL of solution. Abbreviations or symbols used in the examples are as defined hereinbefore.

GROUP 2 EXAMPLES

Example 1

N'-{4-(2-Amino-4-thiazolyl)phenyl}-N-methyl-N-{2-(2-pyridinyl)ethyl}urea (1a: $R^{1A}$=$NH_2$, $R^{2A}$=H, A is absent, $R^{3A}$=methyl and $R^{4A}$=2-pyridinylethyl)

(a) 2,2,2-Trichloroethyl N-{4-(2-amino-4-thiazolyl)phenyl}carbamate: 2,2,2-Trichloroethyl chloroformate (72.3 mL, 0.52 mol) was added (5 min) to an ice cold suspension of 4'-aminoacetophenone (67.6 g, 0.50 mol) and pyridine (50.5 mL, 0.62 mol) in $CH_2Cl_2$ (1 L). The reaction mixture was stirred at 0° for 15 minutes and then at room temperature (20–22°) for 45 min. The solvent was removed under reduced pressure. $Et_2O$ (500 mL) and 1N aqueous HCl (500 mL) were added to the residue. The resulting solid was collected by filtration, washed with $H_2O$ (1 L) and $Et_2O$ (1 L) and dried over $P_2O_5$ in a desiccator under reduced pressure for 15 h to yield the expected carbamate (137.8 g, 89% yield). A mixture of the crude carbamate (137.8 g, 0.44 mol), thiourea (135.0 g, 1.77 mol) and $I_2$ (202.6 g, 0.80 mol) in isopropanol (670 mL) was heated at reflux for 18 h. The reaction mixture was cooled to room temperature and EtOAc (1 L) was added. The solution was washed serially with $H_2O$ (2×600 mL), saturated aqueous $NaHCO_3$ (2×1 L) and $H_2O$ (2×1 L). A mixture of the organic layer and 4N aqueous HCl (750 mL) was stirred vigorously at room temperature for 1.5 h. $Et_2O$ (~800 mL) and $H_2O$ (~300 mL) were added to the mixture to facilitate stirring. The suspension was filtered and the solid was washed with a 1:1 mixture of EtOAc and $Et_2O$ (2 L). The solid was suspended in 20% aqueous NaOH (1.2 L) and the mixture was extracted with EtOAc (2 L). The EtOAc extract was washed with brine (700 mL), dried ($MgSO_4$), and concentrated under reduced pressure to yield 2,2,2-trichloroethyl N-{4-(2-amino-4-thiazolyl)phenyl}carbamate (117.7 g, 75% yield) as a pale yellow solid: $^1$H NMR (400 MHz, DMSO-$d_6$) $\delta$ 10.18 (s,1H), 7.74 (d,J=8.6 Hz, 2H), 7.51 (d,J=8.6 Hz, 2H), 7.01 (s, 2H) 6.88 (s, 1H), 4.95 (s, 2H); MS (FAB) m/z 366/368/370/372 (MH)$^+$.

(b) tert-Butyl N-{4-(4-Aminophenyl)-2-thiazolyl}carbamate: A solution of $(Boc)_2O$ (87.7 g, 0.40 mol) in $CH_2Cl_2$ (85 mL) and DMAP (4.08 g, 33.0 mmol) was added (10 min) to a cooled (0°) solution of the product of the preceding section a) (117.7 g, 0.33 mol) and pyridine (135.0 mL, 1.67 mol) in THF (500 mL) and $CH_2Cl_2$ (1 L). The reaction mixture was stirred at room temperature for 15 h. The reaction mixture was diluted with EtOAc (1.5 L) and $Et_2O$ (1 L). The resulting solution was washed serially with $H_2O$ (1 L), 10% (w/v) aqueous citric acid (2×500 mL), 1N aqueous HCl (500 mL), $H_2O$, saturated aqueous $NaHCO_3$ (2×1 L) and brine (1 L), dried ($MgSO_4$) and concentrated under reduced pressure to give a pale yellow foam (163 g). The latter foam (160 g, 0.34 mol) was diluted in 1,4-dioxane (1.72 L) and the solution cooled to 10°. Zn powder (224 g, 3.43 mol) and 1N aqueous HCl (3.4 L) was added to the cooled solution. The reaction mixture was mechanically stirred at room temperature for 1.5 h. The suspension was filtered and the collected material was washed with 1N aqueous HCl (~1 L). Aqueous 20% NaOH (2 L) was added to the filtrate (including the acidic wash). The resulting mixture was extracted with EtOAc (9 L total). The EtOAc extract was filtered through diatomaceous earth. The filtrate was washed with brine, dried ($MgSO_4$) and concentrated under reduced pressure. Purification by flash chromatography ($SiO_2$, EtOAc: Hex, 1:2 to 2:3) of the residue gave tert-butyl N-{4-(4-aminophenyl)-2-thiazolyl}carbamate (48.3 g, 43% yield) as a pale yellow foam: $^1$H NMR (400 MHz, DMSO-$d_6$) $\delta$ 11.40 (s, 1H), 7.52 (d, J=7.2 Hz, 2H), 7.12 (s, 1H), 6.57 (d, J=7.2 Hz, 2H), 5.20 (s, 2H), 1.48 (s, 9H); MS (FAB) m/z 292 (MH)$^+$.

(c) The title compound: 1,1'-Carbonyldiimidazole (1.82 g, 11.3 mmol) was added to a solution of the product of the preceding section (b) (3.00 g, 10.3 mmol) in THF (50 mL) at room temperature. The reaction mixture was stirred at room temperature for 1.5 h, 2-{2-(methylamino) ethyl}pyridine (2.85 mL, 20.6 mmol) was added and the mixture was stirred for another 2 h. EtOAc (500 mL) was added and the resulting solution was washed serially with $H_2O$ (100 mL), saturated aqueous $NaHCO_3$ (2×100 mL) and brine (100 mL), then dried ($MgSO_4$), and concentrated under reduced pressure. The residue was purified by flash chromatography ($SiO_2$, EtOAc:MeOH, 12:1) to give the Boc derivative of the title compound which was treated with trifluoroacetic acid (20 mL) in $CH_2Cl_2$ (40 mL) at room temperature for 3 h. The solution was concentrated under reduced pressure. The residue was taken up in EtOAc (300 mL) and the solution washed with 1N aqueous NaOH. The aqueous layer was extracted with $CH_2Cl_2$ (2×100 mL). The combined organic layers were washed with $H_2O$, dried ($MgSO_4$) and concentrated under reduced pressure. Purification by flash chromatography ($SiO_2$, $CH_2Cl_2$:MeOH, 15:1) and recrystallisation (EtOAc:Hex) gave the title compound (0.45 g, 12% yield) as white crystals: $^1$H NMR (400 MHz, DMSO-$d_6$) $\delta$ 8.52 (d, J=4.5 Hz, 1H), 8.39 (s, 1H), 7.71 (~ddd, J=7.8, 7.5, 1.8 Hz, 1H), 7.65 (d, J=8.7 Hz, 2H), 7.44 (d, J=8.7 Hz, 2H), 7.31 (d, J=7.8 Hz, 1H), 7.22 (broad dd, J=7.5, 4.5 Hz, 1H), 6.96 (s, 2H), 6.82 (s, 1H), 3.70 (t, J=7.2 Hz, 2H), 3.00 (t, J=7.2 Hz, 2H), 2.90 (s, 3H); MS (FAB) m/z 354 (MH)$^+$; Anal. Calcd for $C_{18}H_{19}N_5OS$: C, 61.17; H, 5.42; N, 19.81. Found: C, 60.84; H, 5.45; N, 19.51.

Example 2

N'-{4-(2-Amino-4-thiazolyl)phenyl}-N-{(4-fluorophenyl)methyl}urea {1a: $R^{1A}$=$NH_2$, $R^{2A}$=H, A is absent, $R^{3A}$=H and $R^{4A}$=(4-fluorophenyl)methyl}

4-Fluorobenzylamine (1.80 mL, 15.8 mmol) was added (2 min) to a solution of 4-acetylphenyl isocyanate (2.50 g, 15.5 mmol) in THF (80 mL). The reaction mixture was stirred at room temperature for 2 h, then diluted with EtOAc. The resulting solution was washed serially with 1N aqueous HCl, H$_2$O, saturated aqueous NaHCO$_3$ and brine, dried (MgSO$_4$), and concentrated under reduced pressure. A solution of the residue, thiourea (4.72 g, 62.0 mmol) and I$_2$ (7.87 g, 31.0 mmol) in isopropanol (100 mL) was heated at reflux for 3 h. EtOAc (200 mL) was added to the cooled reaction mixture and the suspension stirred vigorously for 1 h. The suspension was filtered, and the resulting solid was washed with EtOAc and then stirred vigorously in a mixture of 1N aqueous NaOH (~100 mL) and EtOAc (800 mL). The organic layer was washed serially with H$_2$O and brine, then dried (MgSO$_4$) and concentrated under reduced pressure to give the title compound (2.23 g, 42% yield) as a white solid: M.p. 227–230°; $^1$H NMR (400 MHz, DMSO-d$_6$) δ 8.59 (s, 1H), 7.65 (d, J=8.4 Hz, 2H), 7.39 (d, J=8.4 Hz, 2H), 7.34 (dd, J=8.6, 6.1 Hz, 2H), 7.15 (t, J=~8.6 Hz, 2H), 6.96 (s, 2H), 6.80 (s, 1H), 6.62 (t, J=6.0 Hz, 4.28 (d, J=6.0 Hz, 2H); MS (FAB) m/z 343 (MH)$^+$; Anal. Calcd for C$_{17}$H$_{15}$N$_4$OSF: C, 59.64; H, 4.42; N, 16.36. Found: C, 59.67; H, 4.53; N, 16.35.

Example 3

N'-{4-(2-Amino-4-thiazolyl)phenyl}-N,N-dibutylurea (1a: R$^{1A}$=NH$_2$, R$^{2A}$=H, A is absent, and R$^{3A}$ and R$^{4A}$ each is CH$_2$CH$_2$CH$_2$CH$_3$)

(a) 2-Methylpropyl N-(4-Acetylphenyl)carbamate: To a 0° solution of 4'-aminoacetophenone (35 g, 259 mmol) in THF (400 mL) was added pyridine (26 mL, 324 mmol) and isobutyl chloroformate (37 mL, 285 mmol). The resulting heterogeneous mixture was stirred at 0° for 30 min and at room temperature for an additional 30 min. The reaction mixture was then diluted with EtOAc, washed serially with 10% (w/v) aqueous citric acid, 4 N aqueous HCl, H$_2$O, saturated aqueous NaHCO$_3$ and brine, then dried (MgSO$_4$) and concentrated under reduced pressure to yield 2-methylpropyl N-(4-acetylphenyl)carbamate (65 g, quantitative yield) as an off white solid: $^1$H NMR (400 MHz, CDCl$_3$) δ 7.95 (d, 2H, J=8.8 Hz), 7.50 (d, 2H, J=8.8 Hz), 6.85 (s, 1H), 3.99 (d, 2H, J=6.7 Hz), 2.57 (s, 3H), 2.03 (m, 1H), 0.90 (d, 6H, J=6.7 Hz); MS (FAB) m/z 236 (MH)$^+$. This product was used as such in the next reaction (section (b)).

(b) 2-Methylpropyl N-{4-(2-Amino-4-thiazolyl) phenyl}carbamate: To a solution of the product of the preceding section (a) (19 g, 80.75 mmol) in isopropanol (120 mL) was added thiourea (24.6 g, 323 mmol) and iodine (20.5 g, 161.5 mmol). The resulting mixture was heated at reflux for 7 h, then diluted with EtOAc, washed serially with H$_2$O and saturated aqueous NaHCO$_3$. The resulting solution was then treated with 4N aqueous HCl and Et$_2$O and stirred vigorously. The precipitate was filtered and washed with Et$_2$O. The collected solid was then treated with saturated aqueous NaHCO$_3$ and extracted serially with EtOAc and CH$_2$Cl$_2$. The combined organic extracts were washed with H$_2$O and brine, then dried (MgSO$_4$) and concentrated under reduced pressure to yield 2-methylpropyl N-{4-(2-amino-4-thiazolyl)phenyl}carbamate (12 g, 51% yield) as a pale yellow solid: $^1$H NMR (400 MHz, DMSO-d$_6$) δ 9.63 (s, 1H), 7.70 (d, 2H, J=8.9 Hz), 7.46 (d, 2H, J=8.7 Hz), 6.99 (s, 2H), 6.84 (s, 1H), 3.88 (d, 2H, J=6.9 Hz), 1.95 (m, 1H), 0.99 (d, 6H, J=6.9 Hz); MS (FAB) m/z 292 (MH)$^+$. This product was used as such in the next reaction (section (c)).

(c) The title compound: A mixture of the product of the preceding section (b) (35 g, 120.12 mmol) and dibutylamine (101 mL, 600 mmol) was heated at reflux for 4 h. The reaction mixture was then diluted with EtOAc and washed serially with 10% (w/v) aqueous citric acid and H$_2$O. The organic layer was diluted with aqueous HCl (4N) and Et$_2$O. This heterogeneous mixture was stirred and filtered. The collected solid was rinsed with Et$_2$O, treated with 10% aqueous NaOH and serially extracted with EtOAc and dichloromethane. The combined organic extracts were washed with brine, dried (MgSO$_4$) and concentrated under reduced pressure to give 28.5 g of a light yellow solid which was purified by flash chromatography (dry packed, SiO$_2$, 1:8:8:15 mixture of MeOH, EtOAc, hexane, dichloromethane) followed by successive triturations with Et$_2$O until 99% purity (as determined by HPLC) was reached to yield the title compound (17.9 g, 43% yield) as an amber solid: M.p. 160–162°; $^1$H NMR (400 MHz, DMSO-d$_6$) δ 8.14 (s, 1H), 7.65 (d, 2H, J=8.6 Hz), 7.46 (d, 2H, J=8.6 Hz), 6.96 (s, 2H), 6.81 (s, 1H), 3.27–3.31 (m, 4H), 1.47–1.50 (m, 4H), 1.26–1.33 (m, 4H), 0.90 (t, 6H, J=7.2 Hz); MS (FAB) m/z 347 (MH)$^+$; Anal. Calcd for C$_{18}$H$_{26}$N$_4$OS: C, 62.40; H, 7.65; N, 16.17. Found: C, 62.26; H, 7.67; N, 16.15.

Example 4

N-{4-(2-Amino-4-thiazolyl)phenyl}-N',N'-dibutylethanediamide (1a: R$^{1A}$=NH$_2$, R$^{2A}$=H, A=C (0), and R$^{3A}$ and R$^{4A}$ each is CH$_2$CH$_2$CH$_2$CH$_3$)

To a 0° solution of oxalyl chloride (479 mL, 5.49 mmol) in THF (10 mL) under nitrogen was added DIPEA (2.28 mL, 13.07 mmol) and dibutylamine (925 mL, 5.49 mmol). The resulting mixture was stirred at 0° for 5 min, whereby (dibutylamino)oxoacetyl chloride is formed, then transferred via syringe to a solution of 4-(4-aminophenyl)-2-aminothiazole (corresponding to the deprotected title compound of either Example 1 (a) or 1 (b)). The resulting mixture was stirred under nitrogen for 4 h, after which time another batch of freshly prepared (N,N-dibutylamino) oxalylchloride (prepared in the same manner and with the same amounts as above) was added to the reaction mixture. The stirring was continued for 1 h. The mixture was then diluted with EtOAc and extracted with 10% aqueous HCl. This aqueous extract was washed with EtOAc:Hex (1:1), then filtered. The collected solid, containing the desired product as its hydrochloride salt, was treated with 2N aqueous NaOH and extracted with EtOAc. This latter extract was washed with H$_2$O, dried (MgSO$_4$) and concentrated under reduced pressure to give a solid (398 mg) which was further purified by crystallization from EtOAc/MeOH to give the title compound (240 mg, 12% yield) as a beige solid: M.p. 178–179° C.; $^1$H NMR (400 MHz, DMSO-d$_6$) δ 10.68 (s, 1H), 7.75 (d, 2H, J=8.7 Hz), 7.64 (d, 2H, J=9.0 Hz), 7.02 (s, 2H), 6.92 (s, 1H), 3.33 (m, 4H), 1.50–1.60 (m, 4H), 1.33 (sixt., 4H, J=7.5 Hz), 1.25 (sixt., 4H, J=7.5 Hz), 0.92 (t, 3H, J=7.5 Hz), 0.82 (t, 3H, J=7.5 Hz); MS (FAB) m/z 375 (MH)$^+$. Anal. Calcd for C$_{19}$H$_{26}$N$_4$O$_2$S: C, 60.94; H, 7.00; N, 14.96. Found: C, 60.82; H, 6.85; N, 14.95.

Example 5

In conjunction with the appropriate starting materials and intermediates, the procedures of Group 2-Examples 1 to 4 can be used to prepare other compounds of Group 2-formula 1a. Examples of compounds thus prepared are listed in Tables 1 and 2 of Group 2-Example 5, together with mass spectrum data for the individual compounds and the results obtained from assays demonstrating antiherpes activity. The assays have been described hereinbefore.

TABLE 1
Compound of formula 1a having the structure:
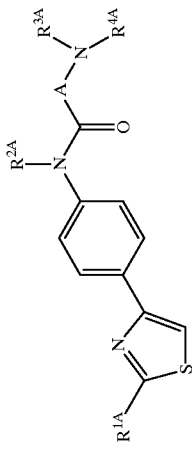
wherein A is absent, $R^{2A}$ is H, and $R^{1A}$, $R^{3A}$ and $R^{4A}$ are designated as follows:
| ENTRY No | $R^{1A}$ | $R^{3A}$ | $R^{4A}$ | FAB/MS (m/z) (MH)$^+$ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|---|
| 1 | NH$_2$ | Bu | Bu | 347 | 4.2 | 0.8 | 4.1 | 37 |
| 2 | NH$_2$ | H | Bu | 291 | 6.4 | 3.5 | 0.6 | 12 |
| 3 | NH$_2$ | H | 2-pyridyl-CH$_2$ | 340 | 5.2 | 3.6 | | >93* |
| 4 | NH$_2$ | CH$_3$ | 2-pyridyl-CH$_2$ | 354 | 3.7 | 1.4 | 126 | >144 |
| 5 | NH$_2$ | H | 4-pyridyl-CH$_2$ | 326 | 12 | 25 | 0.4 | 70 |
| 6 | NH$_2$ | H | 3-pyridyl-CH$_2$ | 325 | 6.5 | 3.6 | 2.5 | 55 |
| 7 | NH$_2$ | H | (4-Fph)CH$_2$ | 343 | 1.9 | 1.3 | 3.2 | 8* |

TABLE 1-continued
Compound of formula 1a having the structure:
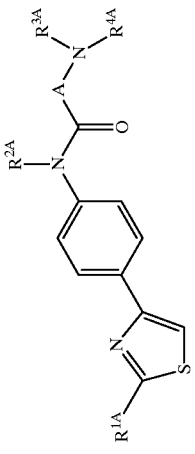
wherein A is absent, $R^{2A}$ is H, and $R^{1A}$, $R^{3A}$ and $R^{4A}$ are designated as follows:
| ENTRY No | $R^{1A}$ | $R^{3A}$ | $R^{4A}$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|---|
| 8 | $NH_2$ | H | (structure) | 439 | 0.07 | 4 | >4 | >103 |
| 9 | $NH_2$ | H | (structure) | 501 | 7.1 | 2.9 | 4.1 | 36 |
| 10 | $NH_2$ | H | (structure) | 343 | 4.7 | | | >48* |
| 11 | $NH_2$ | H | (structure) | 333 | 17 | 8 | 1.3 | 13 |

TABLE 1-continued

Compound of formula 1a having the structure:

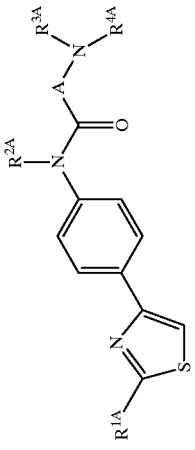

wherein A is absent, R$^{2A}$ is H, and R$^{1A}$, R$^{3A}$ and R$^{4A}$ are designated as follows:

| ENTRY No | R$^{1A}$ | R$^{3A}$ | R$^{4A}$ | FAB/MS (m/z) (MH)$^+$ | HSV-1 IC$_{50}$ (µM) | HSV-1 EC$_{50}$ (µM) | ELISA CMV EC$_{50}$ (µM) | PRA CMV EC$_{50}$ (µM) |
|---|---|---|---|---|---|---|---|---|
| 12 | NH$_2$ | H | HC(CH$_3$)(CH$_3$) | 291 | 20 | 4.4 | 6 | >32 |
| 13 | NH$_2$ | H | CH$_2$Ph | 339 | 37 | | | >4 |
| 14 | Me$_3$COC(O)NH | Me | CH$_2$-(2-pyridyl) | 454 | >100 | 3.2 | 1.5 | 2.0 |
| 15 | Me$_3$COC(O)NH | Bu | Bu | 447 | >100 | >6 | 1 | 1.1 |
| 16 | NH$_2$ | H | (PhCH$_2$)$_2$NCH$_2$CH$_2$ | 458 | 1.6 | | | >5* |
| 17 | NH$_2$ | H | HC≡CCH$_2$ | 273 | 33 | | | >74 |
| 18 | NH$_2$ | H | 2-methylthiazolyl | 318 | | | | >56 |
| 19 | NH$_2$ | H | 3-(CH$_2$CH$_2$)-indolyl | 378 | | | | 12 |

TABLE 1-continued

Compound of formula 1a having the structure:

![Structure: R1A-thiazole-phenyl-N(R2A)-C(O)-A-N(R3A)(R4A)]

wherein A is absent, R2A is H, and R1A, R3A and R4A are designated as follows:

| ENTRY No | R1A | R3A | R4A | FAB/MS (m/z) (MH)+ | HSV-1 IC50 (μM) | HSV-1 EC50 (μM) | ELISA CMV EC50 (μM) | PRA CMV EC50 (μM) |
|---|---|---|---|---|---|---|---|---|
| 20 | NH2 | H | PhCH2 | 325 | 0.90 | | | >45* |
| 21 | NH2 | H | (4-ClPh)CH2 | 359/361** | 7.2 | | | >1* |
| 22 | NH2 | H | (3-FPh)CH2 | 343 | 1.3 | | | >8* |
| 23 | NH2 | H | (2-FPh)CH2 | 343 | 2.0 | | | >4* |
| 24 | NH2 | H | (4-FPh)CH2CH2 | 357 | 30 | | | >5* |
| 25 | NH2 | H | (4-Me2NPh)CH2 | 368 | 2.9 | | | >18* |
| 26 | NH2 | H | Ph-(S)—CHMe | 339 | 0.59 | | | >74* |
| 27 | NH2 | H | N-methylpiperidinyl | 318 | 50 | 15.7 | 15.4 | 30 |
| 28 | NH2 | H | (S)—(PhCH2)CHCH2OH | 369 | 6.6 | | | 3.9 |
| 29 | Me3COC(O)NH | Me | 4-pyridyl-CH2CH2 | 454 | | | | |
| 30 | Me3COC(O)NH | Me | Bu | 405 | | | | 2.2 |
| 31 | Me3COC(O)NH | Et | Bu | 419 | | | | 2.0 |
| 32 | Me3COC(O)NH | HOCH2CH2 | Bu | 435 | | | | 2.0 |
| 33 | Me3COC(O)NH | NC—CH2 | Bu | 430 | | | | 2.4 |
| 34 | BuNH | Bu | Bu | 403 | | | | 10 |
| 35 | 2-pyridyl-NH | Bu | Bu | 424 | | | | 2.2 |

TABLE 1-continued

Compound of formula 1a having the structure:

R1A—[thiazole]—[phenyl]—N(R2A)—C(O)—A—N(R3A)(R4A)

wherein A is absent, R2A is H, and R1A, R3A and R4A are designated as follows:

| ENTRY No | R1A | R3A | R4A | FAB/MS (m/z) (MH)+ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|---|
| 36 | 3-pyridyl-NH— | Bu | Bu | 424 | | | | 3.0 |

*Cytotoxic at this concentration
***Includes isotopic peak due to chlorine

TABLE 2

Compound of formula 1a having the structure:

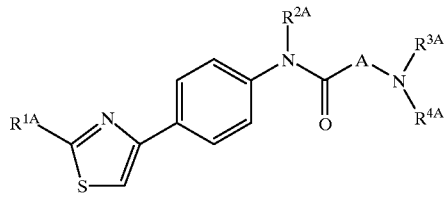

| ENTRY | wherein A is C(O), $R^{2A}$ is H, $R^{1A}$ is $NH_2$, and $R^{3A}$ and $R^{4A}$ are designated as follows: | | FAB/MS (m/z) | HSV-1 $IC_{50}$ | HSV-1 $EC_{50}$ | ELISA CMV $EC_{50}$ | PRA CMV $EC_{50}$ |
|---|---|---|---|---|---|---|---|
| No | $R^{3A}$ | $R^{4A}$ | $(MH)^+$ | ($\mu M$) | ($\mu M$) | ($\mu M$) | ($\mu M$) |
| 1 | Bu | Bu | 375 | 7 | 2.9 | 2.6 | >4 |
| 2 | $CH_2Ph$ | $CH_2Ph$ | 443 | 1.2 | 0.77 | 10 | 12* |

*Cytotoxic at this concentration

Group 3: Thiazolylbenzamido Derivatives

According to another embodiment of this invention, the present application refers to Group 3 thiazolylbenzamido derivatives having antiherpes activity. The selective action of these compounds against herpes viruses, combined with a wide margin of safety, renders the compounds as desirable agents for combating herpes infections.

The thiazolylbenzamido derivatives of the present invention can be characterized structurally by the presence of a 4-(4-thiazolyl)benzamido moiety. Compounds possessing such a moiety have been reported previously, for example:

C. G. Caldwell et al., U.S. Pat. No. 4,746,669, issued May 24, 1988;

A. Bernat et al., Canadian patent application 2,046,883, published Jun. 30, 1991;

A. Wissner, European patent application 458,037, published Nov. 27, 1991;

D. I. C. Scopes et al., UK patent application 2 276 164, published Sep. 21, 1994;

A. Leonardi et al., PCT patent application WO 95/04049, published Feb. 9, 1995; and G. D. Hartman et al., PCT patent application WO 95/32710, published Dec. 7, 1995.

The present thiazolylbenzamido derivatives can be distinguished readily from the prior art compounds in that they possess different chemical structures and biological activities.

The Group 3 compounds of this application can also be represented by formula 1b:

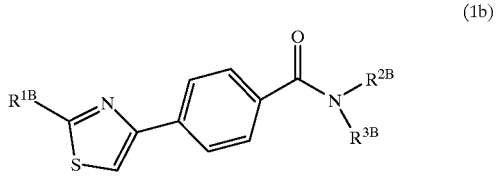

wherein $R^{1B}$ has the same meaning as R as defined hereinbefore and $R^{2B}$ and $R^{3B}$ are as defined hereinbefore.

A preferred set of Group 3 compounds of this invention is represented by Group 3-formula 1b wherein $R^{1B}$ is hydrogen, lower alkyl, amino, lower alkylamino, di(lower alkyl)amino, lower alkanoylamino or (lower alkoxycarbonyl)amino; $R^{2B}$ is hydrogen, (1-8C)alkyl, lower alkenyl, lower alkynyl, phenyl-(1-3C)alkyl, phenyl-(1-3C) alkyl monosubstituted or disubstituted on the aromatic portion thereof with a halo, hydroxy, lower alkoxy, lower alkyl or trifluoromethoxy; (lower cycloalkyl)-(1-3C)alkyl or (Het)-(1-3C)alkyl wherein Het is as defined hereinbefore; 2-benzimidazolylmethyl; and $R^{3B}$ is (1-8C)alkyl, phenyl-(1-3C)alkyl, phenyl-(1-3C)alkyl monosubstituted or disubstituted on the aromatic portion thereof with a halo, hydroxy, lower alkoxy, lower alkyl or trifluoromethoxy; 1-indanyl, 2-indanyl, (lower cycloalkyl)-(1-3C)alkyl, {1-hydroxy (lower cycloalkyl)}-(1-3C)alkyl or (Het)-(1-3C)alkyl wherein Het is as defined hereinbefore; or $R^{3B}$ is:

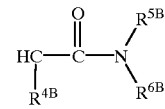

wherein $R^{4B}$ and $R^{5B}$ independently have the same significance as defined for $R^{2B}$ in the last instance and $R^{6B}$ has the same significance as defined for $R^{3B}$ in the last instance;or $R^{3B}$ is $CH_2CH_2NR^{5B}R^{6B}$ wherein $R^{5B}$ and $R^{6B}$ are as defined herein; or $R^{3B}$ is $CH(R^{7B})CH_2OH$ wherein $R^{7B}$ has the same significance as defined for $R^{2B}$ in the last instance; or $R^{2B}$ and $R^{3B}$ together with the nitrogen atom to which they are attached form a pyrrolidino, piperidino, (4-phenylmethyl)piperidinyl or (4-methyl)piperizinyl; with the proviso that when $R^{1B}$ is (lower alkoxycarbonyl)amino then $R^{2B}$ is hydrogen; or a therapeutically acceptable acid addition salt thereof.

A more preferred set of Group 3 compounds are represented by Group 3-formula 1b wherein $R^{1B}$ is hydrogen, amino, methylamino, dimethylamino, acetylamino or (1,1-dimethylethoxycarbonyl)amino; $R^{2B}$ is hydrogen, methyl, ethyl, propyl, butyl, 1,1-dimethylethyl, 2-methylpropyl, 2,2-dimethylpropyl, 1-propenyl, 2-propenyl, 2-propynyl, phenylmethyl, 1(R) -phenylethyl, 1(S) -phenylethyl, 2-phenylethyl, (4-chlorophenyl)methyl, (2-fluorophenyl) methyl, (3-fluorophenyl)methyl, (4-fluorophenyl)methyl, (2-hydroxyphenyl)methyl, (4-methoxyphenyl)methyl, (2-methylphenyl)methyl, (4-methylphenyl)methyl, {(2-trifluoromethoxyphenyl)methyl}, (2-hydroxy-3-methoxyphenyl)methyl, cyclopropylmethyl, cyclopentylmethyl, cyclohexylmethyl, 2-cyclohexylethyl, (1-hydroxycyclohexyl)methyl, 2-(4-morpholinyl)ethyl, 2-pyridinylmethyl, 3-pyridinylmethyl, 4-pyridinylmethyl, 2-(2-pyridinyl)ethyl, 2-(3-pyridinyl)ethyl, 2-(4-pyridinyl) ethyl,2-furanylmethyl, 2-thienylmethyl, 3-thienylmethyl, 2-thiazolylmethyl, 1-(phenylmethyl)piperidin-4-yl or 2-benzimidazolylmethyl; and $R^{3B}$ is methyl, ethyl, propyl, butyl, 1,1-dimethylethyl, 2-methylpropyl, 2,2-dimethylpropyl, phenylmethyl, 2-phenylethyl, (4-chlorophenyl)methyl, (2-fluorophenyl)methyl, (3-fluorophenyl)methyl, (4-fluorophenyl)methyl, (2-hydroxyphenyl)methyl, (4-methoxyphenyl)methyl, (2-methylphenyl)methyl, (4-methylphenyl)methyl, {(2-trifluoromethoxy)phenyl}methyl, (2-hydroxy-3-methoxyphenyl)methyl, 1-indanyl, 2-indanyl, cyclopentylmethyl, cyclohexylmethyl, 2-cyclohexylethyl, (1-hydroxycyclohexyl)methyl, 2-(4-morpholinyl)ethyl, 2-pyridinylmethyl, 3-pyridinylmethyl, 4-pyridinylmethyl, 2-(2-pyridinyl)ethyl, 2-(3-pyridinyl)ethyl, 2-(4-pyridinyl) ethyl, 2-thienylmethyl, 3-thienylmethyl, 2-thiazolylmethyl, 1(R)-phenylethyl, 1(S)-phenylethyl, 1(R)-cyclohexylethyl or 1(S)-cyclohexylethyl;

or $R^{3B}$ is

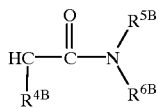

wherein $R^{4B}$ is hydrogen, methyl, 1-methylethyl, phenylmethyl, cyclohexylmethyl, 3-pyridinylmethyl or (1H-imidazol-4-yl)methyl; $R^{5B}$ has the same significance as defined for $R^{2B}$ in the last instance and $R^{6B}$ has the same significance as defined for $R^{3B}$ in the last instance; or $R^{3B}$ is $CH_2CH_2NR^{5B}R^{6B}$ wherein $R^{5B}$ and $R^{6B}$ are defined herein; or $R^{3B}$ is $CH(R^{7B})CH_2OH$ wherein $R^{7B}$ has the same significance as defined for $R^{4B}$ in the last instance; or a therapeutically acceptable acid addition salt thereof.

Another more preferred set of Group 3 compounds is represented by Group 3-formula 1b wherein $R^{1B}$ is hydrogen, amino, methylamino, dimethylamino, acetylamino or (1,1-dimethylethoxycarbonyl)amino; $R^{2B}$ is hydrogen, methyl, ethyl, propyl, butyl, 1,1-dimethylethyl, 2-methylpropyl or 2,2-dimethylpropyl; $R^{3B}$ is methyl, ethyl, propyl, butyl, 1,1-dimethylethyl, 2-methylpropyl, 2,2-dimethylpropyl, phenylmethyl, 2-phenylethyl, (4-chlorophenyl)methyl, (2-fluorophenyl)methyl, (3-fluorophenyl)methyl, (4-fluorophenyl)methyl, (2-hydroxyphenyl)methyl, (4-methoxyphenyl)methyl, (2-methylphenyl)methyl, (4-methylphenyl)methyl, {(2-trifluoromethoxy)phenyl}methyl, (2-hydroxy-3-methoxyphenyl)methyl, 1-indanyl, 2-indanyl, cyclopentylmethyl, cyclohexylmethyl, 2-cyclohexylethyl, (1-hydroxycyclohexyl)methyl, 2-(4-morpholinyl)ethyl, 2-pyridinylmethyl, 3-pyridinylmethyl, 4-pyridinylmethyl, 2-(2-pyridinyl)ethyl, 2-(3-pyridinyl)ethyl, 2-(4-pyridinyl) ethyl, 2-thienylmethyl, 3-thienylmethyl, 2-thiazolylmethyl, 1(R)-phenylethyl, 1(S)-phenylethyl, 1(R)-cyclohexylethyl or 1(S)-cyclohexylethyl; or $R^{3B}$ is:

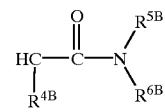

wherein $R^{4B}$ is hydrogen, methyl, 1-methylethyl, phenylmethyl, cyclohexylmethyl, 3-pyridinylmethyl, or (1H-imidazol-4-yl)methyl; $R^{5B}$ is hydrogen or has the same significance as defined for $R^{3B}$ in the last instance and $R^{6B}$ has the same significance as defined for $R^{3B}$ in the last instance; or $R^{3B}$ is $CH(R^{7B})CH_2OH$ wherein $R^{7B}$ has the same significance as defined for $R^{4B}$ in the last instance; or a therapeutically acceptable acid addition salt thereof.

Still another more preferred set of Group 3 compounds is represented by Group 3-formula 1b wherein $R^{1B}$ is hydrogen, amino, methylamino, dimethylamino, acetylamino or (1,1-dimethylethoxycarbonyl)amino; $R^{2B}$ is hydrogen, methyl, ethyl, propyl, butyl, 1,1-dimethylethyl, 2-methylpropyl, 2,2-dimethylpropyl, phenylmethyl, 2-phenylethyl, (4-chlorophenyl)methyl, (2-fluorophenyl) methyl, (3-fluorophenyl)methyl, (4-fluorophenyl)methyl, (2-hydroxyphenyl)methyl, (4-methoxyphenyl)methyl, (2-methylphenyl)methyl, (4-methylphenyl)methyl, {(2-trifluoromethoxy)phenyl}methyl, (2-hydroxy-3-methoxyphenyl)methyl, cyclopentylmethyl, cyclohexylmethyl, 2-cyclohexylethyl, (1-hydroxycyclohexyl)methyl, 2-(4-morpholinyl)ethyl, 2-pyridinylmethyl, 3-pyridinylmethyl, 4-pyridinylmethyl, 2-(2-pyridinyl)ethyl, 2-(3-pyridinyl)ethyl, 2-(4-pyridinyl) ethyl, 2-thienylmethyl, 3-thienylmethyl, 2-thiazolylmethyl, 1(R)-phenylethyl or 1(S)-phenylethyl; and $R^{3B}$ is:

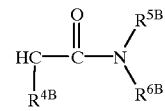

wherein $R^{4B}$ is hydrogen, methyl, 1-methylethyl, phenylmethyl, cyclohexylmethyl, 3-pyridinylmethyl or (1H-imidazol-4-yl)methyl; $R^{5B}$ has the same significance as defined for $R^{2B}$ in the last instance and $R^{6B}$ has the same significance as defined for $R^{2B}$ in the last instance excluding hydrogen; or $R^{3B}$ is $Ch_2$ $CH_2NR^{5B}R^{6B}$ wherein $R^{5B}$ and $R^{6B}$ are as defined herein; or $R^{3B}$ is $CH(R^{7B})CH_2OH$ wherein $R^{7B}$ has the same significance as defined for $R^{4B}$ in the last instance; or a therapeutically acceptable acid addition salt thereof.

A most preferred set of Group 3 compounds is represented by Group 3-formula 1b wherein $R^{1B}$ is amino; $R^{2B}$ is hydrogen or phenylmethyl; $R^{3B}$ is:

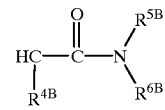

wherein $R^{4B}$ is hydrogen, $R^{5B}$ is hydrogen or phenylmethyl and $R^{6B}$ is phenylmethyl, 1(R)-phenylethyl or 1(S)-phenylethyl; or $R^{3B}$ is $CH(R^{7B})CH_2OH$ wherein $R^{7B}$ is phenylmethyl and the carbon atom bearing the $R^{7B}$ group has the (S) configuration; or a therapeutically acceptable acid addition salt thereof.

Still another most preferred set of Group 3 compounds is represented by Group 3-formula 1b wherein $R^{1B}$ is amino or (1,1-dimethylethoxycarbonyl)amino; $R^{2B}$ is hydrogen, 2-propynyl, phenylmethyl, 2-phenylethyl, cyclopropylmethyl, 2-pyridinylmethyl, 3-pyridinylmethyl, 4-pyridinylmethyl, 2-(2-pyridinyl)ethyl, 2-furanylmethyl, 1-(phenylmethyl)piperidin-4-yl or 2-benzimidazolylmethyl; and $R^{3B}$ is phenylmethyl or (3-fluorophenyl)methyl; and $R^{3B}$ is:

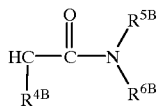

wherein $R^{4B}$ is hydrogen, $R^{5B}$ is hydrogen, methyl, phenylmethyl, (2-hydroxyphenyl)methyl, (2-methylphenyl)methyl, {(2-trifluoromethoxy)phenyl}methyl, (2-hydroxy-3-methoxyphenyl)methyl, (1-hydroxycyclohexyl)methyl, 2-pyridinylmethyl, 3-pyridinylmethyl, 4-pyridinylmethyl or 2-thiazolylmethyl; and $R^{6B}$ is phenylmethyl or 1(S or R)phenylethyl; or $R^{3B}$ is $CH_2CH_2NR^{5B}R^{6B}$ wherein $R^{5B}$ is phenylmethyl and $R^{6B}$ is phenylmethyl or 1(S or R)phenylethyl; or $R^{3B}$ is $CH(R^{7B})CH_2OH$ wherein $R^{7B}$ is phenylmethyl and the carbon atom bearing the $R^{7B}$ group has the (S) configuration; or a therapeutically acceptable acid addition salt thereof.

Included within the scope of this invention is a pharmaceutical composition comprising an antiherpes virally effective amount of a compound of Group 3 as defined herein, or a therapeutically acceptable acid addition salt thereof, and a pharmaceutically or veterinarily acceptable carrier.

Still another aspect of this invention involves a method for treating acyclovir-resistant herpes infections in a mammal which comprises administering to the mammal an anti-acyclovir-resistant herpes effective amount of a compound of Group 3 as defined herein, or a therapeutically acceptable acid addition salt thereof.

Process for Preparing the Compounds of Group 3

The compounds of Group 3 can be prepared by a variety of processes. Descriptions of some of these methods are found in standard textbooks such as "Annual Reports In Organic Synthesis-1994", P. M. Weintraub et al., Eds., Academic Press, Inc., San Diego, Calif., USA, 1994 (and the preceding annual reports), "Vogel's Textbook of Practical Organic Chemistry", B. S. Furniss et al., Eds., Longman Group Limited, Essex, UK, 1986, and "Comprehensive Organic Synthesis", B. M. Trost and I. Fleming, Eds., Pergamon Press, Oxford, UK, 1991, Volumes 1 to 8.

Generally speaking, the compounds of Group 3-formula 1b can be prepared by a process selected from the following processes (a) or (b):

(a) coupling a compound of the formula

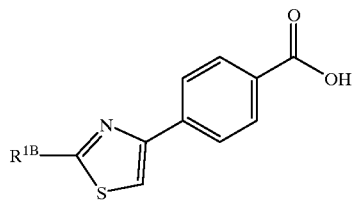

wherein $R^{1B}$ is as defined herein, with an amine of the formula:

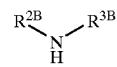

wherein $R^{2B}$ and $R^{3B}$ are as defined herein, to obtain the corresponding compound of formula 1b; or (b) coupling 4-acetylbenzoic acid with an amine of the formula:

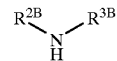

wherein $R^{2B}$ and $R^{3B}$ are as defined herein, to obtain the corresponding benzamide derivative of the formula:

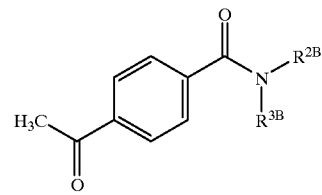

and either (i) reacting the latter benzamide derivative with $Br_2$, $Cl_2$ or $I_2$ whereby the methyl ketone moiety of the benzamide derivative is converted to the corresponding α-haloketone and reacting the resulting α-haloketone with a thioamide or thiourea of the formula $H_2N-C(S)-R^{1AAA}$ wherein $R^{1AAA}$ is hydrogen, lower alkyl, amino, lower alkylamino or di(lower alkyl)amino to obtain the corresponding compound of Group 3-formula 1b wherein $R^{1B}$ is hydrogen, lower alkyl, amino, lower alkylamino or di(lower alkyl)amino, and $R^{2B}$ and $R^{3B}$ are as defined herein; or (ii) reacting the latter benzamide derivative with a thiourea derivative of the formula $H_2N-C(S)-R^{1AAA}$, wherein $R^{1AAA}$ is amino, lower alkylamino or di(lower alkyl)amino, in the presence of $Br_2$, $Cl_2$ or $I_2$ to obtain the corresponding compound of Group 3-formula 1b wherein $R^{1B}$ is amino, lower alkylamino or di(lower alkyl)amino and $R^{2B}$ and $R^{3B}$ are as defined herein; and if desired, effecting standard transformations to the products of processes (a) and (b) to obtain other compounds of Group 3-formula 1b; and further, if desired, converting the compound of Group 3-formula 1b into a therapeutically acceptable acid addition salt.

More explicitly, a practical and convenient procedure to prepare compounds of Group 3-formula 1b is illustrated by Group 3-scheme 1:

Group 3 - Scheme 1

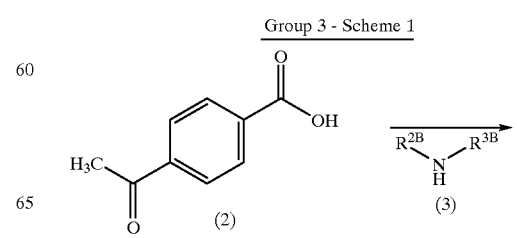

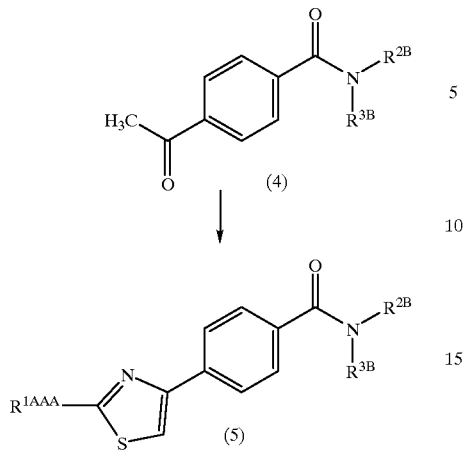

According to Group 3-scheme 1, 4-acetylbenzoic acid (2) is coupled with an amine derivative of formula 3, wherein $R^{2B}$ and $R^{3B}$ are as defined herein, to give a corresponding benzamide derivative of formula 4.

The coupling of 4-acetylbenzoic acid (2) and the amine derivative of formula 3 is effected by the classical dehydrative coupling of a free carboxyl of one reactant with the free amino group of the other reactant in the presence of a coupling agent to form a linking amide bond, as described hereinbefore.

The benzamide derivative of formula 4 is converted to the thiazolyl derivative of formula 5 wherein $R^{1AAA}$ hydrogen, lower alkyl, amino, lower alkylamino or di(lower alkyl) amino by reacting the compound of formula 4 with $Br_2$, $Cl_2$ or $I_2$ whereby the methyl ketone moiety of the compound of formula 4 is converted to the corresponding α-haloketone. This α-haloketone derivative is then reacted with a thioamide or thiourea of the formula $H_2N-C(S)-R^{1AAA}$ wherein $R^{1AAA}$ is hydrogen, lower alkyl, amino, lower alkylamino or di(lower alkyl)amino according to the classical reaction described by R. H. Wiley et al, Organic Reactions 1951, 6, 367–374 for preparing thiazole compounds from thioamides or thioureas and α-halocarbonyl compounds, to obtain the corresponding thiazolyl derivative of formula 5. Alternatively, the benzamide derivative of formula 4 can be directly converted to the thiazolyl derivative of formula 5 wherein $R^{1AAA}$ is amino, lower alkylamino or di(lower alkyl)amino by heating the benzamide derivative of formula 4 with an appropriate thiourea derivative of the formula $H_2N-C(S)-R^{1AAA}$, wherein $R^{1AAA}$ is amino, lower alkylamino or di(lower alkyl)amino, in the presence of $Br_2$, $Cl_2$ or $I_2$ according to the classical methods of R. M. Dodson and L. C. King, J. Amer. Chem Soc. 1945, 67, 2242. The thiazolylbenzamide derivative of formula 5, albeit a compound of Group 3-formula 1b, can also serve as an intermediate for further elaboration by standard methods to yield other compounds of Group 3-formula 1b (for example, the compound of formula 5 wherein $R^{1AAA}$ is amino can serve as an intermediate for transformation by standard methods to compounds of Group 3-formula 1b wherein $R^{1B}$ is lower alkanoylamino or lower alkoxycarbonyl).

Another general procedure for preparing compounds of Group 3-formula 1b can be represented by Group 3-scheme 2:

According to Group 3-scheme 2, an N-protected amino acid of formula 6, wherein PG is an amino protecting group and $R^{2B}$ and $R^{4B}$ are as defined herein, is reacted with an amine derivative of formula 7 wherein $R^{5B}$ and $R^{6B}$ are as defined herein, to give the amide derivative of formula 8. The amino protecting group PG of the amide of formula 8 is then removed to give the compound of formula 9.

The compound of formula 9 can then be used to prepare compounds of Group 3-formula 1b by simply repeating the process outlined in Group 3-scheme 1 and replacing the amine of formula 3 in Group 3-scheme 1 with the amine of formula 9 from Group 3-scheme 2.

Examples of amino protective groups suitable for use in the above schemes include benzyloxycarbonyl, tert-butoxycarbonyl, 4-methoxybenzyloxycarbonyl or 2,2,2-trichloroethoxycarbonyl.

Other starting materials for the preceding processes are known or can be readily prepared from known starting materials. 4-Acetylbenzoic acid (2) of Group 3-scheme 1 is available from the Aldrich Chemical Co., Milwaukee, Wis., USA.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, the reaction can be successfully performed by conventional modification known to those skilled in the art, e.g. by appropriate protection of interfering groups, by changing to alternative conventional reagents, by routine modification of reaction conditions, or by modification illustrated in the examples herein.

Furthermore, if desired, the compound of Group 3-formula 1b can be obtained in the form of a therapeutically acceptable acid addition salt. Such salts can be considered as biological equivalents of the compounds of Group 3-formula 1b. Examples of such salts are those formed with hydrochloric acid, sulfuric acid, phosphoric acid, formic acid, acetic acid or citric acid.

Antiherpes Activity

The antiviral activity of the compounds of Group 3-formula 1b, or their corresponding therapeutically acceptable acid addition salts, can be demonstrated in the same manner as described herein for the compounds of Group 1-formula 1. Likewise, the compounds of Group 3-formula 1b, or their corresponding therapeutically acceptable acid addition salts, can be formulated and employed as antiviral agents in the same manner as described herein for the compounds of Group 1-formula 1.

The following examples further illustrate this invention. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts (δ) are reported in parts per million. The concentrations for the optical rotations are expressed in grams of the compound per 100 mL of solution. Abbreviations or symbols used in the examples are as defined hereinbefore.

GROUP 3 EXAMPLES

Example 1

4-(2-Amino-4-thiazolyl)-N-{2-oxo-2-{di(phenylmethyl) amino}ethyl}benzamide (1b: $R^{1B}$=NH$_2$, $R^{2B}$=H, $R^{3B}$=

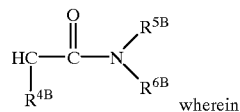

wherein $R^{4B}$ = H, $R^{5B}$ = phenylmethyl and $R^{6B}$ = phenylmethyl)

(a) tert-Butyl N-{2-Oxo-2-{di(phenylmethyl) amino}ethyl}carbamate: To a solution of Boc-glycine (6.0 g, 34.2 mmol) (Aldrich Chemical Co., Milwaukee, Wis., USA) in DMF (100 mL) was added successively DIPEA (17.9 mL, 103 mmol), dibenzylamine (6.25 mL, 32.5 mmol) (Aldrich Chemical Co., Milwaukee, Wis., USA) and BOP.PF$_6$ (15.14 g, 34.2 mmol). The resulting solution was stirred at room temperature for 2 h, then diluted with EtOAc, washed serially with H$_2$O, 4N aqueous HCl, saturated aqueous NaHCO$_3$, and brine, dried (MgSO$_4$) and concentrated under reduced pressure to give tert-butyl N-{2-oxo-2-{di (phenylmethyl)amino}ethyl}carbamate (11.39 g, 99% yield) as an off white solid: $^1$H NMR (400 MHz, DMSO-d$_6$) δ 7.21–7.39 (m, 10H), 6.86 (t, 1H, J=5.7 Hz), 4.50 (s, 2H), 4.48 (s, 2H), 3.87 (d, 2H, J=5.7 Hz), 1.37 (s, 9H); MS (FAB) m/z 355 (MH)$^+$.

(b) N,N-Di(phenylmethyl)-2-aminoacetamide Hydrochloride: To a solution of the product of the preceding section (a) (2.5 g, 7.03 mmol) in 1,4-dioxane (10 mL) was added 4N HCl in 1,4-dioxane (8.8 mL, 35.2 mmol). The resulting solution was stirred at room temperature for 5 h, then concentrated under reduced pressure (coevaporation with 1:1 Et$_2$O/benzene) to give N,N-di(phenylmethyl)-2-aminoacetamide hydrochloride (2.05 g, 99% yield) as a light yellow foam: $^1$H NMR (400 MHz, DMSO-d$_6$) δ 8.24 (s, 2H), 7.22–7.41 (m, 10H), 4.54 (s, 4H), 3.90 (s, 2H); MS (FAB) m/z 255 (MH)$^+$. This product was used as such in the next reaction (section (c)).

(c) N-{2-Oxo-2-{di(phenylmethyl)amino}ethyl}-4-acetylbenzamide: To a solution of 4-acetylbenzoic acid (1.21 g, 7.37 mmol) in DMF (35 mL) was added successively the product of the preceding section (b) (2.03 g, 7.0 mmol), DIPEA (4.3 mL, 24.5 mmol) and BOP.PF$_6$ (3.25 g, 7.37 mmol). The resulting solution was stirred at room temperature for 2 h, then diluted with EtOAc, washed serially with H$_2$O, 4N aqueous HCl, saturated NaHCO$_3$, and brine, dried (MgSO$_4$) and concentrated under reduced pressure to give N-{2-oxo-2-{di(phenylmethyl)amino}ethyl}-4-acetylbenzamide (2.70 g, 99% yield) as a light yellow foam: $^1$H NMR (400 MHz, DMSO-d$_6$) δ 8.89 (t, 1H, J=5.7 Hz), 8.05 (d, 2H, J=8.4 Hz), 8.00 (d, 2H, J=8.4 Hz), 7.24–7.44 (m, 10 H), 4.61 (s, 2H), 4.51 (s, 2H), 4.25 (d, 2H, J=5.7 Hz), 2.52 (s, 3H); MS (FAB) m/z 401 (MH)$^+$. This product was used as such in the next reaction (section (d)).

(d) The title compound: To a solution of the product of the preceding section (c) (2.7 g, 6.74 mmol) in isopropanol (14 mL) was added iodine (3.55 g, 14.0 mmol) and thiourea (2.13 g, 28.0 mmol). The resulting mixture was heated at reflux for 18 h, then diluted with EtOAc/Et$_2$O and filtered. The collected solid was then treated with 1N aqueous NaOH and extracted with EtOAc. The EtOAc extract was washed with brine, and dried (MgSO$_4$). Concentrated under reduced pressure, followed by trituration with EtOAc, gave the title compound (1.58 g, 50% yield) as a white solid: $^1$H NMR (400 MHz, DMSO-d$_6$) δ 8.66 (t, 1H, J=5.7 Hz), 7.88 (s, 4H), 7.22–7.42 (m, 10H), 7.18 (s, 1H), 7.09 (s, 2H), 4.60 (s, 2H), 4.51 (s, 2H), 4.23 (d, 2H, J=5.7 Hz); MS (FAB) m/z 457 (MH)$^+$.

Example 2

4-(2-Amino-4-thiazolyl)-N-{2-Oxo-2-{(phenylmethyl){1 (S)-phenylethyl}amino}ethyl}-N-(phenylmethyl) benzamide (1b: $R^{1B}$=NH$_2$, $R^{2B}$=phenylmethyl, $R^{3B}$=

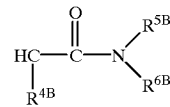

wherein $R^{4B}$ = H, $R^{5B}$ = phenylmethyl and $R^{6B}$ = 1(S)-phenylethyl)

(a) 2-(phenylmethyl)amino-N-phenylmethyl-N-{1(S) phenylethyl}acetamide hydrochloride: By following the procedure of Example 1(a) but replacing dibenzylamine with α(S)-methyl-N-(phenylmethyl)benzene methanamine, ((S)-N-benzyl-α-methylbenzylamine, Oxford Asymmetry Ltd., Abingdon Oxon, UK), tert-butyl N-{2-oxo-2-{ (phenylmethyl){1(S)-phenylethyl}amino}ethyl}carbamate was made. The Boc group was removed following the procedure of Example 1(b) to give N-{2-oxo-2-{ (phenylmethyl){1(S)-phenylethyl}amino}ethyl}carbamate hydrochloride, which was subjected to reductive amination with benzaldehyde according the procedure of R. F. Borch, Org. Synth., 1972, 52, 124, to give 2-(phenylmethyl)amino-N-phenylmethyl-N-{1(S)-phenylethyl}acetamide hydrochloride.

(b) The title compound: To a solution of 4-acetylbenzoic acid (450 mg, 2.74 mmol) in DMF (15 mL) was added successively 2-(phenylmethyl)amino-N-phenylmethyl-N-{ (1(S)-phenylethyl}acetamide hydrochloride (1.02 g, 2.60 mmol), DIPEA (1.43 mL, 8.22 mmol) and BOP.PF$_6$ (1.21 g, 2.74 mmol). The resulting solution was stirred at room temperature for 4 h, then diluted with EtOAc, washed serially with H$_2$O, 4N aqueous HCl, saturated aqueous NaHCO$_3$, and brine, dried (MgSO$_4$) and concentrated under reduced pressure to give 4-acetyl-N-(phenylmethyl)-N-{2-Oxo-2-{(phenylmethyl){1(S)-phenylethyl}amino}ethyl}benzamide as a light yellow foam. To a solution of this foam in isopropanol (30 mL) was added I$_2$ (1.31 g, 5.2 mmol) and thiourea (792 mg, 10.4 mmol). The resulting mixture was heated at reflux for 18 h, then diluted with EtOAc, washed serially with saturated aqueous NaHCO$_3$, H$_2$O and brine, dried (MgSO$_4$) and concentrated under reduced pressure. The resulting residue was purified by flash chromatography (SiO$_2$, EtOH:CHCl$_3$.EtOAc:hexane, 1:2:2:10)to give the title compound (648 mg, 45% yield) as an off-white solid: $^1$H NMR (400 MHz, DMSO-d$_6$) (mixture of 4 rotamers) δ, 7.85–7.82 (m, 2H), 7.42–6.91 (m, 20H), 5.89–5.87, 5.86–5.79, 5.34–5.30, 5.02–4.96 (4 m, 1H), 4.80–4.68, 4.61–4.47, 4.41–4.34, 4.27–4.19, 4.10–3.96, 3.80–3.76 (6 m, 6H), 1.39–1.33, 1.17 (2 m, 3H); MS (FAB) m/z 561 (mH)$^+$; Anal. Calcd for C$_{34}$H$_{32}$N$_4$O$_2$S: C, 72.83; H, 5.75; N, 9.99. Found: C, 72.20; H, 5.69; N, 9.86.

Example 3

In conjunction with the appropriate starting materials and intermediates, the procedures of Group 3-Examples 1 and 2 can be used to prepare other compounds of Group 3-formula 1b. Examples of compounds thus prepared are listed in Table 1 and 2 of Group 3-Example 3, together with mass spectrum data for the individual compounds and the results obtained from assays demonstrating antiherpes activity. The assays have been described hereinbefore.

TABLE 1

Compound of formula 1b having the structure:

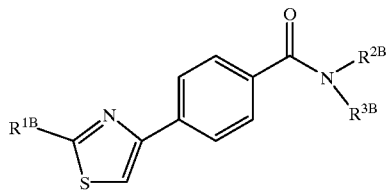

wherein R$^{1B}$ is NH$_2$ and R$^{2B}$ and R$^{3B}$ are designated as follows:

| ENTRY No | R$^{2B}$ | R$^{3B}$ | FAB/MS (m/z) (MH)$^+$ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|
| 1 | H | PhCH$_2$ | 310 | 158 | >30 | 5.5 | 60 |
| 2 | H | (3-FPh)CH$_2$ | 328 | 490 | >30 | 2.5 | 38 |
| 3 | Bu | Bu | 332 | >100 | | 40 | |
| 4* | \multicolumn{2}{c}{H$_2$C-CH$_2$-CH(CH$_2$Ph) (cyclic)} | 378 | 13 | 13 | 21 | |
| 5 | H | CH$_2$C(O)NHCH$_2$Ph | 367 | 20 | 5.0 | 46 | >2.5** |
| 6 | H | CH$_2$C(O)N(CH$_2$Ph)$_2$ | 457 | 2.1 | 0.35 | 0.4 | 12 |
| 7 | H | CH$_2$C(O)N(CH$_2$Ph)(CH(CH$_3$)Ph) | 471 | 1.9 | 1.0 | 3.9 | 8.7 |
| 8 | PhCH$_2$ | CH$_2$C(O)N(CH$_2$Ph)(CH(CH$_3$)Ph) | 561 | >50 | 12.6 | 0.5 | 4 |

TABLE 1-continued

Compound of formula 1b having the structure:

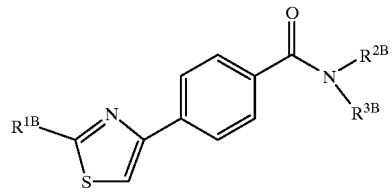

wherein $R^{1B}$ is $NH_2$ and $R^{2B}$ and $R^{3B}$ are designated as follows:

| ENTRY No | $R^{2B}$ | $R^{3B}$ | FAB/MS (m/z) (MH)$^+$ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|
| 9 | H | HC(CH$_2$Ph)C(O)NHCH$_3$ | | >50 | 25 | >109 | >84 |
| 10 | H | HC(CH$_2$Ph)CH$_2$OH | | >50 | | 1.0 | >48 |
| 11 | H | HC(CH$_2$CH$_2$Ph)CH$_2$OH | | >50 | | 71 | |
| 12 | PhCH$_2$ | PhCH$_2$ | 400 | >100 | >6 | 32** | 9 |
| 13 | Me | CH$_2$C(O)N(CH$_2$Ph)$_2$ | 471 | 2.5 | 2.5 | 15.8 | 25 |
| 14 | PhCH$_2$ | CH$_2$C(O)N(CH$_2$-2-pyridyl)$_2$ | 549 | | | | 47 |
| 15 | PhCH$_2$ | CH$_2$C(O)N(CH$_2$Ph)CH$_2$-2-pyridyl | 548 | | | | 41 |
| 16 | PhCH$_2$ | CH$_2$C(O)N(CH$_2$Ph)CH$_2$-4-pyridyl | 548 | | | | 12 |
| 17 | PhCH$_2$ | CH$_2$C(O)N(CH$_2$Ph)CH$_2$CH$_2$-morpholino | 570 | | | | 29 |

TABLE 1-continued

Compound of formula 1b having the structure:

[Structure: R¹ᴮ-thiazole-phenyl-C(O)N(R²ᴮ)(R³ᴮ) where thiazole has N and S, attached at 4-position to phenyl, with R¹ᴮ at 2-position of thiazole]

wherein R¹ᴮ is NH$_2$ and R²ᴮ and R³ᴮ are designated as follows:

| ENTRY No | R²ᴮ | R³ᴮ | FAB/MS (m/z) (MH)$^+$ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|
| 18 | PhCH$_2$ | CH$_2$C(O)N(CH$_2$Ph)CH$_2$-(thiazol-2-yl) | 554 | | | | 9 |
| 19 | PhCH$_2$ | CH$_2$C(O)N(CH$_2$Ph)CH$_2$-(2-OH,3-OMe-phenyl) | 593 | | | | 6 |
| 20 | PhCH$_2$ | CH$_2$C(O)N(CH$_2$Ph)CH$_2$-(1-hydroxycyclohexyl) | 569 | | | | 8.5 |
| 21 | 3-pyridyl-CH$_2$ | CH$_2$C(O)N(CH$_2$Ph)$_2$ | 548 | | | | 10 |
| 22 | 2-pyridyl-CH$_2$ | CH$_2$C(O)N(CH$_2$Ph)$_2$ | 548 | | | | 18 |
| 23 | HC≡CCH$_2$ | CH$_2$C(O)N(CH$_2$Ph)$_2$ | 495 | | | | 14 |
| 24 | PhCH$_2$ | CH$_2$C(O)N(CH$_2$Ph)CH$_2$-(2-hydroxyphenyl) | 563 | | | | 6.1 |
| 25 | PhCH$_2$ | CH$_2$C(O)N(CH$_2$Ph)CH$_2$-(2-OCF$_3$-phenyl) | 631 | | | | 3.8 |
| 26 | PhCH$_2$ | CH$_2$C(O)N(CH$_2$Ph)CH$_2$-(2-methylphenyl) | 561 | | | | 5 |

TABLE 1-continued
Compound of formula 1b having the structure:
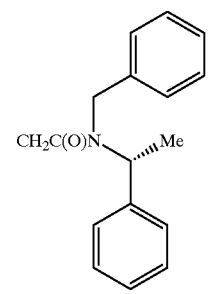
wherein $R^{1B}$ is $NH_2$ and $R^{2B}$ and $R^{3B}$ are designated as follows:
| ENTRY No | $R^{2B}$ | $R^{3B}$ | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|
| 27 | $PhCH_2$ | 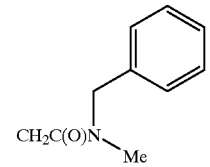 | 561 | | | | 7 |
| 28 | $PhCH_2$ | 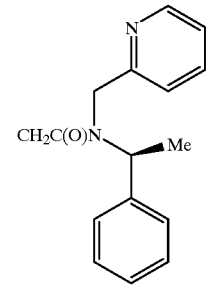 | 485 | | | | 18 |
| 29 | $PhCH_2$ | 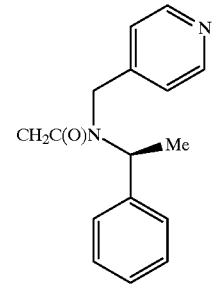 | 562 | | | | 18 |
| 30 | $PhCH_2$ | 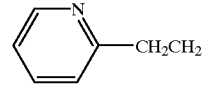 | 562 | | | | 21 |
| 31 |  | $CH_2C(O)N(CH_2Ph)_2$ | 562 | | | | 16 |

TABLE 1-continued

Compound of formula 1b having the structure:

[Structure: thiazole with R^1B at 2-position, connected at 4-position to a phenyl group bearing a C(=O)N(R^2B)(R^3B) amide]

| ENTRY No | R^2B | R^3B | wherein R^1B is NH₂ and R^2B and R^3B are designated as follows: FAB/MS (m/z) (MH)⁺ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|
| 32 | Ph-(S)—CHMe | CH₂C(O)N(CH₂Ph)₂ | 561 | | | | 4.5 |
| 33 | Ph-(R)—CHMe | CH₂C(O)N(CH₂Ph)₂ | 561 | | | | 7.0 |
| 34 | benzimidazol-2-yl-CH₂ | CH₂C(O)N(CH₂Ph)₂ | 587 | | | | 7.0 |
| 35 | 2-furyl-CH₂ | CH₂C(O)N(CH₂Ph)₂ | 537 | | | | 7.7 |
| 36 | 2-pyridyl-CH₂ | CH₂C(O)N(CH₂Ph)(CH(Me)Ph) | 562 | | | | 7.0 |
| 37 | 3-pyridyl-CH₂ | CH₂C(O)N(CH₂Ph)(CH(Me)Ph) | 562 | | | | 11 |

TABLE 1-continued

Compound of formula 1b having the structure:

wherein R$^{1B}$ is NH$_2$ and R$^{2B}$ and R$^{3B}$ are designated as follows:

| ENTRY No | R$^{2B}$ | R$^{3B}$ | FAB/MS (m/z) (MH)$^+$ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|
| 38 | 4-pyridyl-CH$_2$ | CH$_2$C(O)N(Me)(CH$_2$Ph)(CHPh) | 562 | | | | 16 |
| 39 | 2-pyridyl-CH$_2$CH$_2$ | CH$_2$C(O)N(Me)(CH$_2$Ph)(CHPh) | 576 | | | | 14 |
| 40 | Ph-(R)—CHMe | CH$_2$C(O)N(Me)(CH$_2$Ph)(CHPh) | 575 | | | | 3.0 |
| 41 | benzimidazol-2-yl-CH$_2$ | CH$_2$C(O)N(Me)(CH$_2$Ph)(CHPh) | 601 | | | | 5.3 |

TABLE 1-continued
Compound of formula 1b having the structure:
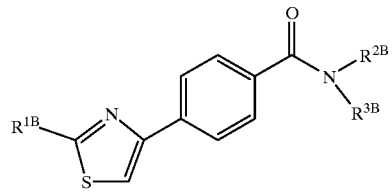
| ENTRY No | wherein R¹ᴮ is NH₂ and R²ᴮ and R³ᴮ are designated as follows: R²ᴮ | R³ᴮ | FAB/MS (m/z) (MH)⁺ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|
| 42 | HC≡C—CH₂ | CH₂C(O)N(CHPh)(Me)(CH₂Ph) | 509 | | | | 15 |
| 43 | cyclopropyl-CH₂ | CH₂C(O)N(CHPh)(Me)(CH₂Ph) | 525 | | | | 12 |
| 44 | PhCH₂CH₂ | CH₂C(O)N(CHPh)(Me)(CH₂Ph) | 575 | | | | 7.0 |

TABLE 1-continued

Compound of formula 1b having the structure:

[Structure: 2-amino-thiazole (R¹ᴮ) at position connected to phenyl ring bearing para-C(O)N(R²ᴮ)(R³ᴮ) amide]

wherein R¹ᴮ is $NH_2$ and R²ᴮ and R³ᴮ are designated as follows:

| ENTRY No | R²ᴮ | R³ᴮ | FAB/MS (m/z) (MH)⁺ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|
| 45 | 1-(phenyl-methyl)-piperidin-4-yl | $CH_2C(O)N$—CH(Me)(Ph) with N-benzyl (i.e., N-benzyl, α-methylbenzyl amide linker) | 644 | | | | 5.5 |
| 46 | H | $CH_2C(O)N$(benzyl)—CH(Me)-(2-hydroxy-3-methoxyphenyl) | 489 | | | | 13 |
| 47 | H | $CH_2C(O)N(CH_2Ph)CH_2$-(thiazol-2-yl) | 464 | | | | 14 |
| 48 | H | $CH_2C(O)N(CH_2Ph)CH_2$-(2-hydroxyphenyl) | 473 | | | | 7.3 |
| 49 | H | $CH_2CH_2N$(benzyl)—CH(Me)(Ph) | 457 | | | | 6.3 |
| 50 | H | $CH_2CH_2N(CH_2Ph)_2$ | 443 | | | | 14 |

TABLE 1-continued

Compound of formula 1b having the structure:

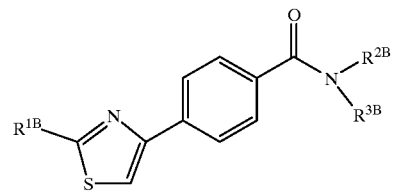

wherein $R^{1B}$ is $NH_2$ and $R^{2B}$ and $R^{3B}$ are designated as follows:

| ENTRY No | $R^{2B}$ | $R^{3B}$ | FAB/MS (m/z) (MH)+ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|
| 51 | PhCH$_2$ | CH$_2$CH$_2$N(CH$_2$Ph)(CH(Me)Ph) | 547 | | | | 5.8 |

*$R^{2B}$ and $R^{3B}$ together with the N atom to which they are attached form a heterocycle
**Cytotoxic at this concentration

TABLE 2

Compound of formula 1b having the structure:

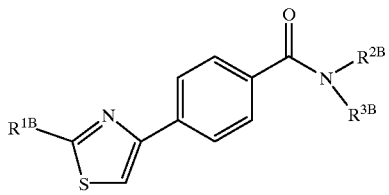

wherein $R^{1B}$, $R^{2B}$ and $R^{3B}$ are designated as follows:

| ENTRY No | $R^{1B}$ | $R^{2B}$ | $R^{3B}$ | FAB/MS (m/z) (MH)+ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|---|
| 1 | Me$_3$COC(O)NH | H | CH$_2$C(O)N(CH$_2$Ph)$_2$ | 557 | | | | <1.2 |
| 2 | Me$_3$COC(O)NH | H | CH$_2$C(O)N(CH$_2$Ph)(CH(CH$_3$)Ph) | 571 | | | | <1.2 |

Group 4: Thiazolylphenoxyacetamide Derivatives

According to another embodiment of this invention, the present application refers to Group 4 thiazolylphenoxyacetamide derivatives having antiherpes activity. The selective action of these compounds against herpes viruses, combined with a wide margin of safety, renders the compounds desirable agents for combating herpes infections.

The thiazolylphenoxyacetamide derivatives of the present invention can be characterized structurally by the presence of a (4-thiazolylphenoxy)acetamide moiety. Compounds possessing such a moiety have been reported previously, for example:

A. Wissner, European patent application 458,037, published Nov. 27, 1991; and

A. Wissner, U.S. Pat. No. 5,077,409, issued Dec. 31, 1991

The present thiazolylphenoxyacetamide derivatives can be distinguished readily from the prior art compounds in that they possess different chemical structures and biological activities.

The Group 4 thiazolylphenoxyacetamide derivatives of this invention can also be represented by formula 1c:

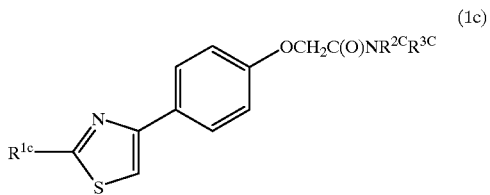

(1c)

wherein $R^{1C}$ has the same meaning as R as defined hereinbefore and $R^{2C}$ and $R^{3C}$ are as defined hereinbefore.

A preferred set of Group 4 compounds of this invention are represented by Group 4-formula 1c wherein $R^{1C}$ is hydrogen, lower alkyl, amino, lower alkylamino, di(lower alkyl)amino, lower alkanoylamino or (lower alkoxycarbonyl) amino; $R^{2C}$ and $R^{3C}$ each independently is hydrogen, lower alkyl, phenyl, phenyl-(1-3C)alkyl or phenyl-(1-3C)alkyl monosubstituted or disubstituted on the aromatic portion thereof with a substituent selected independently from the group consisting of halo, hydroxy, lower alkoxy and lower alkyl; 1-indanyl, diphenylmethyl, lower cycloalkyl, (lower cycloalkyl)-(1-3C)alkyl or (Het)-(1-3C) alkyl wherein Het is as defined hereinbefore; or a therapeutically acceptable acid addition salt thereof.

A more preferred set of Group 4 compounds is compounds of Group 4-formula 1c wherein $R^{1C}$ is amino, methylamino, acetylamino or (1,1-dimethylethoxycarbonyl) amino; $R^{2C}$ and $R^{3C}$ are independently hydrogen, methyl, ethyl, propyl, butyl, 1,1-dimethylethyl, 2,2-dimethylpropyl, phenyl, phenylmethyl, 1(R)- or 1(S)-phenylethyl, 2-phenylethyl, {4-(1,1-dimethylethyl)phenyl}methyl, (4-chlorophenyl)methyl, (3-fluorophenyl)methyl, (4-fluorophenyl)methyl, (4-methoxyphenyl)methyl, 1-indanyl, diphenylmethyl, cyclohexyl, cyclopentylmethyl, cyclohexylmethyl, cycloheptylmethyl, 2-cyclohexylethyl, 2-(4-morpholinyl)ethyl, 2-pyridinylmethyl, 3-pyridinylmethyl, 4-pyridinylmethyl, 2-(2-pyridinyl)ethyl, 2-(3-pyridinyl)ethyl, 2-(4-pyridinyl)ethyl, 2-thienylmethyl or 3-thienylmethyl; or a therapeutically acceptable acid addition salt thereof.

A most preferred set of Group 4 compounds is represented by Group 4-formula 1c wherein $R^{1C}$ is amino, $R^{2C}$ is hydrogen or phenylmethyl, and $R^{3C}$ is phenyl, phenylmethyl, 2-phenylethyl, {4-(1,1-dimethylethyl) phenyl}methyl, (3-fluorophenyl)methyl, 1-indanyl, cyclohexyl, cyclohexylmethyl, 2-pyridinylmethyl, 3-pyridinylmethyl or 4-pyridinylmethyl; or a therapeutically acceptable acid addition salt thereof.

Another most preferred set of Group 4 compounds is represented by Group 4-formula 1c wherein $R^{1C}$ is amino, methylamino or acetylamino, $R^{2C}$ is hydrogen or phenylmethyl, and $R^{3C}$ is phenyl, phenylmethyl, cyclohexyl or cyclohexylmethyl; or a therapeutically acceptable acid addition salt thereof.

Included within the scope of this invention is a pharmaceutical composition comprising an antiherpes virally effective amount of a compound of Group 4-formula 1c, or a therapeutically acceptable acid addition salt thereof, and a pharmaceutically or veterinarily acceptable carrier.

Still another aspect of this invention involves a method for treating acyclovir-resistant herpes infections in a mammal which comprises administering to the mammal an anti-acyclovir-resistant herpes effective amount of a compound of Group 4-formula 1c as defined herein, or a therapeutically acceptable acid addition salt thereof.

Process for preparing the Compounds of Group 4

The compounds of Group 4 can be prepared by a variety of processes involving known methods. Description of the methods are found in standard textbooks such as "Annual Reports In Organic Synthesis—1994", P. M. Weintraub et al., Eds., Academic Press, Inc., San Diego, Calif., USA, 1994 (and the preceding annual reports), "Vogel's Textbook of Practical Organic Chemistry", B. S. Furniss et al., Eds., Longman Group Limited, Essex, UK, 1986, and "Comprehensive Organic Synthesis", B. M. Trost and I. Fleming, Eds., Pergamon Press, Oxford, UK, 1991, Volumes 1 to 8.

A general process can be represented by Group 4-scheme 1:

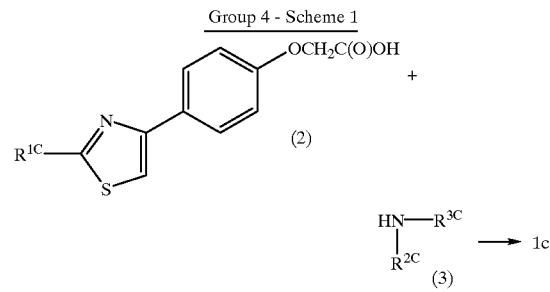

wherein $R^{1C}$, and $R^{2C}$ are as defined herein.

According to scheme 1, the thiazolylphenoxyacetic acid of formula 2 is coupled with a primary or secondary amine of formula 3 to give the corresponding compound of Group 4-formula 1c. This coupling is effected by the classical dehydrative coupling of a free carboxyl of one reactant with the free amino group of the other reactant in the presence of coupling agent to form a linking amide bond, as described hereinbefore.

In turn, the thiazolylphenoxyacetic acid of formula 2 wherein $R^{1C}$ is amino can be prepared from an acetophenone derivative of formula 4 according to Group 4-scheme 2:

Group 4 - Scheme 2

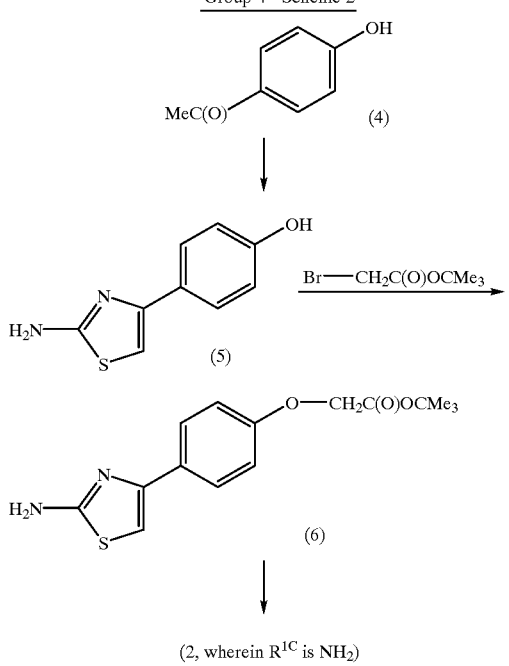

(2, wherein $R^{1C}$ is $NH_2$)

According to Group 4-scheme 2, 4'-hydroxyacetophenone (Aldrich Chemical Co., Milwaukee, Wis., USA) was reacted with thiourea and iodine according to the method of R. M. Dodson and L. C. King, J. Amer. Chem. Soc. 1945, 67, 2242 to give 4-(2-amino-4-thiazolyl)phenol (5). Reaction of the latter compound with 1,1-dimethylethyl 2-bromoacetate in the presence of potassium carbonate gave 1,1-dimethylethyl 2-{4-(2-amino-4-thiazolyl)phenoxy}acetate (6). Subsequent hydrolysis of the later compound gave the thiazolylphenoxy-acetic acid derivative of formula 2 wherein $R^{1C}$ is amino.

Again in turn, the thiazolylphenoxyacetic acid of formula 2 wherein $R^{1C}$ is hydrogen, lower alkyl, amino, lower alkylamino or di(lower alkyl)amino can be prepared according to Group 4-scheme 3.

Group 4 - Scheme 3

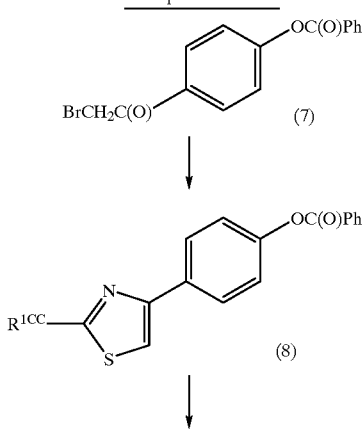

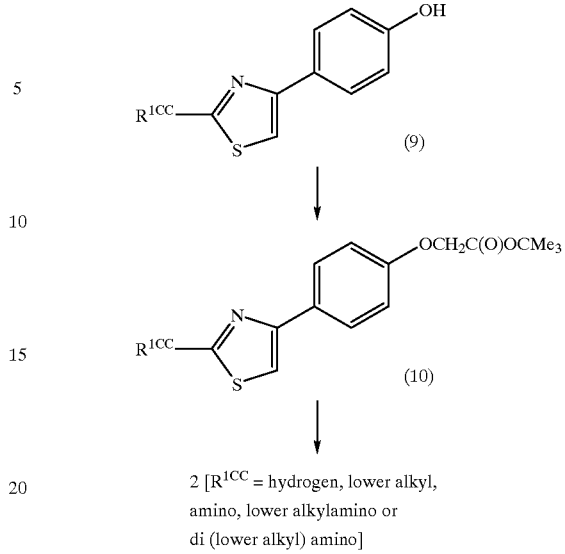

2 [$R^{1CC}$ = hydrogen, lower alkyl, amino, lower alkylamino or di (lower alkyl) amino]

wherein $R^{1CC}$ is hydrogen, lower alkyl, amino, lower alkylamino or di (lower alkyl) amino.

According to Group 4-scheme 3, the compound of formula 7, 4-(bromoacetyl)phenyl benzoate (Aldrich Chemical Co.) is reacted with an appropriate thioamide or thiourea of formula $H_2N—C(S)—R^{1CC}$ wherein $R^{1CC}$ is as defined hereinbefore, according to the classical reaction described by R. H. Wiley et al., Organic Reactions 1951, 6, 369–373 for preparing thiazole compounds from thioamides or thioureas and α-halocarbonyl compounds, to obtain the corresponding protected thiazolylphenol derivative of formula 8. Thereafter, acid hydrolysis of the latter derivative effects the removal of the benzoyl protective group to give the corresponding thiazolylphenol of formula 9 which on reaction with 1,1-dimethylethyl 2-bromoacetate in the presence of potassium carbonate gives the 1,1-dimethyl ester of formula 10. Subsequent hydrolysis of the latter ester yields the thiazolylphenoxy-acetic acid of formula 2 wherein $R^1$ is hydrogen, lower alkyl, amino, lower alkylamino or di(lower alkyl)amino. The thiazolylphenoxyacetic acid of formula 2 wherein $R^{1C}$ is amino can serve as an intermediate for transformation by standard methods to thiazolylphenoxy-acetic acids of formula 2 wherein $R^{1C}$ is lower alkanoylamino or lower alkoxycarbonyl.

The starting materials for the preceding processes are known, as noted hereinabove for compounds 4 and 7, or they can be prepared by standard methods.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, the reaction can be successfully performed by conventional modification known to those skilled in the art, e.g. by appropriate protection of interfering groups, by changing to alternative conventional reagents, by routine modification of reaction conditions, or by modification illustrated in the examples herein.

Furthermore, if desired, the compound of Group 4-formula 1c can be obtained in the form of a therapeutically acceptable acid addition salt. Such salts can be considered as biological equivalent of the compounds of Group 4-formula 1c. Examples of such salts are those formed with hydrochloric acid, sulfuric acid, phosphoric acid, formic acid, acetic acid or citric acid.

Antiherpes Activity

The antiviral activity of the compounds of Group 4-formula 1c, or a therapeutically acceptable acid addition salt thereof, can be demonstrated by biochemical, microbiological and biological procedures in the same manner as described previously for the compounds of Group 1-formula 1. Likewise the compounds of Group 4-formula 1c, or a therapeutically acceptable acid addition salt thereof, can be formulated and used as antiviral agents in the same manner as described for the compounds of Group 1-formula 1.

The following examples further illustrate this invention. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts ($\delta$) are reported in parts per million. The concentrations for the optical rotations are expressed in grams of the compound per 100 mL of solution. Abbreviations or symbols used in the examples are as defined hereinbefore.

GROUP 4 EXAMPLES

Example 1

4-(2-Amino-4-thiazolyl)phenol

Thiourea (30.45 g, 400 mmol) and iodine (50.76 g, 200 mmol) were added to a solution of 4'-hydroxyacetophenone (27.23 g, 200 mmol) in isopropanol (400 mL). The resulting mixture was heated at reflux for 18 h, then diluted with $H_2O$ and washed with $Et_2O$. The aqueous layer was rendered basic with a saturated aqueous solution of $NaHCO_3$ and then extracted with EtOAc. The organic extract was washed with brine, dried ($MgSO_4$) and concentrated under reduced pressure to afford 15 g of an orange foam. The foam was purified by flash chromatography ($SiO_2$, 3:1, EtOAc:hexane) to afford the title compound (9.41 g, 25% yield) as a pale yellow solid: $^1$H NMR (400 MHz, DMSO-$d_6$) $\delta$ 9.42 (s, 1H), 7.59 (d, J=8.6 Hz, 2H), 6.93 (s, 2H), 6.73 (d, J=8.6 Hz, 2H), 6.71 (s, 1H); MS (CI, $NH_3$) m/z 193 (MH)$^+$.

Example 2

1,1-Dimethylethyl 2-{4-(2-amino-4-thiazolyl)phenoxy}acetate.

Potassium carbonate (3.80 g, 27.5 mmol) and tert-butyl 2-bromoacetate (4.04 mL, 25.0 mmol) were added to a solution of the product of example 1 (4.81 g, 25.0 mmol) in THF (125 mL). The resulting mixture was heated at reflux for 72 h and then diluted with EtOAc. The mixture was washed with a saturated aqueous solution of $NaHCO_3$ and then brine, dried ($MgSO_4$) and concentrated under reduced pressure. The crude yellow oil obtained was purified by flash chromatography ($SiO_2$, 1:2 to 2:3 EtOAc:hexane) to afford 3.97 g (52% yield) of the title compound as a pale yellow solid: $^1$H NMR (400 MHz, DMSO-$d_6$) $\delta$ 7.71 (d, J=8.2 Hz, 2H), 6.97 (s, 2H), 6.88 (d, J=8.2 Hz, 2H ), 6.83 (s, 1H), 4.65 (s, 2H), 1.43 (s, 9H); MS (FAB) m/z 307 (MH)$^+$.

Example 3

2-{4-(2-Amino-4-thiazolyl)phenoxy}acetic acid

Trifluoroacetic acid (50 mL) was added to a solution of the product of example 2 (3.81 g, 12.4 mmol) in $CH_2Cl_2$ (50 mL). The resulting mixture was stirred at room temperature (20–22°) for 4 h, then concentrated under reduced pressure (coevaporated with $CH_2Cl_2$ and then $Et_2O$). The residue was triturated with $Et_2O$, then filtered and dried to afford 4.45 g (quantitative yield) of the title compound as a white solid: $^1$H NMR (400 MHz, DMSO-$d_6$) $\delta$ 7.67 (d, J=8.8 Hz, 2H), 6.97 (d, J=8.8 Hz, 2H), 6.96 (s, 1H), 4.72 (s, 2H). The product was used without further purification for the following reaction (example 4).

Example 4

2-{4-(2-Amino-4-thiazolyl)phenoxy}-N-(cyclohexylmethyl)acetamide (1c: $R^{1C}$=NH$_2$, $R^{2C}$=H and $R^{3C}$=cyclohexylmethyl)

To a solution of the product of example 3 (358 mg, 1.0 mmol) in DMF (10 mL) were added successively cyclohexanemethylamine (130 µL, 1.0 mmol), DIPEA (700 µL, 4.0 mmol) and TBTU (321 mg, 1.0 mmol). The resulting mixture was stirred at room temperature for 18 h and then diluted with EtOAc. The mixture was washed with a saturated aqueous solution of $NaHCO_3$ and then brine, dried ($MgSO_4$) and concentrated under reduced pressure. The residue was purified by flash chromatography ($SiO_2$, 4:1, EtOAc:hexane) to afford the title compound (300 mg, 87% yield) as a white solid: M.p. 145–147°; $^1$H NMR (400 MHz, DMSO-$d_6$) $\delta$ 8.00 (broad t, J=6.0 Hz, 1H), 7.71 (d, J=8.7 Hz, 2H), 6.98 (s, 2H), 6.94 (d, J=8.7 Hz, 2H), 6.84 (s, 1H), 4.48 (s, 2H), 2.97 (t, J=6.4 Hz, 2H), 0.82–1.66 (m, 11H); MS (FAB) m/z 346 (MH)$^+$. Anal. Calcd for $C_{18}H_{23}N_3O_2S$: C, 62.58; H, 6.71; N, 12.16. Found: C, 62.48; H, 6.74; N, 12.17.

Example 5

In conjunction with the appropriate starting materials and intermediates, the procedures of Group 4-examples 1 to 4 can be used to prepare other compounds of Group 4-formula 1c. Examples of compounds thus prepared are listed in Table 1 and 2 of Group 4-example 5, together with mass spectrum data for the individual compounds and the results obtained from three assays demonstrating antiherpes activity. The assays are as described hereinbefore.

TABLE 1

Compound of formula 1c having the structure:

[Structure of compound 1c: R¹ᶜ-thiazole-phenyl-OCH₂C(O)NR²ᶜR³ᶜ (1c)]

| ENTRY No | wherein R¹ᶜ is NH₂ and R²ᶜ and R³ᶜ are designated as follows: R²ᶜ | R³ᶜ | FAB/MS (m/z) (MH)⁺ | HSV-1 IC$_{50}$ ($\mu$M) | HSV-1 EC$_{50}$ ($\mu$M) | ELISA CMV EC$_{50}$ ($\mu$M) | PRA CMV EC$_{50}$ ($\mu$M) |
|---|---|---|---|---|---|---|---|
| 1 | H | PhCH₂ | 340 | 35 | 6.5 | 0.6 | 12 |
| 2 | H | cyclohexyl-CH₂ | 346 | 8.4 | 2.0 | 1.2 | 35 |
| 3 | H | PhCH₂CH₂ | 354 | >50 | 9.6 | 6.0 | 45 |
| 4 | PhCH₂ | PhCH₂ | 430 | 17 | 2.8 | 4.0 | 13* |
| 5 | H | 3-pyridyl-CH₂ | 341 | 48 | 10.6 | 60 | >94 |
| 6 | Me | PhCH₂ | 354 | 12 | 4.7 | 4.0 | 38 |
| 7 | H | Ph | 326 | 37 | 15.8 | 8.4 | 38 |
| 8 | H | 2-pyridyl-CH₂ | 341 | 16 | | | >92 |
| 9 | H | 4-pyridyl-CH₂ | 341 | 65 | | | >18* |
| 10 | H | indanyl (CH₂-CH-CH₂) | 366 | 30 | | | >19* |
| 11 | H | Ph₂CH | 416 | 6.8 | | | 40* |
| 12 | H | cyclohexyl | 332 | >50 | | | 50 |
| 13 | Me | cyclohexyl | 346 | 26 | | | >57 |
| 14 | H | (4-Me₃CPh)CH₂ | 396 | 12.8 | | | >33* |
| 15 | H | (4-FPh)CH₂ | 358 | 35 | | | >16* |
| 16 | H | (4-MeOPh)CH₂ | 370 | 48 | | | >20* |
| 17 | H | (3-FPh)CH₂ | 358 | 13.5 | | | >21* |

*Cytotoxic at this concentration

TABLE 2

Compound of formula 1c having the structure:

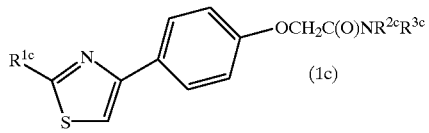

(1c)

| ENTRY No | wherein $R^{1c}$, $R^{2c}$ and $R^{3c}$ are designated as follows: | | | FAB/MS (m/z) $(MH)^+$ | HSV-1 $IC_{50}$ ($\mu M$) | HSV-1 $EC_{50}$ ($\mu M$) | ELISA CMV $EC_{50}$ ($\mu M$) | PRA CMV $EC_{50}$ ($\mu M$) |
|---|---|---|---|---|---|---|---|---|
| | $R^{1c}$ | $R^{2c}$ | $R^{3c}$ | | | | | |
| 1 | $Me_3COC(O)NH$ | $PhCH_2$ | $PhCH_2$ | 530 | >50 | | | 75 |
| 2 | $MeC(O)MH$ | $PhCH_2$ | $PhCH_2$ | 472 | >50 | | | 15 |
| 3 | NHMe | $PhCH_2$ | $PhCH_2$ | 444 | >50 | | | 15 |

*Cytotoxic at this concentration

Group 5: Thiazolylphenylethylamine Derivatives

According to another embodiment of this invention, the present application refers to Group 5 thiazolylphenylethylamine derivatives having antiherpes activity. The selective action of these compounds against these viruses, combined with a wide margin of safety, renders the compounds as desirable agents for combating herpes infections.

These thiazolylphenylethylamine derivatives can be characterized structurally by the presence of a {4-(4-thiazolyl) phenyl}ethylamine moiety. Compounds possesing such a moeity have been reported previously, for example:

Y. Kawamatsu et al., Eur. J. Med. Chem.-Chimica Therapeutica, 1981, 16, 355;

T. Nakao et al., Japanese patent application 63-060978, published Sep. 1, 1986; Chem. Abstr., 1989, 110, 716, 135228r;

J. A. Lowe, European patent application 279,598, published Aug. 24, 1988;

A. A. Nagel, European patent application 372,776, published Jun. 13, 1990;

J. A. Lowe et al., J. Med. Chem., 1991, 34, 1860; and

Y. Katsura et al., European patent application 545,376, published Jun. 9, 1993.

The present thiazolylphenylethylamine derivatives can be distinguished readily from the prior art compounds in that they possess different chemical structures and biological activities.

The Group 5 thiazolylphenylethylamine derivatives of this invention can also be represented by formula 1d

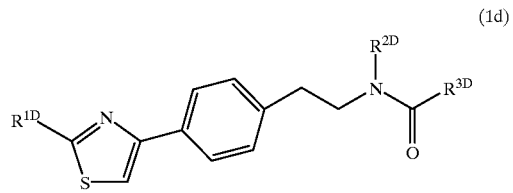

(1d)

wherein $R^{1D}$ has the same meaning as R defined hereinbefore and $R^{2D}$ and $R^{3D}$ are as defined hereinbefore.

A preferred set of Group 5 compounds of this invention is represented by Group 5-formula 1d wherein $R^{1D}$ is hydrogen, lower alkyl, amino, lower alkylamino, di(lower alkyl)amino, lower alkanoylamino, (lower alkoxycarbonyl)amino, or di(lower alkoxycarbonyl)amino;

$R^{2D}$ is hydrogen, lower alkyl, phenyl-(1-3C)alkyl, phenyl-(1-3C)alkyl monosubstituted or disubstituted on the aromatic portion thereof with a halo, hydroxy, lower alkoxy or lower alkyl; (lower cycloalkyl)-(1-3C)alkyl, or (Het)-(1-3C)alkyl wherein Het is as defined hereinbefore;

$R^{3D}$ is lower alkyl, lower alkyl monosubstituted, disubstituted or trisubstituted with a halo; phenyl unsubstituted, monosubstituted or disubstituted with a halo, hydroxy, lower alkoxy or lower alkyl; phenyl-(1-3C)alkyl unsubstituted, monosubstituted or disubstituted on the aromatic portion thereof with a halo, hydroxy, lower alkoxy or lower alkyl; lower cycloalkyl, (lower cycloalkyl)-(1-3C)alkyl, Het wherein Het is as defined hereinbefore, (Het)-(1-3C)alkyl wherein Het is as defined hereinbefore; lower alkylamino, di(lower alkyl)amino or phenyl-(1-3C)alkylamino unsubstituted, monosubstituted or disubstituted on the aromatic portion thereof with a halo, hydroxy, lower alkoxy or lower alkyl; or a therapeutically acceptable acid addition salt thereof.

A more preferred set of Group 5 compounds are represented by Group 5-formula 1d wherein $R^{1D}$ is amino, methylamino, dimethylamino, acetylamino, (1,1-dimethylethoxycarbonyl)amino or di(1,1-dimethylethoxycarbonyl)amino;

$R^{2D}$ is hydrogen, methyl, ethyl, propyl, butyl, 2-methylpropyl, 2,2-dimethylpropyl, phenylmethyl, 2-phenylethyl, (4-chlorophenyl)methyl, (2-fluorophenyl) methyl, (3-fluorophenyl)methyl, (4-fluorophenyl)methyl, (4-methoxyphenyl)methyl, cyclopentylmethyl, cyclohexylmethyl, 2-cyclohexylethyl, 2-(4-morpholinyl) ethyl, 2-pyridinylmethyl, 3-pyridinylmethyl, 4-pyridinylmethyl, 2-(2-pyridinyl)ethyl, 2-(3-pyridinyl) ethyl, 2-(4-pyridinyl)ethyl, 2-thienylmethyl or 3-thienylmethyl;

$R^{3D}$ is methyl, ethyl, propyl, butyl, 2-methylpropyl, 2,2-dimethylpropyl, trifluoromethyl, phenyl, 4-chlorophenyl, 2-fluorophenyl, 3-fluorophenyl, 4-fluorophenyl, 4-methoxyphenyl, 5-chloro-2-methoxyphenyl, phenylmethyl, 2-phenylethyl, (4-chlorophenyl)methyl, (2-fluorophenyl)methyl, (3-fluorophenyl)methyl, (4-fluorophenyl)methyl, (4-methoxyphenyl)methyl, cyclopentyl, cyclohexyl, cyclopentylmethyl, cyclohexylmethyl, 2-cyclohexylethyl, 2-pyridinyl, 3-pyridinyl, 4-pyridinyl, 2-thienyl, 3-thienyl, 2-(4-morpholinyl)ethyl, 2-pyridinylmethyl, 3-pyridinylmethyl, 4-pyridinylmethyl, 2-(2-pyridinyl)ethyl, 2-(3-pyridinyl)

ethyl, 2-(4-pyridinyl)ethyl, 2-thienylmethyl, 3-thienylmethyl, methylamino, ethylamino, propylamino, butylamino, (2-methylpropyl)amino, (2,2-dimethylpropyl)amino, dimethylamino, diethylamino, dipropylamino, dibutylamino, di(2-methylpropyl)amino, {di(2,2-dimethylpropyl)}amino, (phenylmethyl)amino, (2-phenylethyl)amino, {(4-chlorophenyl)methyl}amino, {(2-fluorophenyl)methyl}amino, {(3-fluorophenyl)methyl}amino, {(4-fluorophenyl)methyl}amino, {(4-methoxyphenyl)methyl}amino; or a therapeutically acceptable acid addition salt thereof.

A most preferred set of Group 5 compounds are represented by Group 5-formula 1d wherein $R^{1D}$ is amino;
$R^{2D}$ is hydrogen or phenylmethyl;
$R^{3D}$ is phenyl, phenylmethyl, {(4-fluorophenyl)methyl}amino, cyclohexyl or dibutylamino; or a therapeutically acceptable acid addition salt thereof.

Another most preferred set of Group 5 compounds are represented by Group 5-formula 1d wherein $R^{1D}$ is amino, (1,1-dimethylethylcarbonyl)amino or di(1,1-dimethylethoxycarbonyl)amino;
$R^{2D}$ is hydrogen or phenylmethyl; and
$R^{3D}$ is 2,2-dimethylpropyl, trifluoromethyl, phenyl, phenylmethyl, 4-pyridinyl or dibutylamino; or a therapeutically acceptable acid addition salt thereof.

Included within the scope of this invention is a pharmaceutical composition comprising an antiherpes virally effective amount of a compound of Group 5 as defined herein, or a therapeutically acceptable acid addition salt thereof, and a pharmaceutically or veterinarily acceptable carrier.

Still another aspect of this invention involves a method for treating acyclovir-resistant herpes infections in a mammal which comprises administering to the mammal an anti-acyclovir-resistant herpes effective amount of a compound of Group 5 as defined herein, or a therapeutically acceptable acid addition salt thereof.

Process for preparing the compounds of Group 5

The compounds of Group 5 can be prepared by a variety of processes involving known methods. Description of the methods are found in standard textbooks such as "Annual Reports In Organic Synthesis—1994", P. M. Weintraub et al., Eds., Academic Press, Inc., San Diego, Calif., USA, 1994 (and the preceding annual reports), "Vogel's Textbook of Practical Organic Chemistry", B. S. Furniss et al., Eds., Longman Group Limited, Essex, UK, 1986, and "Comprehensive Organic Synthesis", B. M. Trost and I. Fleming, Eds., Pergamon Press, Oxford, UK, 1991, Volumes 1 to 8.

A general process to prepare compounds of Group 5-formula 1d can be represented by Group 5-scheme 1:

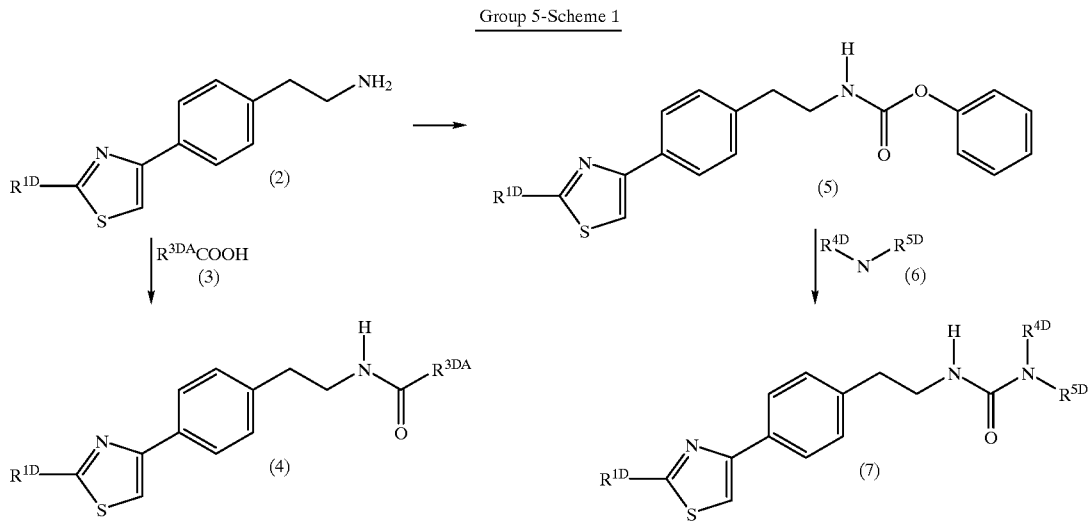

Group 5-Scheme 1

According to Group 5-scheme 1, a 4-thiazolylphenyl derivative of formula 2, wherein $R^{1D}$ is as defined herein, is coupled with a carboxylic acid derivative of formula 3, wherein $R^{3DA}$ is lower alkyl, lower alkyl monosubstituted, disubstituted or trisubstituted with a halo; phenyl unsubstituted, monosubstituted or disubstituted with a halo, hydroxy, lower alkoxy or lower alkyl; phenyl(lower alkyl) unsubstituted, monosubstituted or disubstituted on the aromatic portion thereof with a halo, hydroxy, lower alkoxy or lower alkyl; lower cycloalkyl, (lower cycloalkyl)-(lower alkyl), Het wherein Het is as defined hereinbefore, or (Het)-(lower alkyl) wherein Het is as defined hereinbefore; to give the amide derivative of formula 4, which is a compound of Group 5-formula 1d.

Alternatively, the 4-thiazolylphenyl derivative of formula 2 is reacted with phenyl chloroformate in the presence of a base to give the carbamate derivative of formula 5. The carbamate derivative of formula 5 is reacted with an amine of formula 6, wherein $R^{4D}$ is hydrogen or lower alkyl, and $R^{5D}$ is lower alkyl or phenyl lower alkyl unsubstituted, monosubstituted or disubstituted on the aromatic portion thereof with a halo, hydroxy, lower alkoxy or lower alkyl; to give the ureido derivative of formula 7, which is also a compound of Group 5-formula 1d.

The coupling of the 4-thiazolylphenyl derivative of formula 2 and the carboxylic acid of formula 3 is effected by the classical dehydrative coupling of a free carboxyl of one reactant with the free amino group of the other reactant in the presence of a coupling agent to form a linking amide bond, as described hereinbefore.

The compounds of formula 4 or formula 7, albeit compounds of Group 5-formula 1d, can also serve as intermediates for further elaboration by standard methods (e.g., N-alkylation, acylation, carbamate formation, etc.) with the appropriate agent to give other compounds of Group 5-formula 1d, as well as corresponding compounds of Group 5-formula 1d in which $R^{2D}$ is other than hydrogen. A convenient and practical process to prepare the requisite 4-thiazolylphenyl derivative of formula 2 of Group 5-scheme 1 is illustrated by Group 5-scheme 2:

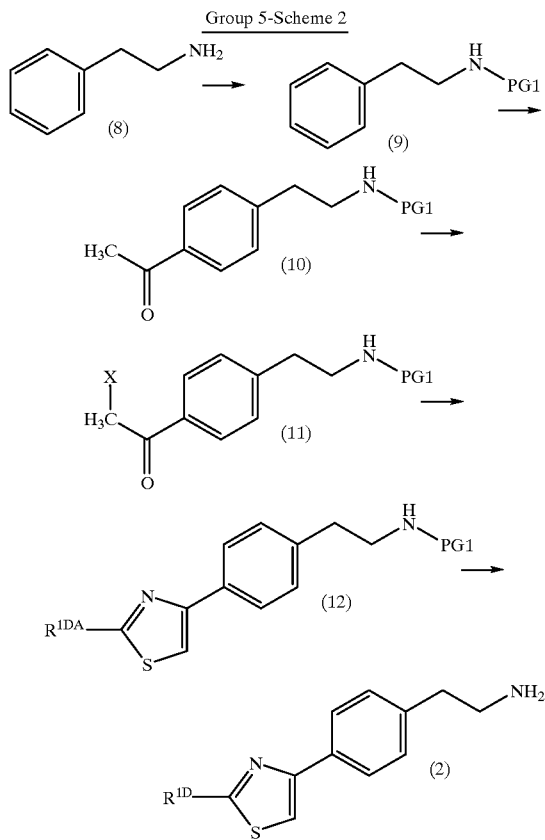

Group 5-Scheme 2

According to Group 5-scheme 2, phenethylamine of formula 8 is protected with an amino protecting group (PG1) to give a corresponding amino protected derivative of formula 9. The amino protected derivative of formula 9 is then reacted with acetyl chloride in the prescence of $AlCl_3$ in an inert solvent to give the corresponding methyl ketone derivative of formula 10, which is then reacted with $Br_2$, $Cl_2$ or $I_2$ to give the corresponding α-haloketone derivative of formula 11 wherein X is Br, Cl or I. The α-haloketone derivative of formula 11 is reacted with a thioamide of the formula $H_2N$—$C(S)$—$R^{1DA}$ wherein $R^{1DA}$ is hydrogen, lower alkyl, amino, lower alkylamino or di(lower alkyl) amino according to the classical reaction described by R. H. Wiley et al, Organic Reactions, 1951, 6, 367–374 for preparing thiazole compounds from thioamides and α-halocarbonyl compounds, to obtain the corresponding thiazolyl derivative of formula 12. If desired, the thiazolyl derivative of formula 12 can be converted by standard methods (e.g., N-alkylation, acylation, carbamate formation, etc.) with the appropriate agent to give the corresponding compound of formula 12 wherein $R^{1DA}$ has the same meaning as $R^{1D}$ as defined hereinbefore. Subsequent deprotection of the latter compound gives the 4-thiazolylpheny derivative of formula 2.

Examples of amino protective groups suitable for use in the above schemes include benzyloxycarbonyl, tert-butyloxycarbonyl, 4-methoxybenzyloxycarbonyl, 2,2,2-trichloroethoxycarbonyl or 2,2,2-trifluoroacetamide.

Other starting materials for the preceding process are known or they can readily be prepared by standard methods from known starting materials. For example, phenethylamine (8) is available from the Aldrich Chemical Co., Milwaukee, Wis., USA.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, the reaction can be successfully performed by conventional modification known to those skilled in the art, e.g. by appropriate protection of interfering groups, by changing to alternative conventional reagents, by routine modification of reaction conditions, or by modification illustrated in the examples herein.

Furthermore, if desired, the compounds of Group 5-formula 1d can be obtained in the form of a therapeutically acceptable acid addition salt. Such salts can be considered as biological equivalent of the compounds of formula 1d. Examples of such salts are those formed with hydrochloric acid, sulfuric acid, phosphoric acid, formic acid, acetic acid or citric acid.

Antiherpes Activity

The antiviral activity of the compounds of Group 5-formula 1d, or their corresponding therapeutically acceptable acid addition salts, can be demonstrated in the same manner as described herein for the compounds of Group 1-formula 1. Likewise, the compounds of Group 5-formula 1d, or their corresponding therapeutically acceptable acid addition salts, can be formulated and employed as antiviral agents in the same manner as described herein for the compounds of Group 1-formula 1.

The following examples further illustrate this invention. Temperatures are given in degrees Celsius. Solution percentages or ratios express a volume to volume relationship, unless stated otherwise. Nuclear magnetic resonance spectra were recorded on a Bruker 400 MHz spectrometer; the chemical shifts (δ) are reported in parts per million. The concentrations for the optical rotations are expressed in grams of the compound per 100 mL of solution. Abbreviations or symbols used in the examples are as defined hereinbefore.

GROUP 5 EXAMPLES

Example 1

N-{2-{4-(2-Amino-4-thiazolyl)phenyl}ethyl}-2,2,2-trifluoroacetamide (a) N-(2-Phenylethyl)-2,2,2-trifluoroacetamide: To a solution of phenethylamine (20.0 g, 165 mmol) in $CH_2Cl_2$ (350 mL) at 0° was added dropwise (5 min) trifluoroacetic anhydride (36.4 g, 173 mmol). The reaction was exothermic for the addition of the first half of the reagent. Pyridine (14.4 g, 185 mmol) was then added (10 min). The reaction was allowed to warm to room temperature and was then stirred for 16 h. The solution was washed with aqueous 10% HCl (2×200 mL) and $H_2O$ (50 mL), dried ($MgSO_4$) and concentrated under reduced pressure to give N-(2-phenylethyl)-2,2,2-trifluoroacetamide as a pale yellow solid (35.8 g, 100% yield): $^1H$ NMR (DMSO-$d_6$) δ 9.48 (broad s, 1H), 7.30 (m, 2H), 7.22 (m, 3H), 3.42 (broad q, J=6.8 Hz, 2H), 2.81 (t, J=7.3 Hz, 2H).

(b) N-{2-(4-Acetylphenyl)ethyl}-2,2,2-trifluoroacetamide: $AlC_3$ (12.2 g, 91.7 mmol) was added to an ice-cold solution of N-(2-phenylethyl)-2,2,2-trifluoroacetamide (20.0 g, 91.8 mmol), prepared in the preceding section (a), and acetyl chloride (21.6 g, 275 mmol) in $CH_2Cl_2$ (200 mL). The reaction mixture was heated at reflux for 5 h (additional amounts of AlCl$_3$, 12.2 g, were added to the ice-cold mixture after 1 and 2 h). The reaction mixture was cooled and poured into a mixture of ice (300 g) and aqueous 12N HCl (50 mL). The resulting solution was extracted with CH$_2$Cl$_2$ (4×50 mL). The combined organic extracts were washed with a saturated aqueous solution of NaHCO$_3$, dried (MgSO$_4$) and concentrated under reduced pressure. Recrystallization of the resulting residue (24.1 g) from EtOAc:hexane (2:3) gave N-{2-(4-acetylphenyl)ethyl}-2,2,2-trifluoroacetamide (16.7 g, 70% yield): $^1$H NMR (DMSO-d$_6$) δ 9.48 (broad s, 1H), 7.89 (d, J=8.2 Hz, 2H), 7.36 (d, J=8.2 Hz, 2H), 3.46 (t, J=7.2 Hz, 2H), 2.89 (t, J=7.2 Hz, 2H), 2.55 (s, 3H).

(c) N-(2-{4-(2-Bromoacetyl)phenyl)ethyl}-2,2,2-trifluoroacetamide: Bromine (3.08 g, 19.3 mmol) was added to a cold (−10°) solution of N-{2-(4-acetylphenyl)ethyl}-2,2,2-trifluoroacetamide (5.00 g, 19.3 mmol), prepared in the preceding section (b), in glacial acetic acid (20 mL) and CH$_2$Cl$_2$ (20 mL). HBr produced from KBr (200 mg, 1.68 mmol) and H$_2$SO$_4$ (1 mL) was passed into the solution in a stream of dry N$_2$. The solution was allowed to warm to 0° and stirred for 3 h. The cold solution was diluted with hexane (40 mL) and stirred vigorously at 0° for 1 h. The resulting crystals were filtered off then were washed with H$_2$O and air dried to give N-{2-{4-(2-bromoacetyl)phenyl}ethyl}-2,2,2-trifluoroacetamide (5.53 g, 85% yield): $^1$H NMR (DMSO-d$_6$) δ 9.51 (broad s, 1H), 7.94 (d, J=8.2 Hz, 2H), 7.39 (d, J=8.2 Hz, 2H), 4.89 (s, 2H), 3.47 (broad q, J=6.6 Hz, 2H), 2.90 (t, J=7.0 Hz, 2H).

(d) The title compound: A solution of N-{2-{4-(2-bromoacetyl)phenyl}ethyl}-2,2,2,-trifluoroacetamide (1.00 g, 2.96 mmol) and thiourea (225 mg, 2.96 mmol) in isopropanol (30 mL) was heated at reflux for 1 h. The reaction mixture was concentrated under reduced pressure. The residue was dissolved in a mixture of EtOAc and aqueous 10% HCl and the phases were separated. The aqueous layer was washed with EtOAc then rendered basic with solid K$_2$CO$_3$. The resulting mixture was extracted with EtOAc. The organic layer was dried (MgSO$_4$) and concentrated under reduced pressure. The residue was purified by flash chromatography (SiO$_2$, EtOAc:Hexane, 1:1) to give N-{2-{4-(2-amino-4-thiazolyl)phenyl}ethyl}-2,2,2-trifluoroacetamide (240 mg, 26% yield): M.p. 180–182°; $^1$H NMR (DMSO-d$_6$) δ 9.48 (broad t, J=5.4 Hz, 1H), 7.72 (d, J=8.4 Hz, 2H), 7.19 (d, J=8.4 Hz, 2H), 7.00 (broad s, 2H), 6.95 (s, 1H), 3.43 (broad q, J=6.8 Hz, 2H), 2.80 (t, J=7.2 Hz, 2H); MS (FAB) m/z 316 (MH)$^+$; Anal. Calcd for C$_{13}$H$_{12}$F$_3$N$_3$OS: C, 49.52; H, 3.84; N, 13.33; S, 10.17. Found: C, 49.69; H, 3.82; N, 13.36; S, 10.00.

Example 2

N-{2-{4-(2-Amino-4-thiazolyl)phenyl}ethyl}benzeneacetamide (1d: R$^{1D}$=NH$_2$, R$^{2D}$=H and R$^{3D}$=PhCH$_2$)

(a) 4-{4-(2-Aminoethyl)phenyl}-2-thiazolamine: A solution of N-{2-{4-(2-bromoacetyl)phenyl}ethyl}-2,2,2-trifluoroacetamide (5.55 g, 16.4 mmol), prepared in Example 1(b), and thiourea (1.25 g, 16.4 mmol) in isopropanol (60 mL) was heated at reflux for 1 h. The reaction mixture was concentrated under reduced pressure to give crude N-{2-{4-(2-amino-4-thiazolyl)phenyl}ethyl}-2,2,2-trifluoroacetamide hydrobromide (6.51 g, ~100% yield). A solution of the crude hydrobromide and aqueous 4N NaOH (14.3 mL, 57.4 mmol) in MeOH (70 mL) and H$_2$O (10 mL) was heated at reflux for 20 min. The solution was cooled, H$_2$O (30 mL) was added and the MeOH was carefully evaporated under reduced pressure while keeping the solution cool. The resulting suspension was cooled to 0°. The crystals obtained by filtration were washed with cold H$_2$O then air-dried to give 4-{4-(2-aminoethyl)phenyl}-2-thiazolamine (3.3 g, 92% yield): $^1$H NMR (DMSO-d$_6$) δ 7.69 (d, J=8.2 Hz, 2H), 7.18 (d, J=8.2 Hz, 2H), 7.03 (broad s, 2H), 6.92 (s, 1H), 2.76 (t, J=7.1 Hz, 2H), 2.62 (t, J=7.1 Hz, 2H).

(b) The title compound: TBTU (366 mg, 1.14 mmol) was added to an ice-cold solution of 4-{4-(2-aminoethyl)phenyl}-2-thiazolamine (250 mg, 1.14 mmol), prepared in the preceding section (a), phenylacetic acid (171 mg, 1.25 mmol) and DIPEA (162 mg, 1.25 mmol) in DMF (3 mL). The solution was stirred at room temperature for 3 h then left at 6° for 40 h. The reaction mixture was diluted with EtOAc (30 mL) and washed with aqueous saturated NaHCO$_3$ (3×30 mL). The aqueous layers were back extracted with EtOAc (30 mL). The combined organic extracts were dried (MgSO$_4$) then concentrated under reduced pressure. The residue was purified by flash chromatography (SiO$_2$, EtOAc) to give N-{2-{4-(2-amino-4-thiazolyl)phenyl}ethyl}benzeneacetamide as colorless crystals (343 mg, 84% yield): M.p. 176–177°; $^1$H NMR (DMSO-d$_6$) δ 8.07 (broad t, J=5.1 Hz, 1H), 7.69 (d, J=8.4 Hz, 2H), 7.20–7.30 (m, 5H), 7.15 (d, J=8.4 Hz, 2H), 7.00 (broad s, 2H), 6.93 (s, 1H), 3.29 (broad q, J=6.7 Hz, 2H), 2.80 (t, J=7.3 Hz, 2H); MS (FAB) m/z 338 (MH)$^+$; Anal. Calcd for C$_{19}$H$_{19}$N$_3$OS: C, 67.63; H, 5.68; N, 12.45; S, 9.50. Found: C, 67.55; H, 5.73; N, 12.38; S, 9.30.

Example 3

N-{2-{4-(2-Amino-4-thiazolyl)phenyl}ethyl}-N',N'-dibutylurea (1d: R$^{1D}$=NH$_2$, R$^{2D}$=H and R$^{3D}$=dibutylamino)

(a) Phenyl N-{2-{4-(Amino-4-thiazolyl)phenyl}ethyl}carbamate: Phenyl chloroformate (714 mg, 4.56 mmol) was added to a solution of 4-{4-(2-aminoethyl)phenyl}-2-thiazolamine (1.00 g, 4.56 mmol) and DIPEA (589 mg, 4.56 mmol) in DMF (4 mL) at 0°. The solution was stirred at room temperature for 3 h. The reaction mixture was diluted with EtOAc (30 mL) and washed with aqueous saturated NaHCO$_3$ (3×30 mL). The aqueous layers were back extracted with EtOAc (30 mL). The combined organic extracts were dried (MgSO$_4$) then concentrated under reduced pressure. The residue was purified by flash chromatography (SiO$_2$, EtOAc:Hexane, 3:2) to give phenyl N-{2-{4-(amino-4-thiazolyl)phenyl}ethyl}carbamate (941 mg, 61% yield): $^1$H NMR (DMSO-d$_6$) δ 7.82 (broad t, J=5.7 Hz, 1H), 7.73 (d, J=7.9 Hz, 2H), 7.36 (m, 2H), 7.21 (m, 3H), 7.06 (d, J=7.9 Hz, 2H), 7.01 (broad s, 2H), 6.95 (s, 1H), ca. 3.29 (m, signal beneath H$_2$O signal), 2.80 (t, J=7.3 Hz, 2H).

(b) The title compound: A solution of phenyl N-{2-{4-(amino-4-thiazolyl)phenyl}ethyl}carbamate (200 mg, 0.59 mmol), prepared in the preceding section (a), and dibutylamine (76.0 mg, 0.59 mmol) in DMSO (1 mL) was stirred at room temperature for 3 d. The reaction mixture was diluted with EtOAc (30 mL) and washed with aqueous saturated NaHCO$_3$ (2×30 mL). The aqueous layers were back extracted with EtOAc (30 mL). The combined organic extracts were dried (MgSO$_4$) then concentrated under reduced pressure. The residue was purified by flash chromatography (SiO$_2$, EtOAc:Hexane, 4:1) to give N-{2-{4-(2-amino-4-thiazolyl)phenyl}ethyl}-N',N'-dibutylurea (167 mg, 76% yield): M.p. 42–43°; $^1$H NMR (DMSO-d$_6$) δ 7.70 (d, J=8.2 Hz, 2H), 7.16 (d, J=8.2 Hz, 2H), 6.99 (broad s, 2H), 6.92 (s, 1H), 6.11 (broad t, J=5.4 Hz, 1H), 3.23 ( broad q, J=6.6 Hz, 2H), 3.09 (t, J=7.5 Hz, 4H), 2.70 (t, J=7.3 Hz, 2H), 1.37 (m, 4H), 1.21 (m, 4H), 0.86 (t, J=7.3 Hz, 6H); MS (FAB) m/z 375 (MH)$^+$.

Example 4 tert-Butyl N-{4-{4-{2-{{(dibutylamino)carbonyl}amino}ethyl}phenyl}-2-thiazolyl}carbamate (1d: $R^{1D}$=tert-butoxycarbonylamino, $R^{2D}$=H and $R^{3D}$=dibutylamino)

A solution of N-{2-{4-(2-amino-4-thiazolyl)phenyl}ethyl}-N',N'-dibutylurea (293 mg, 0.78 mmol), prepared as in Example 3(b), DIPEA (101 mg, 0.78 mmol), DMAP (9.5 mg, 0.08 mmol) and di-tert-butyl dicarbonate (171 mg, 0.78 mmol) in DMF (2 mL) was stirred at room temperature for 24 h. The reaction mixture was diluted with EtOAc (30 mL) and washed with aqueous saturated NaHCO$_3$ (2×30 mL). The aqueous layers were back extracted with EtOAc (30 mL). The combined organic extracts were dried (MgSO$_4$) then concentrated under reduced pressure. The residue was purified by flash chromatography (SiO$_2$, EtOAc:Hexane, 1:1) to give the title compound (183 mg, 49% yield): M.p. 70–75°; $^1$H NMR (DMSO-d$_6$) δ 11.53 (broad s, 1H), 7.77 (d, J=8.1 Hz, 2H), 7.48 (s, 1H), 7.22 (d, J=8.1 Hz, 2H), 6.12 (broad t, J=5.5 Hz, 1H), 3.23 (broad q, J=6.7 Hz, 2H), 3.09 (t, J=7.5 Hz, 4H), 2.72 (t, J=7.2 Hz, 2H), 1.49 (s, 9H), 1.37 (m, 4H), 1.21 (m, 4H), 0.85 (t, J=7.3 Hz, 6H); MS (FAB) m/z 475 (MH)+; Anal. calcd for C$_{25}$H$_{38}$N$_4$O$_3$S: C, 63.26; H, 8.07; N, 11.80; S, 6.41. Found: C, 62.95; H, 8.14; N, 11.80; S, 6.41.

Example 5

In conjunction with the appropriate starting materials and intermediates, the procedures of Group 5-Examples 1 to 4 can be used to prepare other compounds of Group 5-formula 1d. Examples of compounds thus prepared are listed in Table 1 of Group 5-Example 5, together with mass spectrum data for the individual compounds and the results obtained from assays demonstrating antiherpes activity. The assays have been described hereinbefore.

TABLE 1

Compound of formula 1d having the structure:

| ENTRY No | $R^{1D}$ | $R^{2D}$ | $R^{3D}$ | FAB/MS (m/z) (MH)+ | HSV-1 IC$_{50}$ (μM) | HSV-1 EC$_{50}$ (μM) | ELISA CMV EC$_{50}$ (μM) | PRA CMV EC$_{50}$ (μM) |
|---|---|---|---|---|---|---|---|---|
| 1 | NH$_2$ | H | 5-Cl-2-MeOPh | 388 | | | 5.9 | >22* |
| 2 | NH$_2$ | H | Ph | 324 | 11 | 4 | 2.0 | >26* |
| 3 | NH$_2$ | H | CF$_3$ | 316 | >50 | | | >83 |
| 4 | NH$_2$ | H | 3-pyridinyl | 325 | | | | >81 |
| 5 | NH$_2$ | H | PhCH$_2$ | 338 | 40 | | | 70 |
| 6 | NH$_2$ | H | Me$_3$CCH$_2$ | 318 | >50 | | | 88 |
| 7 | NH$_2$ | H | Me$_3$CO | 320 | >50 | | | >17 |
| 8 | NH$_2$ | H | (4-FPh)CH$_2$NH | 371 | 45 | | | >14* |
| 9 | NH$_2$ | H | Bu$_2$N | 375 | 14 | | | 16 |
| 10 | NH$_2$ | PhCH$_2$ | Ph | 414 | >50 | | | 12 |
| 11 | NH$_2$ | PhCH$_2$ | 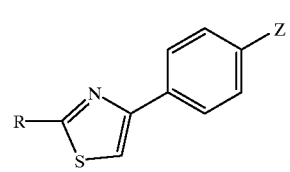 | 420 | 6 | | | 12* |
| 12 | NH$_2$ | PhCH$_2$ | 4-pyridinyl | 415 | >50 | | | 7.7 |
| 13 | NH$_2$ | PhCH$_2$ | CF$_3$ | 406 | >50 | | | 21 |
| 14 | (Me$_3$COC(O))$_2$N | H | Ph | 524 | >50 | | | 6.7 |
| 15 | NH$_2$ | PhCH$_2$ | PhCH$_2$ | 428 | | | | 7.0 |
| 16 | Me$_3$COC(O)NH | H | Bu$_2$N | 475 | >50 | | | 1.9 |
| 17 | Me$_3$COC(O)NH | PhCH$_2$ | Ph | | | | | 49 |

*Cytotoxic at this concentration

What is claimed is:

1. A compound of the formula:

(G)

wherein:
R is selected from the group consisting of hydrogen, lower alkyl, amino, lower alkylamino, di(lower alkyl)amino, lower alkanoylamino, (lower alkoxycarbonyl)amino, di(lower alkoxycarbonyl)amino and {(lower alkylamino)carbonyl}amino; and Z is selected from the group consisting of:
(i) NR$^2$—C(O)—Q—CH(R$^3$)—NR$^4$R$^5$ wherein:
  R$^2$ is hydrogen or lower alkyl;
  Q is absent (i.e. a valance bond) or methylene;
  R$^3$ is hydrogen, lower alkyl, phenyl(lower alkyl) or phenyl(lower alkyl) monosubstituted on the aromatic portion thereof with a halo, hydroxy, lower alkoxy or lower alkyl;
  R$^4$ is hydrogen, (1-8C)alkyl, {di(lower alkyl)amino}-(lower alkyl), phenyl(lower)alkyl, phenyl(lower)alkyl monosubstituted or disubstituted on the aromatic portion thereof with a halo, hydroxy, lower alkoxy or lower alkyl; 1-indanyl, 2-indanyl, (lower cycloalkyl)-(lower alkyl); and
  R$^5$ is (1-8C)alkyl, phenyl(lower alkyl), phenyl(lower alkyl) monosubstituted on the aromatic portion thereof with a halo, hydroxy, lower alkoxy or lower alkyl; 1-indanyl, 2-indanyl, (lower cycloalkyl)-(lower alkyl), phenyl-sulfonyl, 1- or 2-naphthylsulphonyl, 5-(dimethylamino)-1-naphthylsulfonyl, (lower alkylamino)sulfonyl, {di(lower alkyl)amino}sulfonyl, lower alkanoyl, (lower cycloalkyl)-(lower alkanoyl), {1-(lower alkyl)-(lower cycloalkyl)}-carbonyl, (lower alkoxy)carbonyl, phenyl-Y—(CH$_2$)$_n$C(O) wherein Y is oxy (—O—) or thio (—S—) and n is 0, 1 or 2 when Y is oxy or n is 1 or 2 when Y is thio, monosubstituted or disubstituted phenyl-Y—(CH$_2$)$_2$C(O) wherein Y and n are as defined in this claim and the monosubstitution or disubstitution occurs on the phenyl portion thereof with a substituent selected from the group consisting of halo, hydroxy, lower alkoxy and lower alkyl; phenyl(lower alkanoyl), phenyl(lower alkanoyl) monosubstituted or disubstituted on the phenyl portion thereof with a substituent selected independently from the group consisting of azido, halo, hydroxy, lower alkoxy and lower alkyl; 2-{(lower alkoxycarbonyl)amino}-1-oxoethyl, (lower alkylamino)carbonyl, {di(lower alkyl)amino}carbonyl or (lower alkylamino)thiocarbonyl;
(ii) NR$^{2A}$C(O)—A—NR$^{3A}$R$^{4A}$ wherein:
  R$^{2A}$ is hydrogen or lower alkyl;
  A is absent or carbonyl;
  R$^{3A}$ is hydrogen, (1-8C)alkyl, 2-hydroxyethyl, 3-hydroxypropyl, (1-3C)alkyl monosubstituted with cyano, phenyl(lower alkyl), phenyl(lower alkyl) monosubstituted or disubstituted on the aromatic portion thereof with a halo, hydroxy, di(lower alkyl)amino, lower alkoxy or lower alkyl; (lower cycloalkyl)-(lower alkyl); and
  R$^{4A}$ is (1-8C)alkyl, phenyl(lower alkyl), phenyl(lower alkyl) monosubstituted or disubstituted on the aromatic portion thereof with a halo, hydroxy, di(lower alkyl)amino, lower alkoxy or lower alkyl; 1-indanyl, 2-indanyl, phenyl(lower alkyl) monosubstituted on the aliphatic portion thereof with a hydroxy; (lower cycloalkyl)-(lower alkyl); or R$^{3A}$ and R$^{4A}$ independently are:

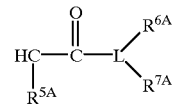

wherein L is carbon, oxygen or nitrogen, with the proviso that when L is oxygen, one of R$^{6A}$ or R$^{7A}$ is absent; R$^{5A}$ and R$^{6A}$ are independently selected from the group defined for R$^{3A}$ in this claim; and R$^{7A}$ is independently selected from the group defined for R$^{4A}$ in this claim;

or a therapeutically acceptable acid addition salt thereof.

2. The compound of formula 1 according to claim 1

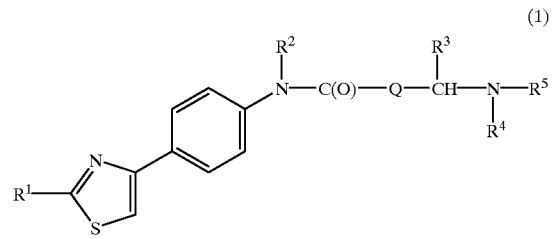

wherein
  R$^1$ is selected from the group consisting of hydrogen, lower alkyl, amino, lower alkylamino, di(lower alkyl)amino, lower alkanoylamino, (lower alkoxycarbonyl)amino and {(lower alkylamino)carbonyl}amino;
  R$^2$ is hydrogen, methyl or ethyl;
  Q is absent or methylene;
  R$^3$ is hydrogen, lower alkyl, phenylmethyl or phenylmethyl substituted on the 4 position of the phenyl ring with halo, lower alkoxyl or lower alkyl;
  R$^4$ is hydrogen, (1-8C)alkyl, {di(lower alkyl)amino}-(lower alkyl), phenyl-(1-3C)alkyl, phenyl-(1-3C)alkyl monosubstituted on the aromatic portion thereof with halo, hydroxy, lower alkoxy or lower alkyl; 1-indanyl, 2-indanyl or (lower cycloalkyl)-(lower alkyl); and
  R$^5$ is (1-8C)alkyl, lower cyclohexyl, phenyl-(1-3C)alkyl, phenyl-(1-3C)alkyl monosubstituted on the aromatic portion thereof with halo, hydroxy, lower alkoxy or lower alkyl; 1-indanyl, 2-indanyl, (lower cycloalkyl)-(1-3C)alkyl, phenylsulfonyl, 5-(dimethylamino)-1-naphthylsulfonyl, (lower alkylamino)sulfonyl, {di(lower alkyl)amino}sulfonyl, lower alkanoyl, (lower cycloalkyl)-(lower alkanoyl), (1-methylcyclohexyl)carbonyl, (lower alkoxy)carbonyl, (phenylmethoxy)carbonyl, 2-phenoxyacetyl, 2-phenoxyacetyl monosubstituted or disubstituted on the phenyl ring with a substituent selected independently from the group consisting of bromo, chloro, fluoro, iodo, methoxy and methyl; phenyl-(1-3C)alkanoyl, phenyl-(1-3C)alkanoyl monosubstituted or disubstituted with a substituent selected independently from the group consisting of azido, bromo, chloro, fluoro, iodo, methoxy and methyl; 2-{(lower alkoxycarbonyl)amino}-1-oxoethyl, (lower alkylamino)carbonyl, {di(lower alkyl)amino}carbonyl or (lower alkylamino)thiocarbonyl; or a therapeutically acceptable acid addition salt thereof.

3. A compound of formula 1 of claim 2 wherein $R^1$ is hydrogen, amino, methyl, methylamino, dimethylamino, acetylamino, (1,1-dimethylethoxycarbonyl)amino or {(1,1-dimethylethylamino)carbonyl}amino;

$R^2$ is hydrogen or methyl;

Q is absent or methylene;

$R^3$ is hydrogen, methyl or phenylmethyl;

$R^4$ is hydrogen, methyl, ethyl, propyl, butyl, 2-methylpropyl, 2,2-dimethylpropyl, 1-propylbutyl, 2-(dimethylamino)ethyl, phenylmethyl, 1(R)-phenylethyl, 1(S)-phenylethyl, 2-phenylethyl, (4-chlorophenyl)methyl, (2-fluorophenyl)methyl, (3-fluorophenyl)methyl, (4-fluorophenyl)methyl, (4-methoxyphenyl)methyl, (2-methylphenyl)methyl, 1-indanyl, 2-indanyl, cyclopentylmethyl, cyclohexylmethyl, 1(S)-cyclohexylethyl, 2-cyclohexylethyl; and $R^5$ is methyl, ethyl, propyl, butyl, 2,2-dimethylpropyl, 1-propylbutyl, cyclohexyl, phenylmethyl, 1(R)-phenylethyl, 1(S)-phenylethyl, 2-phenylethyl, (4-chlorophenyl)methyl, (2-fluorophenyl)methyl, (3-fluorophenyl)methyl, (4-fluorophenyl)methyl, (2-hydroxyphenyl)methyl, 4-(methoxyphenyl)methyl, (2-methylphenyl)methyl, 1-indanyl, 2-indanyl, cyclopentylmethyl, cyclohexyl-methyl, 2-cyclohexylethyl, phenylsulfonyl, 5-(dimethylamino)-1-naphthylsulfonyl, (dimethylamino)sulfonyl, acetyl, 2-methylpropionyl, 2,2-dimethylpropionyl, 3,3-dimethylbutyryl, cyclopentylcarbonyl, cyclohexylcarbonyl, cycloheptylcarbonyl, cyclopentylacetyl, cyclohexylacetyl, cycloheptylacetyl, (1-methylcyclohexyl)carbonyl, (1-methylethoxy)carbonyl, (1,1-dimethylethoxy)carbonyl, (2-methylpropoxy)carbonyl, (phenylmethoxy)carbonyl, (2-phenoxy)acetyl, 2-(4,6-dimethylphenoxy)acetyl, benzoyl, phenylacetyl, (4-azidophenyl)carbonyl, (2-fluorophenyl)carbonyl, (3-fluorophenyl)carbonyl, (4-fluorophenyl)carbonyl, (2,6-dimethylphenyl)carbonyl, 2-{(1,1-dimethylethoxycarbonyl)amino}-1-oxoethyl, (1,1-dimethylethylamino)carbonyl, (N,N-dibutylamino)carbonyl, {N-methyl-N-(1,1-dimethylethyl)amino}carbonyl, or (1,1-dimethylethylamino)thiocarbonyl;

or a therapeutically acceptable acid addition salt thereof.

4. A compound of formula 1 of claim 3 wherein $R^1$ is hydrogen, amino, methylamino or dimethylamino;

$R^2$ is hydrogen or methyl;

Q is absent;

$R^3$ is hydrogen, methyl or phenylmethyl;

$R^4$ is methyl, phenylmethyl, 1(R)-phenylethyl, 1(S)-phenylethyl, 2-phenylethyl, (4-chlorophenyl)methyl, (2-fluorophenyl)methyl, (4-fluorophenyl)methyl, (4-methoxyphenyl)methyl or (2-methylphenyl)methyl; and $R^5$ is 2,2-dimethylpropionyl, 3,3-dimethylbutyryl, cyclopentylcarbonyl, cyclohexylcarbonyl, cycloheptylcarbonyl, cyclopentylacetyl, cyclohexylacetyl, (1-methylcyclohexyl)carbonyl, (1,1-dimethylethoxy)-carbonyl, (2-methylpropoxy)carbonyl, benzoyl, (4-fluorophenyl)carbonyl, (2,6-dimethylphenyl)carbonyl or (1,1-dimethylethylamino)carbonyl; and the carbon atom bearing the $R^3$ group when $R^3$ is methyl or phenylmethyl has the (R) or (S) configuration;

or a therapeutically acceptable acid addition salt thereof.

5. A compound of formula 1 of claim 3 wherein $R^1$ is amino, methylamino, dimethylamino, acetylamino, (1,1-dimethylethoxy)carbonylamino or {(1,1-dimethylethylamino)carbonyl}amino;

$R^2$ is hydrogen;

Q is absent or methylene;

$R^3$ is hydrogen or phenylmethyl;

$R^4$ is hydrogen, methyl, 2,2-dimethylpropyl, phenylmethyl, 1(R)-phenylethyl, 1(S)-phenylethyl, 2-phenylethyl, (4-chlorophenyl)methyl, (2-methylphenyl)methyl, 1-indanyl, 2-indanyl or cyclohexylmethyl; and $R^5$ is methyl, phenylmethyl, (2-fluorophenyl)methyl, (4-fluorophenyl)methyl, (2-hydroxyphenyl)methyl, 2,2-dimethylpropionyl, 3,3-dimethylbutyryl, cyclopentylcarbonyl, cyclohexylcarbonyl, cycloheptylcarbonyl, cyclopentylacetyl, cyclohexylacetyl, (1,1-dimethylethoxy)carbonyl, (2-methylpropoxy)carbonyl, (2-phenoxy)acetyl, 2-(2,6-dimethylphenoxy)acetyl, benzoyl, phenylacetyl, {(1,1-dimethylethyl)amino}carbonyl or {(1,1-dimethylethyl)amino}thiocarbonyl; and the carbon atom bearing the $R^3$ group when $R^3$ is phenylmethyl has the (R) or (S) configuration;

or a therapeutically acceptable acid addition salt thereof.

6. A compound of formula 1 of claim 2 selected from the group consisting of:

(i) a compound of formula 1 wherein $R^1$ is amino, $R^2$ and $R^3$ each is hydrogen, Q is absent, and $R^4$ and $R^5$ are as defined by one of the following combinations:

| | Combinations of $R^4$ and $R^5$ | |
|---|---|
| $R^4$ | $R^5$ |
| H | PhCH$_2$ |
| H | PhCH$_2$CH$_2$ |
| H | PhCH$_2$CH$_2$CH$_2$ |
| H | (4-FPh)CH$_2$ |
| H | (4-ClPh)CH$_2$ |
| H | (4-MePh)CH$_2$ |
| H | (4-MeOPh)-CH$_2$ |
| H | 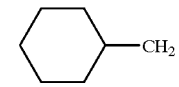 |
| H | (3-FPh)CH$_2$ |
| H | Ph-(S)—CHMe |
| H | Ph-(R)—CHMe |
| PhCH$_2$ | Me |
| PhCH$_2$ | PhCH$_2$ |
| (2-FPh)CH$_2$ | (2-FPh)CH$_2$ |
| (3-FPh)CH$_2$ | (3-FPh)CH$_2$ |
| PhCH$_2$ | PhC(O) |
| PhCH$_2$ | (4F-Ph)C(O) |
| PhCH$_2$ | (2,6-Me$_2$-Ph)C(O) |
| PhCH$_2$ | PhCH$_2$C(O) |

-continued

Combinations of R⁴ and R⁵

| R⁴ | R⁵ |
|---|---|
| PhCH₂ |  cyclohexyl-C(O) |
| PhCH₂ |  1-methylcyclohexyl-C(O) |
| PhCH₂ |  cyclopentyl-C(O) |
| PhCH₂ |  cycloheptyl-C(O) |
| PhCH₂ |  cyclohexyl-CH₂C(O) |
| PhCH₂ |  cyclopentyl-CH₂C(O) |
| PhCH₂ | Me₃CC(O) |
| PhCH₂ | Me₃CCH₂C(O) |
| PhCH₂ | Me₂CHC(O) |
| PhCH₂ | MeC(O) |
| (4-ClPh)CH₂ |  cyclohexyl-C(O) |
| (4-MeOPh)—CH₂ |  cyclohexyl-C(O) |
| Ph-(R)—CHMe |  cyclohexyl-C(O) |
| Ph-(S)—CHMe |  cyclohexyl-C(O) |
| (4-FPh)CH₂ | PhC(O) |
|  cyclohexyl-CH | PhC(O) |
|  cyclohexyl-CH |  cyclopentyl-C(O) |

-continued

Combinations of R⁴ and R⁵

| R⁴ | R⁵ |
|---|---|
| (4-ClPh)CH₂ | 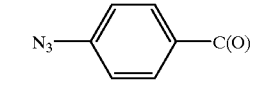 4-azidophenyl-C(O) |
| PhCH₂CH₂ | 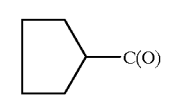 cyclopentyl-C(O) |
| PhCH₂CH₂ | 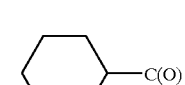 cyclohexyl-C(O) |
| (4-ClPh)CH₂ | 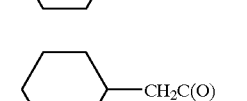 cyclohexyl-CH₂C(O) |
| PhCH₂ | NH₂CH₂C(O) |
| PhCH₂ | Me₃COC(O)—NHCH₂C(O) |
| PhCH₂ | 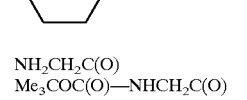 4-azidophenyl-C(O) |
| cyclohexyl-CH₂ | 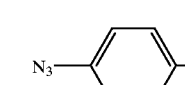 cyclopentyl-CH₂C(O) |
| cyclohexyl-CH₂ | 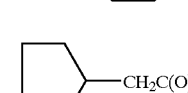 cyclohexyl-CH₂C(O) |
| cyclohexyl-CH₂ | PhCH₂C(O) |
| Me₃CCH₂ | 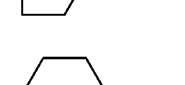 cyclohexyl-C(O) |
| Me₂CHCH₂ | 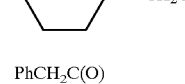 cyclohexyl-C(O) |
| Pr₂CH |  cyclohexyl-C(O) |
| (4-FPh)CH₂ | 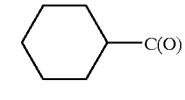 cyclohexyl-C(O) |
| PhCH₂ | Me₃COC(O) |
| PhCH₂ | Me₂CHCH₂O—C(O) |
| PhCH₂ | MeOC(O) |
| Ph-(R)—CHMe | Me₃COC(O) |

-continued

| Combinations of R⁴ and R⁵ | |
|---|---|
| R⁴ | R⁵ |
| Ph-(S)—CHMe | Me₃COC(O) |
| (4-ClPh)CH₂ | Me₃COC(O) |
| PhCH₂ | Me₃CNHC(O) |
| PhCH₂ | Me₃CNHC(S) |
| PhCH₂ | Me₃CN(Me)—C(O) |
| PhCH₂ | PhSO₂ |
| PhCH₂ | 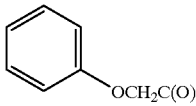 |
| 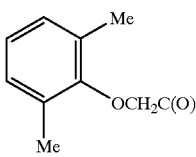 | Me₃COC(O) |
| 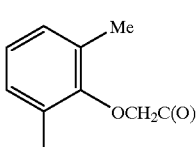 | 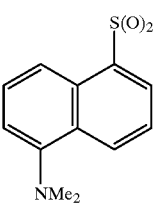 |
| PhCH₂ | Et₂CHC(O) |
| Ph-(S)—CHMe | Me₃CNHC(O) |
| PhCH₂ | Me₂NSO₂ |
| 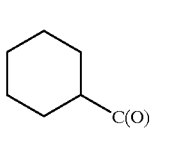 | Me₃COC(O) |
| PhCH₂ | PhCH₂OC(O) |
| Me₂CHCH₂ | PhCH₂OC(O) |
| Pr₂CH | Me₃COC(O) |

-continued

| Combinations of R⁴ and R⁵ | |
|---|---|
| R⁴ | R⁵ |
| Me₂CHCH₂ | Me₃COC(O) |
| PhCH₂ | 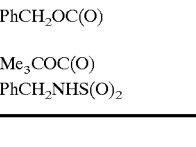 |
| PhCH₂ | 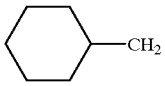 |
| (2-MePh)CH₂ | 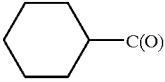 |
| Me₂NCH₂CH₂ | 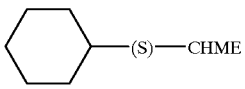 |
| Pr₂CH | PhCH₂OC(O) |
| Me₂CCH₂ | Me₃COC(O) |
| PhCH₂ | PhCH₂NHS(O)₂ |

(ii) a compound of formula 1 wherein R¹ is amino, R² and R³ each is H, and Q, R⁴ and R⁵ are as defined by one of the following combinations:

| Combinations of Q, R⁴ and R⁵ | | |
|---|---|---|
| Q | R⁴ | R⁵ |
| CH₂ | H | PhCH₂ |
| CH₂ | PhCH₂ | PhCH₂ |
| CH₂ | PhCH₂ | PhC(O) |
| CH₂ | H | (3-FPh)CH₂ |
| CH₂ | (3-FPh)CH₂ | PhC(O) |
| CH₂ | PhCH₂ | 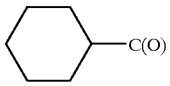 |
| CH₂ | H | 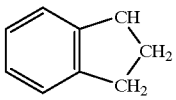 |

-continued

Combinations of Q, R⁴ and R⁵

| Q | R⁴ | R⁵ |
|---|---|---|
| CH₂ | H | 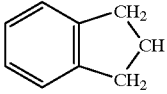 |
| CH₂ | 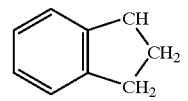 | Me₃COC(O) |
| CH₂ |  | Me₃COC(O) |
| CH₂ | PhCH₂ | Me₃COC(O) |
| CH₂ | PhCH₂ | PhCH₂OC(O) |
| CH₂ | PhCH₂ |  |
| CH₂ | Ph-(S)—CHMe | Me₃COC(O) |
| CH₂ | PhCH₂ | Ph-(S)—CHMe |
| CH₂ | H | Ph-(S)—CHMe |
| CH₂ | 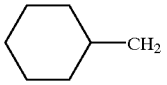 | Me₃COC(O) |
| CH₂ | H | 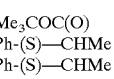 |
| CH₂ | H | Pr₂CH |
| CH₂ | H | Ph-(R)—CHMe |
| CH₂ | Ph-(S)—CHMe | Me |
| CH₂ | PhCH₂ | 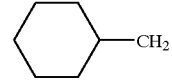 |

(iii) a compound of formula 1 wherein R³ is hydrogen, Q is absent and R¹, R², R⁴ and R⁵ are as defined by one of the following combinations:

Combinations of R¹, R², R⁴ and R⁵

| R¹ | R² | R⁴ | R⁵ |
|---|---|---|---|
| NH₂ | Me | PhCH₂ | 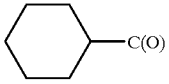 |
| NH₂ | Me | H | PhCH₂ |

-continued

Combinations of $R^1$, $R^2$, $R^4$ and $R^5$

| $R^1$ | $R^2$ | $R^4$ | $R^5$ |
|---|---|---|---|
| Me | H | PhCH$_2$ | 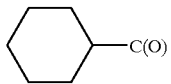—C(O) |
| H | H | PhCH$_2$ | 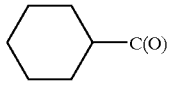—C(O) |
| NHMe | H | PhCH$_2$ | PhC(O) |
| NHMe | H | H | PhCH$_2$ |
| NHMe | H | PhCH$_2$ | 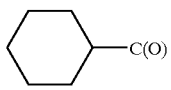—C(O) |
| NMMe | H | PhCH$_2$ | Me$_3$COC(O) |
| NMe$_2$ | H | PhCH$_2$ | PhC(O) |
| NMe$_2$ | H | H | PhCH$_2$ |
| NMe$_2$ | H | H | 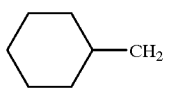—CH$_2$ |
| NMe$_2$ | H | PhCH$_2$ | Me$_3$COC(O) |
| NMe$_2$ | H | 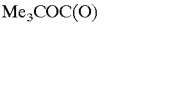—CH$_2$ | Me$_3$COC(O) |
| Me—C(O)NH | H | PhCH$_2$ | CH$_3$C(O) |
| Me$_2$CH | H | PhCH$_2$ | PhC(O) |
| Me$_3$CO—C(O)NH | H | Ph—(R)—CHMe | 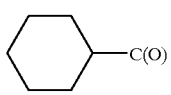—C(O) |
| Me—C(O)NH | H | Ph—(R)—CHMe | 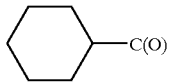—C(O) |

(iv) a compound of formula 1 wherein $R^2$ and $R^3$ each are hydrogen, Q is CH$_2$ and $R^1$, $R^4$ and $R^5$ are as defined by one of the following combinations:

Combinations of $R^1$, $R^4$ and $R^5$

| $R^1$ | $R^4$ | $R^5$ |
|---|---|---|
| Me$_3$COC(O)NH | PhCH$_2$ | PhCH$_2$ |
| Me$_3$CNHC(O)NH | PhCH$_2$ | PhCH$_2$ |

(v) a compound of formula 1 wherein $R^1$ is amino, $R^2$ is hydrogen, Q is absent and $R^3$, $R^4$ and $R^5$ are as defined by one of the following combinations:

Combinations of $R^3$, $R^4$ and $R^5$

| $R^3$ | $R^4$ | $R^5$ |
|---|---|---|
| (S)—PhCH$_2$ | H | 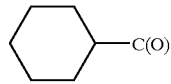—C(O) |
| (R)—PhCH$_2$ | H | 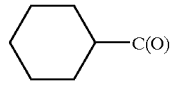—C(O) |
| (S)—PhCH$_2$ | H | Me$_3$COC(O) |
| (R)—PhCH$_2$ | H | Me$_3$COC(O) |

| Combinations of $R^3$, $R^4$ and $R^5$ | | |
|---|---|---|
| $R^3$ | $R^4$ | $R^5$ |
| (S)—PhCH$_2$ | Me | ⌬—C(O) |
| (S)—PhCH$_2$ | H | PhCH$_2$ |
| (R)—PhCH$_2$ | H | PhCH$_2$ |
| (S)—PhCH$_2$ | H | Me |
| (R)—PhCH$_2$ | PhCH$_2$ | ⌬—C(O) |
| (S)—PhCH$_2$ | Me | Me$_3$COC(O) |
| (S)—PhCH$_2$ | PhCH$_2$ | ⌬—C(O) |
| (S)—Me | H | PhCH$_2$ |
| (R)—Me | H | PhCH$_2$ |
| (S)—Me | PhCH$_2$ | ⌬—C(O) |
| (R)—Me | PhCH$_2$ | ⌬—C(O) |
| (S)—Me | PhCH$_2$ | Me$_3$COC(O) |
| (R)—Me | PhCH$_2$ | Me$_3$COC(O) |
| (R)—PhCH$_2$ | H | Me |
| (S)—PhCH$_2$ | PhCH$_2$ | ⌬—C(O) |
| (R)—PhCH$_2$ | PhCH$_2$ | ⌬—C(O) |
| (S)—PhCH$_2$ | H | Me$_3$CCH$_2$C(O) |
| (S)—PhCH$_2$ | H | Me$_3$CC(O) |
| (S)—PhCH$_2$ | H | MeC(O) |
| (S)—PhCH$_2$ | H | Me$_2$CHOC(O) |
| (S)—PhCH$_2$ | Me | Me$_3$COC(O) |
| (S)—PhCH$_2$ | H | PhCH$_2$OC(O) and |
| (S)⌬—CH$_2$ | H | Me$_3$COC(O). |

7. The compound according to claim 1 wherein

R is selected from the group consisting of hydrogen, lower alkyl, amino, lower alkylamino, di(lower alkyl) amino, lower alkanoylamino, (lower alkoxycarbonyl) amino and {(lower alkylamino)carbonyl}amino;

$R^{2A}$ is hydrogen, methyl or ethyl;

A is absent or carbonyl;

$R^{3A}$ is hydrogen, (1-8C)alkyl, 2-hydroxyethyl, 3-hydroxypropyl, (1-3C)alkyl monosubstituted with cyano, phenyl-(1-3C)alkyl, phenyl-(1-3C)alkyl monosubstituted or disubstituted on the aromatic portion thereof with halo, hydroxy, di(lower alkyl)amino, lower alkoxy or lower alkyl; or (lower cycloalkyl)-(lower alkyl); and $R^{4A}$ is (1-8C)alkyl, phenyl-(1-3C)alkyl, phenyl-(1-3C) alkyl monosubstituted or disubstituted on the aromatic portion thereof with halo, hydroxy, di(lower alkyl) amino, lower alkoxy or lower alkyl; 1-indanyl, 2-indanyl, (lower cycloalkyl)-(1-3C)alkyl;

or $R^4A$ is:

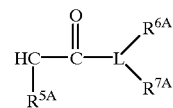

wherein

L is oxygen or nitrogen, with the proviso that when L is oxygen, one of $R^{6A}$ or $R^{7A}$ is absent;

$R^{5A}$ and $R^{6A}$ are independently selected from the group defined for $R^{3A}$ herein; and $R^{7A}$ is independently selected from the group defined for $R^{4A}$ herein;

or a therapeutically acceptable acid addition salt thereof.

8. The compound of claim 7 wherein

R is hydrogen, amino, methyl, methylamino, butylamino, dimethylamino, acetylamino or (1,1-dimethylethoxycarbonyl)amino;

$R^{2A}$ is hydrogen or methyl;

A is absent or carbonyl;

$R^{3A}$ is hydrogen, methyl, ethyl, propyl, butyl, 2-methylpropyl, 2,2-dimethylpropyl, 1-propylbutyl, 2-hydroxyethyl, cyanomethyl, phenylmethyl, 2-phenylethyl, (4-chlorophenyl)methyl, (2-fluorophenyl)methyl, (3-fluorophenyl)methyl, (4-fluorophenyl)methyl, {4-(dimethylamino) phenyl}methyl, (4-methoxyphenyl)methyl, (2-methylphenyl)methyl, cyclopentylmethyl, cyclohexylmethyl or 2-cyclohexylethyl; and $R^{4A}$ is 1,1-dimethylethyl, butyl, 2,2-dimethylpropyl, 1-propylbutyl, phenylmethyl, 1(R)-phenylethyl, 1(S)-phenylethyl, 2-phenylethyl, (4-chlorophenyl)methyl, (2-fluorophenyl)methyl, (3-fluorophenyl)methyl, (4-fluorophenyl)methyl, 4-(methoxyphenyl)methyl, {4-(dimethylamino)phenyl}methyl, (2-methylphenyl) methyl, 1-indanyl, 2-indanyl, cyclopentylmethyl, cyclohexylmethyl; or $R^{4A}$ is:

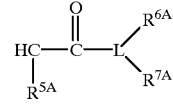

wherein L oxygen or nitrogen, with the proviso that when L is oxygen, one of $R^{6A}$ or $R^{7A}$ is absent;

$R^{5A}$ and $R^{6A}$ are independently selected from the group defined for $R^{3A}$ herein; and $R^{7A}$ is independently selected from the group defined for $R^{4A}$ herein;

or a therapeutically acceptable acid addition salt thereof.

9. The compound of claim 8 wherein

R is amino, methylamino, dimethylamino or (1,1-dimethylethoxycarbonyl)amino;

$R^{2A}$ is hydrogen;

A is absent;

$R^{3A}$ is hydrogen, methyl or butyl; and $R^{4A}$ is 1,1-dimethylethyl, butyl, 1-propylbutyl, phenylmethyl, 2-phenylethyl, 4-fluorophenylmethyl, or $R^{4A}$ is

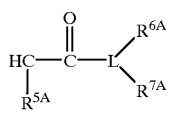

wherein L is nitrogen, $R^{5A}$ is phenylmethyl, $R^{6A}$ is methyl, L is oxygen, $R^{5A}$ is phenylmethyl, $R^{6A}$ is absent and $R^{7A}$ is 1,1-dimethylethyl;

or a therapeutically acceptable acid addition salt thereof.

10. The compound of claim 8 wherein

R is amino, methylamino, butylamino, dimethylamino or (1,1-dimethylethoxycarbonyl)amino;

$R^{2A}$ is hydrogen;

A is absent;

$R^{3A}$ is hydrogen, methyl, ethyl, butyl, 2-hydroxyethyl, cyanomethyl or phenylmethyl; and $R^{4A}$ is butyl or phenylmethyl;

or a therapeutically acceptable acid addition salt therof.

11. The compound of claim 8 wherein

R is amino, $R^{2A}$ is hydrogen, A is carbonyl, $R^{3A}$ is butyl or phenylmethyl, and $R^{4A}$ is butyl or phenylmethyl, or a therapeutically acceptable acid addition salt therof.

12. The compound as defined in claim 7 selected from the group consisting of:

(i) a compound of formula 1a wherein A is absent, $R^{2A}$ is hydrogen, $R^{3A}$ and $R^{4A}$ are as defined by one of the following combinations:

| Combination of R, $R^{3A}$ and $R^{4A}$ | | |
|---|---|---|
| R | $R^{3A}$ | $R^{4A}$ |
| $NH_2$ | Bu | Bu |
| $NH_2$ | H | Bu |
| $NH_2$ | H | (4-FPh)$CH_2$ |
| $NH_2$ | H | 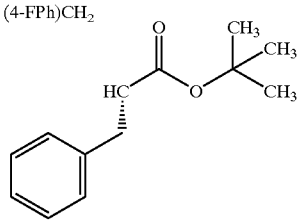 |

| Combination of $R^{1A}$, $R^{3A}$ and $R^{4A}$ | | |
|---|---|---|
| $R^{1A}$ | $R^{3A}$ | $R^{4A}$ |
| $NH_2$ | H | HC(CH$_3$)CH$_2$CH$_3$ (isopentyl structure) |
| $NH_2$ | H | C(CH$_3$)$_3$ |
| $NH_2$ | H | CH$_2$Ph |
| Me$_3$COC(O)NH | Bu | Bu |
| $NH_2$ | H | (PhCH$_2$)$_2$NCH$_2$CH$_2$ |
| $NH_2$ | H | HC≡CCH$_2$ |
| $NH_2$ | H | PhCH$_2$ |
| $NH_2$ | H | (4-ClPh)CH$_2$ |
| $NH_2$ | H | (3-FPh)CH$_2$ |
| $NH_2$ | H | (2-FPh)CH$_2$ |
| $NH_2$ | H | (4-FPh)CH$_2$CH$_2$ |
| $NH_2$ | H | (4-Me$_2$NPh)CH$_2$ |
| $NH_2$ | H | Ph—(S)—CHMe |
| $NH_2$ | H | (S)—(PhCH$_2$)CHCH$_2$OH |
| Me$_3$COC(O)NH | Me | Bu |
| Me$_3$COC(O)NH | Et | Bu |
| Me$_3$COC(O)NH | HOCH$_2$CH$_2$ | Bu |
| Me$_3$COC(O)NH | NC—CH$_2$ | Bu |
| BuNH | Bu | Bu |

(ii) and a compound of formula 1a wherein A is carbonyl, $R^{1A}$ is amino, $R^{2A}$ is hydrogen, and $R^{3A}$ and $R^{4A}$ are as defined by one of the following combinations:

| Combination of $R^{3A}$ and $R^{4A}$ | |
|---|---|
| $R^{3A}$ | $R^{4A}$ |
| Butyl | Butyl and |
| CH$_2$Ph | CH$_2$Ph. |

13. A pharmaceutical composition comprising the compound according to claim 1 and a pharmaceutically acceptable carrier.

14. The pharmaceutical composition according to claim 13, wherein the composition is suitable for oral administration.

15. The pharmaceutical composition according to claim 13, wherein the composition is suitable for topical administration.

* * * * *